United States Patent
Li et al.

(10) Patent No.: US 11,387,096 B2
(45) Date of Patent: Jul. 12, 2022

(54) WAFER LEVEL SEQUENCING FLOW CELL FABRICATION

(71) Applicant: MGI Tech Co., Ltd., Guangdong (CN)

(72) Inventors: Shifeng Li, Fremont, CA (US); Jian Gong, Danville, CA (US); Yan-You Lin, Fremont, CA (US); Cheng Frank Zhong, Menlo Park, CA (US)

(73) Assignee: MGI Tech Co., Ltd., Shenzhen (CN)

( * ) Notice: Subject to any disclaimer, the term of this patent is extended or adjusted under 35 U.S.C. 154(b) by 0 days.

(21) Appl. No.: 16/991,253

(22) Filed: Aug. 12, 2020

(65) Prior Publication Data

US 2021/0013025 A1    Jan. 14, 2021

Related U.S. Application Data

(63) Continuation of application No. 16/128,120, filed on Sep. 11, 2018, now Pat. No. 10,784,103.
(Continued)

(51) Int. Cl.
*H01L 21/02* (2006.01)
*H01L 29/20* (2006.01)
(Continued)

(52) U.S. Cl.
CPC ...... *H01L 21/022* (2013.01); *B01L 3/502707* (2013.01); *G01N 21/05* (2013.01);
(Continued)

(58) Field of Classification Search
CPC ............ H01L 21/022; H01L 21/02131; H01L 21/02175; H01L 21/02266;
(Continued)

(56) References Cited

U.S. PATENT DOCUMENTS 6,210,891 B1   4/2001   Nyren et al.
6,325,977 B1  12/2001   Theil
(Continued)

FOREIGN PATENT DOCUMENTS

CN       102713720    10/2012
CN       104372080     2/2015
(Continued)

OTHER PUBLICATIONS

Arkles, Hydrophobicity, Hydrophilicity and Silane Surface Modification, Paint & Coatings Industry, Available Online at: https://www.gelest.com/goods/pdf/Library/advances/HydrophobicityHydrophilicityandSilanes.pdf, Oct. 2006, 10 pages.
(Continued)

*Primary Examiner* — Cuong B Nguyen
(74) *Attorney, Agent, or Firm* — Kilpatrick Townsend & Stockton LLP

(57) ABSTRACT

A method for forming sequencing flow cells can include providing a semiconductor wafer covered with a dielectric layer, and forming a patterned layer on the dielectric layer. The patterned layer has a differential surface that includes alternating first surface regions and second surface regions. The method can also include attaching a cover wafer to the semiconductor wafer to form a composite wafer structure including a plurality of flow cells. The composite wafer structure can then be singulated to form a plurality of dies. Each die forms a sequencing flow cell. The sequencing flow cell can include a flow channel between a portion of the patterned layer and a portion of the cover wafer, an inlet, and an outlet. Further, the method can include functionalizing the sequencing flow cell to create differential surfaces.

19 Claims, 50 Drawing Sheets

Related U.S. Application Data

(60) Provisional application No. 62/669,890, filed on May 10, 2018, provisional application No. 62/560,585, filed on Sep. 19, 2017.

(51) Int. Cl.

| | | |
|---|---|---|
| *H01L 21/28* | (2006.01) | |
| *G01N 21/64* | (2006.01) | |
| *G01N 21/05* | (2006.01) | |
| *G01N 33/487* | (2006.01) | |
| *B01L 3/00* | (2006.01) | |

(52) U.S. Cl.
CPC ..... *G01N 21/6454* (2013.01); *G01N 33/48707* (2013.01); *H01L 21/02131* (2013.01); *H01L 21/02175* (2013.01); *H01L 21/02266* (2013.01); *H01L 21/02422* (2013.01); *H01L 21/28264* (2013.01); *H01L 29/20* (2013.01); *B01L 3/502715* (2013.01); *B01L 3/502784* (2013.01); *B01L 2300/0663* (2013.01); *B01L 2300/0816* (2013.01); *B01L 2300/0861* (2013.01); *B01L 2300/0877* (2013.01); *B01L 2300/165* (2013.01); *G01N 2021/058* (2013.01)

(58) Field of Classification Search
CPC ......... H01L 21/02422; H01L 21/28264; H01L 29/20; H01L 21/762; H01L 21/8238; H01L 27/14632; H01L 27/14643; H01L 27/14687; H01L 27/14689; H01L 27/14621; H01L 27/14627; H01L 27/14636; H01L 27/1464; H01L 27/14685; B01L 3/502707; B01L 3/502715; B01L 3/502784; B01L 2300/0663; B01L 2300/0816; B01L 2300/0861; B01L 2300/0877; B01L 2300/165; G01N 21/05; G01N 21/6454; G01N 33/48707; G01N 2021/058; G01N 21/27; G01N 21/6428; G01N 21/6486; G01N 33/4915; G01N 2021/6441; G01N 2021/6471; B01J 19/0046; B01J 2219/00619; C12Q 1/6874; C09D 143/02
See application file for complete search history.

(56) References Cited

U.S. PATENT DOCUMENTS

| | | | |
|---|---|---|---|
| 6,828,100 | B1 | 12/2004 | Ronaghi |
| 6,833,246 | B2 | 12/2004 | Balasubramanian |
| 6,911,345 | B2 | 6/2005 | Quake et al. |
| 7,883,869 | B2 | 2/2011 | Ju et al. |
| 7,910,354 | B2 | 3/2011 | Drmanac et al. |
| 7,972,820 | B2 | 7/2011 | Mayer |
| 8,105,771 | B2 | 1/2012 | Drmanac |
| 8,133,719 | B2 | 3/2012 | Drmanac et al. |
| 8,216,827 | B2 | 7/2012 | Pouteau et al. |
| 8,445,194 | B2 | 5/2013 | Drmanac et al. |
| 8,592,150 | B2 | 11/2013 | Drmanac et al. |
| 8,637,242 | B2 | 1/2014 | Shen et al. |
| 8,778,849 | B2 | 7/2014 | Bowen et al. |
| 8,906,320 | B1 | 12/2014 | Eltoukhy et al. |
| 9,222,132 | B2 | 12/2015 | Drmanac |
| 9,671,344 | B2 | 6/2017 | Staker |
| 10,784,103 | B2 | 9/2020 | Li et al. |
| 11,255,793 | B2 | 2/2022 | Zhong et al. |
| 2006/0084069 | A1 | 4/2006 | Chan et al. |
| 2006/0273430 | A1 | 12/2006 | Hua et al. |
| 2008/0029864 | A1* | 2/2008 | Pyo ............... B81C 1/00238 |
| | | | 257/678 |
| 2008/0081769 | A1 | 4/2008 | Hassibi |
| 2009/0111207 | A1 | 4/2009 | Choumane et al. |
| 2010/0204064 | A1 | 8/2010 | Cho |
| 2010/0277722 | A1 | 11/2010 | Kraiczek et al. |
| 2011/0045466 | A1 | 2/2011 | Lin et al. |
| 2011/0096157 | A1 | 4/2011 | Fine et al. |
| 2011/0172129 | A1 | 7/2011 | Lee et al. |
| 2012/0156100 | A1 | 6/2012 | Tsai et al. |
| 2012/0224050 | A1 | 9/2012 | Staker |
| 2012/0231830 | A1 | 9/2012 | Jeong et al. |
| 2012/0261830 | A1 | 10/2012 | Chu et al. |
| 2013/0116153 | A1 | 5/2013 | Bowen et al. |
| 2013/0293749 | A1 | 11/2013 | Vaartstra |
| 2014/0152801 | A1 | 6/2014 | Fine et al. |
| 2014/0272719 | A1 | 9/2014 | Liu et al. |
| 2014/0376069 | A1* | 12/2014 | Reinmuth ........ G02B 26/0841 |
| | | | 359/221.2 |
| 2015/0056097 | A1 | 2/2015 | Vaartstra |
| 2015/0079596 | A1 | 3/2015 | Eltoukhy et al. |
| 2015/0087534 | A1 | 3/2015 | Gormley et al. |
| 2015/0177150 | A1 | 6/2015 | Rothberg et al. |
| 2015/0279894 | A1 | 10/2015 | Cheng et al. |
| 2016/0064439 | A1 | 3/2016 | Or-Bach et al. |
| 2016/0133517 | A1 | 5/2016 | Delamarche et al. |
| 2016/0237488 | A1 | 8/2016 | Ke et al. |
| 2016/0338347 | A1 | 11/2016 | White et al. |
| 2018/0155782 | A1 | 6/2018 | Zhong |
| 2018/0195961 | A1 | 7/2018 | Eamey et al. |

FOREIGN PATENT DOCUMENTS

| | | |
|---|---|---|
| CN | 105980580 | 9/2016 |
| CN | 105980832 | 9/2016 |
| EP | 2221606 A2 | 8/2010 |
| EP | 2362418 A3 | 8/2011 |
| JP | 2004532397 A | 10/2004 |
| JP | 2007333497 A | 12/2007 |
| JP | 2009082675 A | 4/2009 |
| JP | 2010531994 A | 9/2010 |
| JP | 2011520111 A | 7/2011 |
| JP | 2013509618 A | 3/2013 |
| JP | 2013084747 A | 5/2013 |
| JP | 2013092393 A | 5/2013 |
| JP | 2015073070 A | 4/2015 |
| JP | 2015533503 A | 11/2015 |
| WO | 2009001988 A1 | 12/2008 |
| WO | 2011103497 A1 | 8/2011 |
| WO | 2014031157 A1 | 2/2014 |
| WO | 2014077783 A1 | 5/2014 |
| WO | 2015089092 A1 | 6/2015 |
| WO | 2016032562 A1 | 3/2016 |
| WO | 2018085642 A1 | 5/2018 |
| WO | 2018175341 A1 | 9/2018 |

OTHER PUBLICATIONS

Frank et al., "Image Artifacts in Backside Illumination CMOS Image Sensors Associated with Electrostatic Charge", Papers of the International Image Sensor Society, R18, 2019, pp. 1-3.

"Biosensor Based on a Microelectromechanical System Integrated with a Photodector", Toyohashi University of Technology, PhysOrg, Available online at https://phys.org/news/2014-03-biosensor-based-microelectromechanical-photodetector.html, Mar. 3, 2014, pp. 1-2.

Donato , "Implementation of Chemiluminescence and Color-Based Detection in Smartphone for Bioassays", ALMA DL University of Bologna Digital Library, Apr. 27, 2016, pp. 1-129.

Donato , "Implementation of Chemiluminescence and Color-Based Detection in Smartphone for Bioassays", Dissertation Thesis Date, University of Bologna, Apr. 27, 2016, pp. 1-2.

Drmanac et al., "Human Genome Sequencing Using Unchained Base Reads on Self-Assembling DNA Nanoarrays", Science, Reports, vol. 327, No. 5961, Jan. 1, 2010, pp. 78-81.

EP17867617.7, "Extended European Search Report", dated May 25, 2020, 11 pages.

PCT/US2017/059908, "International Preliminary Report on Patentability", dated May 16, 2019, 9 pages.

PCT/US2017/059908, "International Search Report and Written Opinion", dated Feb. 2, 2018, 18 pages.

(56) References Cited

OTHER PUBLICATIONS

PCT/US2018/023176, "International Preliminary Report on Patentability", dated Oct. 3, 2019, 9 pages.
PCT/US2018/023176, "International Search Report and Written Opinion", dated Jun. 13, 2018, 13 pages.
PCT/US2018/050437, "International Preliminary Reporton Patentability", dated Apr. 2, 2020, 10pages.
PCT/US2018/050437, "International Search Report and Written Opinion", dated Dec. 13, 2018, 14 pages.
PCT/US2018/050437, "Invitation to Pay Additional Feesand Partial Search Report", dated Oct. 15, 2009, 2 pages.
Ronaghi et al., "DNA Sequencing: A Sequencing Method Based on Real-Time Pyrophosphate", Science, vol. 281, Issue 2375, Jul. 17, 1998, pp. 363-365.
Seitz et al., "Chemiluminescence and Bioluminescence", Analytical Chemistry, vol. 46, No. 2, Feb. 1974, pp. 188-202.
Shendure et al., "Next-Generation DNA Sequencing", Nature Biotechnology, vol. 26, No. 10, Oct. 1, 2008, pp. 1135-1145.
EP18857916.3, "Extended European Search Report", dated May 7, 2021, 9 pages.
Deetlefs et al., Quill Ionic Liquids, Catalyst, Available Online at: https://www.stem.org.uk/system/files/elibrary-resources/legacy_files_migrated/36428-Catalyst_25_2_602.pdf, Dec. 2014, pp. 16-18.
Kedmi et al., The Systemic Toxicity of Positively Charged Lipid Nanoparticles and the Role of Toll-Like Receptor 4 in Immune Activation, Biomaterials, vol. 31, Issue 26, Sep. 2010, pp. 6867-6875.
Sobek et al., Analysis of Fluorescent Dyes Used for Labeling DNA in Microarray Experiments, Millipore Sigma, Available Online at: https://www.sigmaaldrich.com/IN/en/technical-documents/technical-article/genomics/gene-expression-and-silencing/analyzing-fluorescent-dye-dna-labeling, 2021, pp. 1-6.
U.S. Appl. No. 15/803,077, "Advisory Action", dated May 18, 2022, 4 pages.
AU2018237066, "First Examination Report", dated May 9, 2022, 5 pages.
CN201780068138.7, "Office Action", dated May 5, 2022, 4 pages, Translation of Substantive Objections of This Office Action on p. 1.
JP2019-552087, "Office Action", dated Mar. 8, 2022, 5 pages.

* cited by examiner

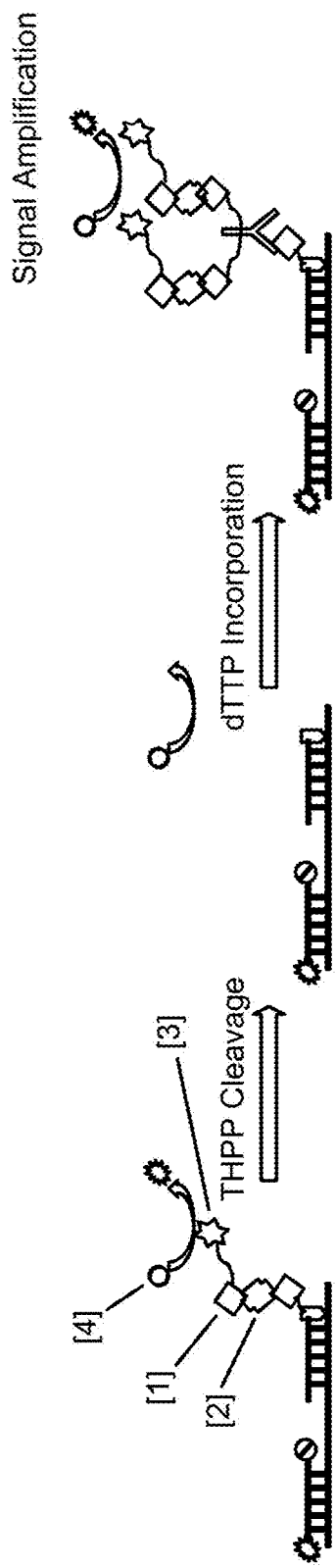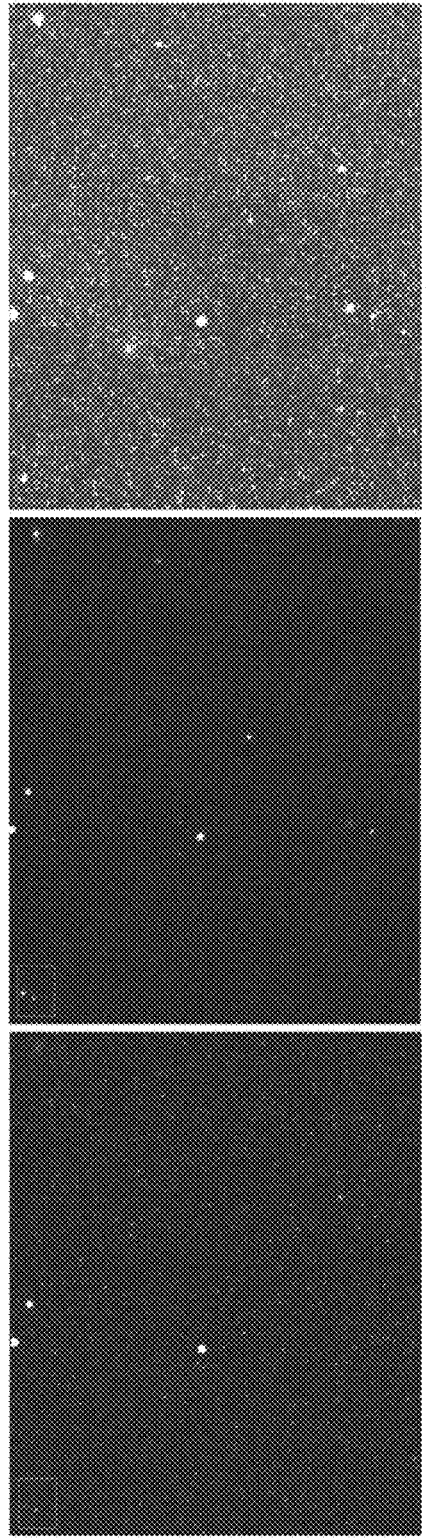
FIG. 43A  1st step dATP-Biotin image
FIG. 43B  2nd step (cleave) image
FIG. 43C  3rd step dTTP-Digoxin image

WAFER LEVEL SEQUENCING FLOW CELL FABRICATION

CROSS-REFERENCES TO RELATED APPLICATIONS

This application is a continuation application of U.S. patent application Ser. No. 16/128,120, filed Sep. 11, 2018, entitled "Wafer Level Sequencing Flow Cell Fabrication," which claims priority to U.S. Provisional Patent Application No. 62/560,585, filed Sep. 19, 2017, entitled "Wafer Level Sequencing Flow Cell Fabrication," and U.S. Provisional Patent Application No. 62/669,890, filed May 10, 2018, entitled "Wafer Level Sequencing Flow Cell Fabrication," all of which are commonly assigned and incorporated by reference in their entirety herein for all purposes.

FIELD

The present invention relates generally to a biosensor for biological or chemical analysis, and more specifically, to methods of forming sequencing flow cells including packaging at the wafer level.

BACKGROUND

High-throughput analysis of chemical and/or biological species is an important tool in the fields of diagnostics and therapeutics. Arrays of attached chemical and/or biological species can be designed to define specific target sequences, analyze gene expression patterns, identify specific allelic variations, determine copy number of DNA sequences, and identify, on a genome-wide basis, binding sites for proteins (e.g., transcription factors and other regulatory molecules). In a specific example, the advent of the human genome project required that improved methods for sequencing nucleic acids, such as DNA (deoxyribonucleic acid) and RNA (ribonucleic acid), be developed. Determination of the entire 3,000,000,000 base sequence of the haploid human genome has provided a foundation for identifying the genetic basis of numerous diseases.

High-throughput analysis, such as massively parallel DNA sequencing, often utilize flow cells, which contain arrays of chemicals and/or biological species available for analysis. Assay flow cells used as part of an overall system for biological assays include, in various configurations, a carrier in which an assay substrate may be provided, where a substantial portion of the assay substrate can be used for biochemical analysis, since the carrier component of the flow cell is designed to provide functionalities that in prior art systems were performed by the assay substrate itself. The flow cells may be used in automated systems and may be generally flat for imaging. Various configurations of the components of the flow cells minimize evaporation, yet allow for precise control of fluid intake and evacuation.

The manufacture and use of many current flow cells designs can be costly, and the flow cell design is often inefficient in the utilisation of functionalized surface area, decreasing the amount of data that can be obtained using the flow cell.

SUMMARY

Embodiments of the invention provide methods of wafer level chip packaging of a nanoarray flow cell for DNA sequencing applications. The wafer level packaging can substantially reduce the cost of the flow cell fabrication. In some embodiments, hard differential surfaces are formed on the wafers, which can be selectively functionalized for the DNB loading. Hard surfaces formed in the embodiments described here can withstand standard semiconductor wafer level fabrication and packaging processes without any sophisticated constraints, which can improve fabrication and chip packaging yield.

According to some embodiments, a method for forming sequencing flow cells can include providing a semiconductor wafer covered with a dielectric layer, and forming a patterned layer on the dielectric layer. The patterned layer has a differential surface that includes alternating first surface regions and second surface regions. The method can also include attaching a cover wafer to the semiconductor wafer to form a composite wafer structure including a plurality of flow cells. The composite wafer structure can then be singulated to form a plurality of dies. Each die forms a sequencing flow cell. The sequencing flow cell can include a flow channel between the patterned layer and the cover wafer, an inlet, and an outlet. The sequencing flow cell can include one or more first surface regions in the patterned layer and one or more second surface regions in the patterned layer. Further, the method can include functionalizing the sequencing flow cell to create differential surfaces.

In some embodiments of the above method, the first surface regions are hydrophilic surfaces and the second surface regions are hydrophobic surfaces. In some embodiments, the first surface regions hydrophobic are surfaces and the second surface regions are hydrophilic surfaces. In some embodiments, in a sequencing flow cell, either the first surface regions or the second surface regions are hydrophilic surfaces configured for receiving nucleic acid macromolecules for sequencing.

In some embodiments, the method also includes forming a plurality of through holes in the semiconductor wafer before attaching the cover wafer, the plurality of through holes configured as inlets and outlets for the flow cells.

In some embodiments, the method can also include comprising forming inlets and outlets in the cover wafer before attaching the cover wafer to the semiconductor wafer.

In some embodiments, the semiconductor wafer can also include a CMOS layer underlying the dielectric layer.

In some embodiments, forming a patterned layer can include forming a metal oxide layer overlying the dielectric layer on the semiconductor wafer, and patterning the metal oxide layer into a plurality of metal oxide regions. The metal oxide regions are configured to receive nucleic acid macromolecules.

In some embodiments, forming a patterned layer can include forming a metal oxide layer, forming a silicon oxide layer overlying the metal oxide layer, and patterning the silicon oxide layer. Regions of the metal oxide layer not covered by the silicon oxide layer are configured to receive a nucleic acid macromolecule.

In some embodiments, the method also includes forming a support structure on the semiconductor wafer before attaching the cover wafer to the semiconductor wafer.

In some embodiments, the method also includes bonding the cover wafer to the support structure.

In some embodiments, the cover wafer can include a glass wafer.

In some embodiments, the method can also include functionalizing the sequencing flow cell, wherein functionalizing the sequencing flow cell can include exposing the flow channel to materials supplied through the inlet and outlet.

In some embodiments, singulating the composite wafer structure can include separating the composite wafer structure into individual dies using a wafer cutting process.

According to some embodiments, a method for forming sequencing flow cells can include providing a semiconductor wafer having a dielectric layer overlying a complementary metal-oxide-semiconductor (CMOS) layer. The CMOS layer can include a photo sensing layer including a plurality of photodiodes, and an electronic circuit layer coupled to the photo sensing layer for processing sensed signals. The method can include forming a patterned layer on the dielectric layer, the patterned layer having alternate metal oxide regions and silicon oxide regions. The method can include attaching a glass wafer to the semiconductor wafer to form a composite wafer structure. The glass wafer can include a plurality of holes. The composite wafer structure includes a plurality of sequencing flow cells. Each sequencing flow cell can include a glass layer having holes configured as an inlet and an outlet of the sequencing flow cell. Each sequencing flow cell can include multiple metal oxide regions and silicon oxide regions, and a flow channel between the glass layer and the multiple metal oxide regions and silicon oxide regions. The composite wafer structure can be singulated to form a plurality of dies, each of which can include a sequencing flow cell.

In some embodiments of the above method, forming a patterned layer can include forming a metal oxide layer overlying the dielectric layer on the semiconductor wafer, and patterning the metal oxide layer into a plurality of metal oxide regions. The metal oxide regions are configured to receive nucleic acid macromolecules.

In some embodiments, forming a patterned layer can include forming a metal oxide layer, forming a silicon oxide layer overlying the metal oxide layer, and patterning the silicon oxide layer. Regions of the metal oxide layer not covered by the silicon oxide layer are configured to receive a nucleic acid macromolecule.

In some embodiments, the method also includes bonding the glass wafer to the semiconductor wafer. This bonding step can be used with various combinations of the steps of the method described herein.

In some embodiments, the method also includes functionalizing the sequencing flow cell, and functionalizing the sequencing flow cell can include exposing the sequencing flow cell to materials supplied through the inlet and outlet. This functionalization step can be used with various combinations of the steps described above.

According to some embodiments, a method for forming sequencing flow cells can include providing a semiconductor wafer covered with a dielectric layer, and forming a patterned layer on the dielectric layer. The patterned layer can have alternate metal oxide regions and oxide regions. The method can also include forming a plurality of through holes through the semiconductor wafer, and attaching a glass wafer to the semiconductor wafer to form a composite wafer structure. The composite wafer structure can then be singulated to form a plurality of dies, each die forming a sequencing flow cell. The method can also include functionalizing the sequencing flow cell. Each sequencing flow cell can include a glass layer, multiple metal oxide regions and oxide regions, and a flow channel between the glass layer and the multiple metal oxide regions and oxide regions. The metal oxide regions are configured to receive nucleic acid macromolecules, and through holes in the semiconductor wafer are configured as inlet and outlet of the sequencing flow cell.

In some embodiments of the above method, forming a patterned layer can include forming a metal oxide layer overlying the dielectric layer on the semiconductor wafer, and patterning the metal oxide layer into a plurality of metal oxide regions The metal oxide regions are configured to receive nucleic acid macromolecules.

In some embodiments, forming a patterned layer can include forming a metal oxide layer overlying the dielectric layer on the semiconductor wafer, forming a silicon oxide layer overlying the metal oxide layer, and patterning the silicon oxide layer. Regions of the metal oxide layer not covered by the silicon oxide layer are configured to receive a nucleic acid macromolecule.

In some embodiments, the method can also include bonding the glass wafer to the semiconductor wafer.

In some embodiments, the method can also include functionalizing the sequencing flow cell, wherein functionalizing the sequencing flow cell can include exposing the sequencing flow cell to materials supplied through the inlet and outlet to form hydrophilic surface regions and hydrophobic surface regions. This functionalization step can be used with various combinations of the steps described above.

According to some embodiments, a method for forming a device structure having differential surfaces includes providing a substrate and forming a surface layer having alternating first thin film regions and second thin film regions on the substrate. The method includes forming a first covering layer selectively on the first thin film regions by exposing the surface layer to a first material. The method also includes form a second covering layer selectively on the second thin film regions and not on the first thin film regions, by exposing the surface layer to a second material. The method further includes selecting the first material and the second material to adjust hydrophobicity of the first covering layer and the second covering layer.

In some embodiments of the above method, the first thin film regions comprise a metal or metal oxide material, the metal oxide material including one or more of anodized aluminum ($Al_2O_3$), tantalum oxide ($Ta_2O_5$), niobium oxide ($Nb_2O_5$), zirconium oxide ($ZrO_2$), and titanium oxide ($TiO_2$).

In some embodiments, the first material can include phosphonic acid or phosphate.

In some embodiments, the second thin film regions comprise a silicon oxide.

In some embodiments, the second material can include silane.

In some embodiments, forming a first covering layer on the first thin film regions can include an annealing process after exposing the surface layer to a first material.

In some embodiments, the annealing process can include 5 to 15 minutes in an inert ambient at 70° to 90° C.

In some embodiments, the first covering layer is hydrophilic, and the second covering layer are hydrophobic.

In some embodiments, the first covering layer has positive charges, and the second covering layer has negative charges.

In some embodiments, forming the surface layer can include forming an silicon oxide layer, forming a metal oxide layer overlying the silicon oxide layer, and patterning the metal oxide layer to remove portions of the metal oxide layer to form a plurality of metal oxide regions, and to expose a plurality of silicon oxide regions. The first thin film regions include the plurality of metal oxide regions, and the second thin film regions include the plurality of silicon oxide regions.

In some embodiments, forming the surface layer can include forming a metal oxide layer, forming a silicon oxide layer overlying the metal oxide layer, and patterning the silicon oxide layer to remove portions of the silicon oxide layers to form a plurality of silicon oxide regions, and to expose a plurality of metal oxide regions. The first thin film regions include the plurality of metal oxide regions, and the second thin film regions include the plurality of silicon oxide regions.

In some embodiments, forming the first covering layer can include exposing a metal oxide region to polyvinylphosphonic acid (PVPA) to form a hydrophilic covering layer.

In some embodiments, forming the first covering layer can include exposing a metal oxide region to 12-Hydroxy dodecyl phosphate, (OH-DDPO$_4$) in a SAM (self assembled monolayer) to form a hydrophiliic hydrophilic covering layer.

In some embodiments, forming the first covering layer can include exposing a metal oxide region ammonium salt of hydroxy dodecyl phosphate to form a hydrophobic covering layer.

In some embodiments, forming the first covering layer can include exposing a metal oxide region to a mixture of 12-Hydroxy dodecyl phosphate, (OH-DDPO$_4$) and of hydroxy dodecyl phosphate to form a first covering layer of adjustable hydrophobicity.

In some embodiments, forming the second covering layer can include exposing a silicon oxide region to a hydrophobic silane to form a hydrophobic covering layer.

In some embodiments, the hydrophobic silane can include fluorinated Alkyl-Silanes or dialkyl-Silanes.

In some embodiments, forming the second covering layer can include exposing a silicon oxide region to a hydrophilic silane to form a hydrophilic covering layer.

In some embodiments, the hydrophilic silane can include hydroxyakyl terminated silane.

In some embodiments, the substrate can include a bare semiconductor substrate.

In some embodiments, the substrate can include a semiconductor substrate including CMOS circuitry and backside illumination (BSI) sensors.

In some embodiments, the substrate can include a glass material.

According to some embodiments, a device structure having differential surfaces includes a substrate and a surface layer having alternating first thin film regions and second thin film regions on the substrate. The device includes a first covering layer selectively formed on the first thin film regions, and a second covering layer selectively on the second thin film regions and not on the first thin film regions. The first covering layer and the second covering layer are configured to have different hydrophobicity.

The foregoing, together with other features and embodiments, will become more apparent upon referring to the following specification, claims, and accompanying drawings.

BRIEF DESCRIPTION OF THE DRAWINGS

FIGS. 2-7 are cross-sectional views illustrating various stages of wafer scale packaging of sequencing flow cells according to an embodiment of the invention. The processes described in FIGS. 2-7 are carried out on wafer 100 described in FIG. 1.

FIG. 2 is a cross-sectional view of a wafer structure 200 having differential surface patterning over the wafer structure 100 of FIG. 1 according to some embodiments of the invention.

FIG. 3 is a cross-sectional view illustrating a wafer structure 300 having a cover structure disposed over the wafer structure 200 of FIG. 2 according to some embodiments of the invention.

FIG. 5 is a cross-sectional view of a plurality of individual flow cell dies 500 after a wafer singulation process at an intermediate stage of manufacture of sequencing flow cells according to embodiments of the invention.

FIG. 6 is a cross-sectional view of a plurality of individual flow cell dies 600 after a functionalization process is applied to the flow cell dies 500 of FIG. 5 at an intermediate stage of manufacture of sequencing flow cells according to embodiments of the invention.

FIG. 7 is a cross-sectional view illustrating a plurality of individual flow cell dies 700 after a sample loading process in the sequencing flow cells 600 of FIG. 6 according to embodiments of the invention.

FIG. 8 is a cross-sectional view of a wafer structure 800 having differential surface patterning over the wafer structure 100 of FIG. 1 according to some embodiments of the invention.

FIG. 9 is a cross-sectional view illustrating a wafer structure 900 having a cover structure disposed over the wafer structure 800 of FIG. 8 according to some embodiments of the invention.

FIG. 10 is a cross-sectional view illustrating a wafer structure 1000 with backside packaging on the wafer structure 900 of FIG. 9 according to some embodiments of the invention.

FIG. 11 is a cross-sectional view of a plurality of individual flow cell dies 1100 after a wafer singulation process at an intermediate stage of manufacture of sequencing flow cells according to embodiments of the invention. The singulation process illustrated in FIG. 10 is similar to the process described above in connection with FIG. 5.

FIG. 12 is a cross-sectional view of a plurality of individual flow cell dies 1200 after a functionalization process is applied to the flow cell dies 1100 of FIG. 11 at an intermediate stage of manufacture of sequencing flow cells according to embodiments of the invention.

FIG. 13 is a cross-sectional view illustrating a plurality of individual flow cell dies 700 after a sample loading process in the sequencing flow cells 1200 of FIG. 12 according to embodiments of the invention. The sample loading process illustrated in FIG. 13 is similar to the process described above in connection with FIG. 7.

FIG. 14 is a cross-sectional view of a wafer structure 1400 having differential surface patterning over a bare wafer 301 according to some embodiments of the invention.

FIG. 15 is a cross-sectional view illustrating a wafer structure 1500 having through holes formed in the wafer structure 1400 of FIG. 14 according to some embodiments of the invention.

FIG. 16 is a cross-sectional view illustrating a wafer structure 1600 having a cover structure disposed over the wafer structure 1500 of FIG. 15 according to some embodiments of the invention.

FIG. 17 is a cross-sectional view of a plurality of individual flow cell dies 1700 after a wafer singulation process at an intermediate stage of manufacture of sequencing flow cells according to embodiments of the invention.

FIG. 18 is a cross-sectional view of a plurality of individual flow cell dies 1800 after a functionalization process is applied to the flow cell dies 1700 of FIG. 17 according to embodiments of the invention. The functionalization process illustrated in FIG. 18 is similar to the process described above in connection with FIG. 6.

FIG. 19 is a cross-sectional view illustrating a plurality of individual flow cell dies 1900 after a sample loading process in the sequencing flow cells 1800 of FIG. 18 according to embodiments of the invention.

FIG. 20 is a cross-sectional view of a wafer structure 2000 having differential surface patterning over a bare wafer according to some embodiments of the invention.

FIG. 21 is a cross-sectional view illustrating a wafer structure 2100 having through holes formed in the wafer structure 2000 of FIG. 20 according to some embodiments of the invention.

FIG. 22 is a cross-sectional view illustrating a wafer structure 2200 having a cover structure disposed over the wafer structure 2100 of FIG. 21 according to some embodiments of the invention.

FIG. 23 is a cross-sectional view of a plurality of individual flow cell dies 2300 after a wafer singulation process at an intermediate stage of manufacture of sequencing flow cells according to embodiments of the invention.

FIG. 24 is a cross-sectional view of a plurality of individual flow cell dies 2400 after a functionalization process is applied to the flow cell dies 2300 of FIG. 23 according to embodiments of the invention.

FIG. 25 is a cross-sectional view illustrating a plurality of individual flow cell dies 2500 after a sample loading process in the sequencing flow cells 2400 of FIG. 2 according to embodiments of the invention.

FIG. 27A shows a thin film layer formed on a substrate.

FIG. 27B shows a second thin film layer formed on a first thin film layer.

FIG. 27C shows a patterned mask layer formed on the second thin film layer.

FIG. 27D shows a cross-sectional view of a device structure having alternating thin film regions.

FIG. 27E shows a first covering layer selectively formed on the first thin film region.

FIG. 27F shows a second covering layer selectively formed on the top surfaces of the second thin film regions to form a device structure having differential surface regions.

FIG. 28A shows a cross-sectional view of a device structure having alternating surface regions of first thin film layer and second thin film layer.

FIG. 28B shows a first covering layer selectively formed on the first thin film regions.

FIG. 28C shows a second covering layer selectively formed on the top surfaces of the second thin film regions to form a device structure having differential surface regions.

FIGS. 43A-43C are photographic images showing signals from DNBs at numerous spots on the array in a BSI CMOS chip at various stages of a multiple step sequencing according to some embodiments.

DETAILED DESCRIPTION

Embodiments of the invention provide methods of wafer level chip packaging of a flow cell for DNA sequencing applications. The flow cell can include one or more nucleic acid arrays comprising template nucleic acids for sequencing. In one approach the arrays are DNA nanoball (DNB) nanoarrays. In another approach the arrays comprise clusters of template nucleic acids, each cluster comprising amplicons of a single template molecule.

The wafer level packaging according to an aspect of the invention can substantially reduce the cost of the flow cell fabrication. In some embodiments, hard differential surfaces are etched on the wafers, which can be selectively functionalized for the DNB loading. Hard surfaces formed in the embodiments described here can withstand standard semiconductor wafer level fabrication and packaging processes without any sophisticated constraints, which can improve fabrication and chip packaging yield.

I. Wafer Level Fabrication of Flow Cell on CMOS Wafer

Figure 1:
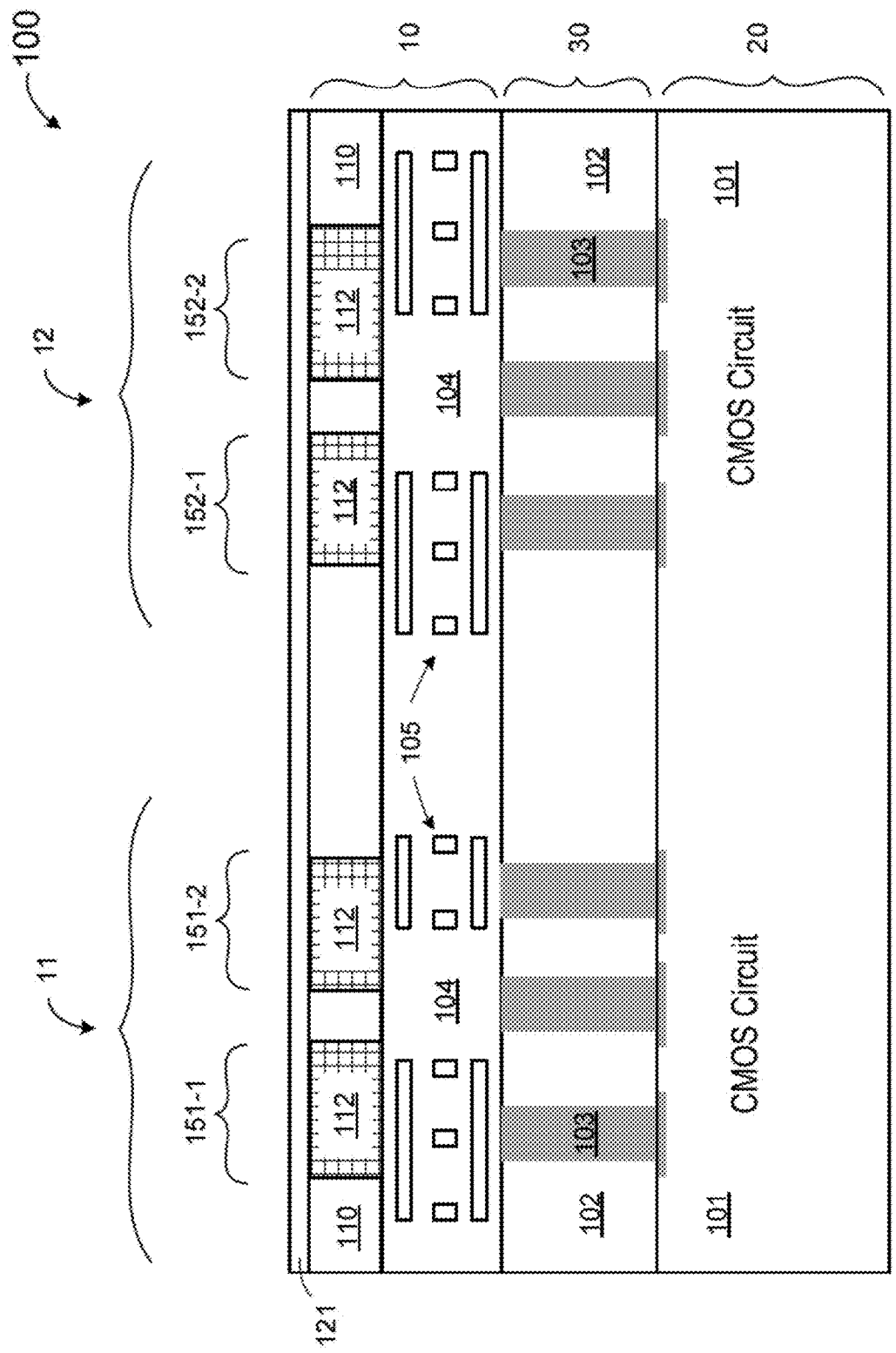
FIG. 1 is a cross-sectional view of a semiconductor wafer 100 at an intermediate stage of manufacture of sequencing flow cells according to embodiments of the invention.

FIG. 1 is a cross-sectional view of a semiconductor wafer 100 at an intermediate stage of manufacture of sequencing flow cells according to embodiments of the invention. In the manufacturing of semiconductor-based sequencing cells, a wafer can have thousands of dies, and each die represents a portion of the wafer that will be fabricated into a sequencing chip including an array of multiple cells, for example, hundreds of cells or more. For simplicity, FIG. 1 only shows regions 11 and 12 in semiconductor wafer 100, which are designed for two flow cells in two separate dies, and each region is shown to have only two cell areas, which are illustrated in FIG. 1. Region 11 includes cell areas 151-1 and 151-2, and region 12 includes cell areas 152-1 and 152 2.

As shown in FIG. 1, semiconductor wafer 100 includes CMOS image sensor layer 10, CMOS processing circuitry layer 20, and stacking layer 30. In a stacked technology, CMOS image sensor layer 10 and CMOS processing circuitry layer 20 can be fabricated separately and then joined together in a 3-D stacked device with a stacking interface layer 30.

CMOS image sensor layer 10 includes light sensing components 112, e.g., photodiodes, formed in a semiconductor 110. Semiconductor layer 110 may be made of any suitable material, such as, for example, silicon, III-V group on silicon, graphene-on-silicon, silicon-on-insulator, combinations thereof, and the like. Although described herein with respect to photodiodes 110, it is contemplated that any suitable light sensing component may be used. The photodiodes 110 may be configured to convert measured light into current. Photodiodes 110 may include the source and drain of an MOS transistor (not shown) that may transfer the current to other components, such as other MOS transistors. The other components may include a reset transistor, a current source follower or a row selector for transforming the current into digital signals, and the like. Although described as being dielectric, it is contemplated that the dielectric layer may include any suitable electrically insulating material.

CMOS image sensor layer 10 also includes metal wirings 105 formed in a dielectric layer 104. The metal wirings 115 may include interconnections for integrated circuit materials and external connections.

CMOS processing circuitry layer 20 is shown as a silicon substrate layer 101 for simplicity. However, it is understood that CMOS processing circuitry layer 20 can include CMOS circuits needed for the sequencing operation. For example, CMOS processing circuitry layer 20 can include circuitry for image process, signal processing, and control functions for sequencing operation, and external communication.

As shown in FIG. 1, CMOS image sensor layer 10 is configured for backside illumination (BSI). CMOS image sensor layer 10 and CMOS processing circuitry layer 20 can be fabricated separately and then joined together in a 3-D stacked device with a stacking layer 30. Stacking layer 30 can include a dielectric layer 102 and vias 103 formed in dielectric layer 102. Vias 103 are used for connecting CMOS image sensor layer 10 and CMOS processing circuitry layer 20.

FIG. 1 also shows a passivation layer 121 overlying CMOS image sensor layer 10. Passivation layer 121 may be deposited by conventional semiconductor processing techniques (e.g., low temperature plasma chemical vapor deposition, PECVD, sputtering, ALD, spin coating, dipping, etc.) on the substrate layer 110 and the photodiodes 112. The passivation layer 121 may include any suitable protective material. For example, the passivation layer 121 may include materials such as silicon nitride, silicon oxide, other dielectric material, or combinations thereof, and the like. The passivation layer 121 may act as an etch stop for later etching steps, as described further herein. The passivation layer 121 may alternatively or additionally act to protect the active device (i.e., the backside illumination CMOS sensor). The passivation layer 121 may alternatively or additionally act to protect photodiodes 112 from wear caused by frequent use. The passivation layer 121 may be transparent.

Discrete areas, sometimes called "spots" or wells (not shown), at which analyte molecules may be localized or immobilized may be formed over or in the first passivation layer 121. Chemical or biological samples may be placed on or over the discrete areas for analysis. In general, for DNA sequencing, the biological samples comprise a DNA sequencing library. DNBs or other members of a DNA sequencing library, or a clonal population thereof, are localized in the discrete areas.

In some embodiments, CMOS image sensor layer 10 may be adapted for detecting an optical signal (e.g., fluorescent or chemiluminescent emission) from a corresponding array of biomolecules, where individual biomolecules may be positioned over (e.g., in spots or wells) one or more photodiodes such that the one or more photodiodes receive light from the biomolecule. As used herein chemiluminescence includes bioluminescence, such as bioluminescence produced by luciferase reporters.

FIGS. 2-7 are cross-sectional views illustrating various stages of wafer scale packaging of sequencing flow cells according to an embodiment of the invention. The processes described in FIGS. 2-7 are carried out on wafer 100 described in FIG. 1.

Figure 2:
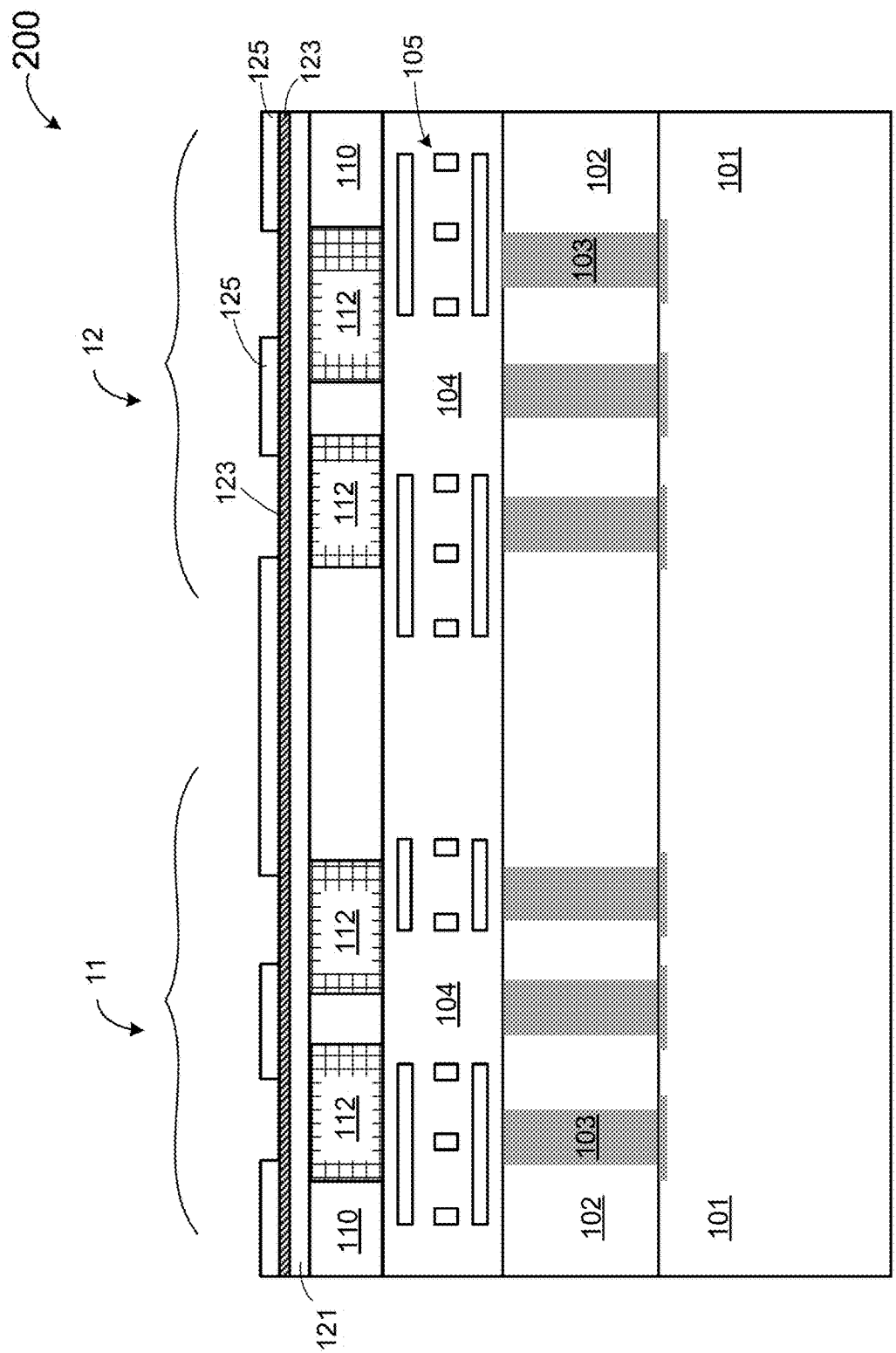

FIG. 2 is a cross-sectional view of a wafer structure 200 having differential surface patterning over the wafer structure 100 of FIG. 1 according to some embodiments of the invention. FIG. 2 shows alternately exposed regions of a first material 123 and a second material 125 are formed overlying dielectric layer 121 of wafer 100 illustrated in FIG. 1. In the embodiment of FIG. 2, a metal-containing layer 123 may be deposited by conventional semiconductor processing techniques on the passivation layer 121 (e.g., by sputtering, e-beam evaporation, thermal evaporation, ALD, etc.). Metal-containing Layer 123 may include any suitable metal or metal oxide material. For example, the layer 123 may include materials such as tungsten, titanium, titanium nitride, silver, tantalum, tantalum oxide, hafnium, chromium, platinum, tungsten, aluminum, gold, copper, combinations or alloys thereof, and the like. Layer 123 may be opaque to incident light and/or, when present, to excitation light.

In FIG. 2, regions of layer 125 may be formed by depositing a dielectric material and patterned using a photolithography and etching process. The dielectric material 125 may include any suitable protective material. For example, the dielectric layer 121 may include materials such as silicon nitride, silicon oxide, other electrically insulating material, or combinations thereof, and the like. Dielectric layer 125 may be deposited by conventional semiconductor processing techniques (e.g., low temperature plasma chemical vapor deposition, PECVD, sputtering, ALD, spin coating, dipping, etc.) over the metal-containing layer 123.

Next, the deposited dielectric layer 121 may be patterned using a conventional photolithography and etching process. The process includes forming a patterned mask on the deposited dielectric layer 121, etching the deposited dielectric layer 121, and removing the patterned mask. After the photolithography and etching process, regions of metal-containing layer 123 not covered by dielectric layer 125 are exposed. These exposed areas of metal-containing layer 123 may form a spot or well into which biological or chemical samples may be placed, as described further herein.

Figure 3:
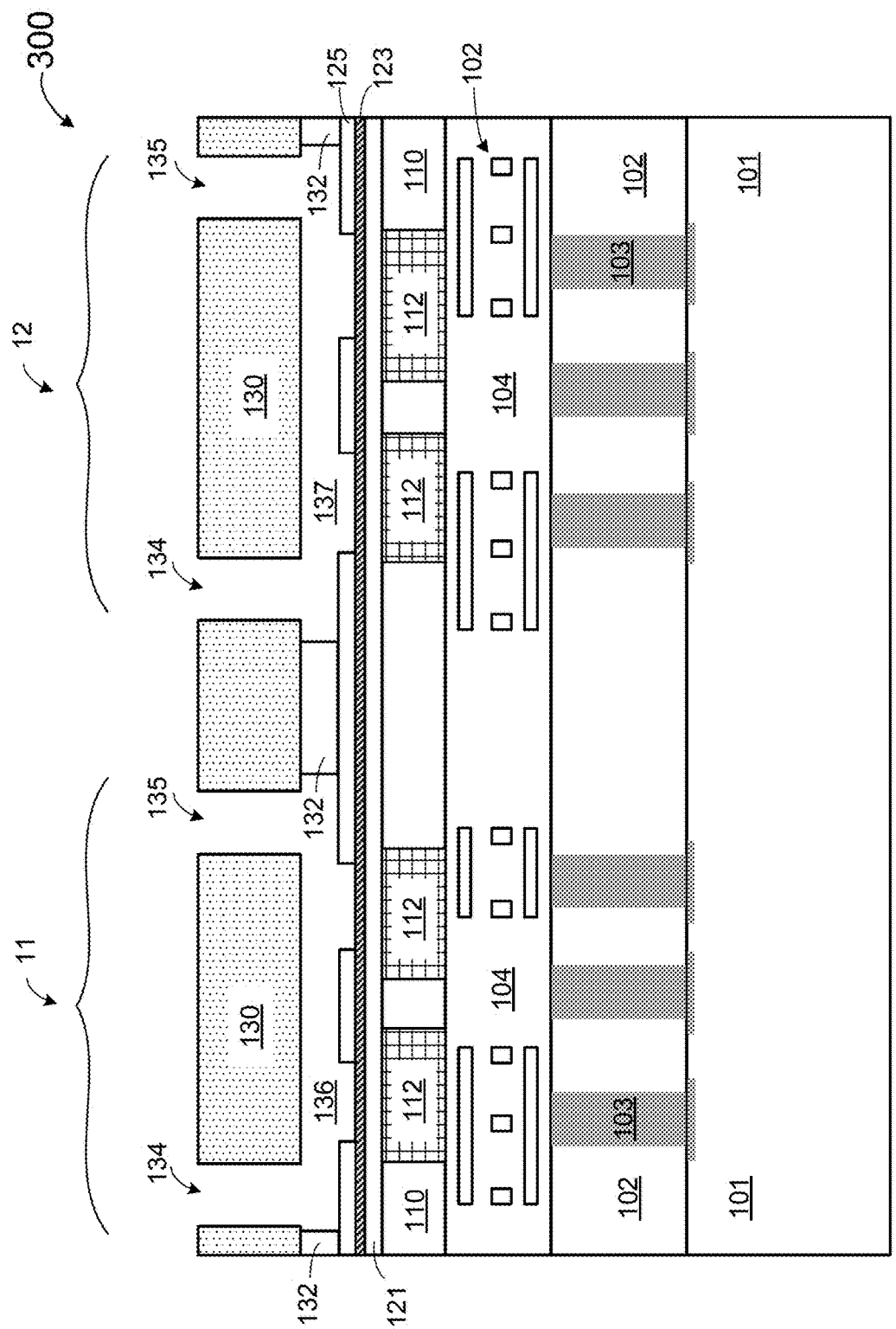

FIG. 3 is a cross-sectional view illustrating a wafer structure 300 having a cover structure disposed over the wafer structure 200 of FIG. 2 according to some embodiments of the invention. The cover structure 130 can be supported by support structures or spacers 132 disposed over the dielectric layer 125. In some embodiments, cover structure 130 can be a glass wafer having the same dimension as the wafer structure 200 of FIG. 2. Cover structure 130 can also be any suitable substrate such as glass materials, plastic materials, silica, semiconductor, etc. Cover structure 130 can be prefabricated with one or more inlets 134 and one or more outlets 135 for each chip area 151 and 152.

Cover structure 130 can be bonded to the wafer structure 200 of FIG. 2 using Support structures or spacers 132. Support structures 132 can help to define assay regions on the assay substrate. Support structures 132 can be made of a suitable dielectric insulating material. In some embodiments, the cover structure may have a thickness less than about 300 microns such that said coverslip can accommodate high numeric aperture optics with minimal distortion as a viewing window for said assay regions. The cover structure can be positioned on the spacers so as to support said coverslip with minimal warping and to form one or more flow channels.

The flow cell components can be directly connected via the use of an adhesive. The adhesive is preferably introduced to a surface that provides optimal adhesion between the various flow cell components. The adhesive may be a solid, such as a tape, or may be an adhesive applied as a liquid or gel that can subsequently be dried or cured into a solid form. The solid adhesive may provide height to the flow channels by virtue of its thickness. A liquid or gel can also contain solid or semi-solid particles of a specific size (e.g., glass or plastic beads) that will remain a particular thickness when the liquid or gel adhesive dries, thus defining the height of the flow channels. In these cases, the adhesive material can form the support structure.

Figure 4A:
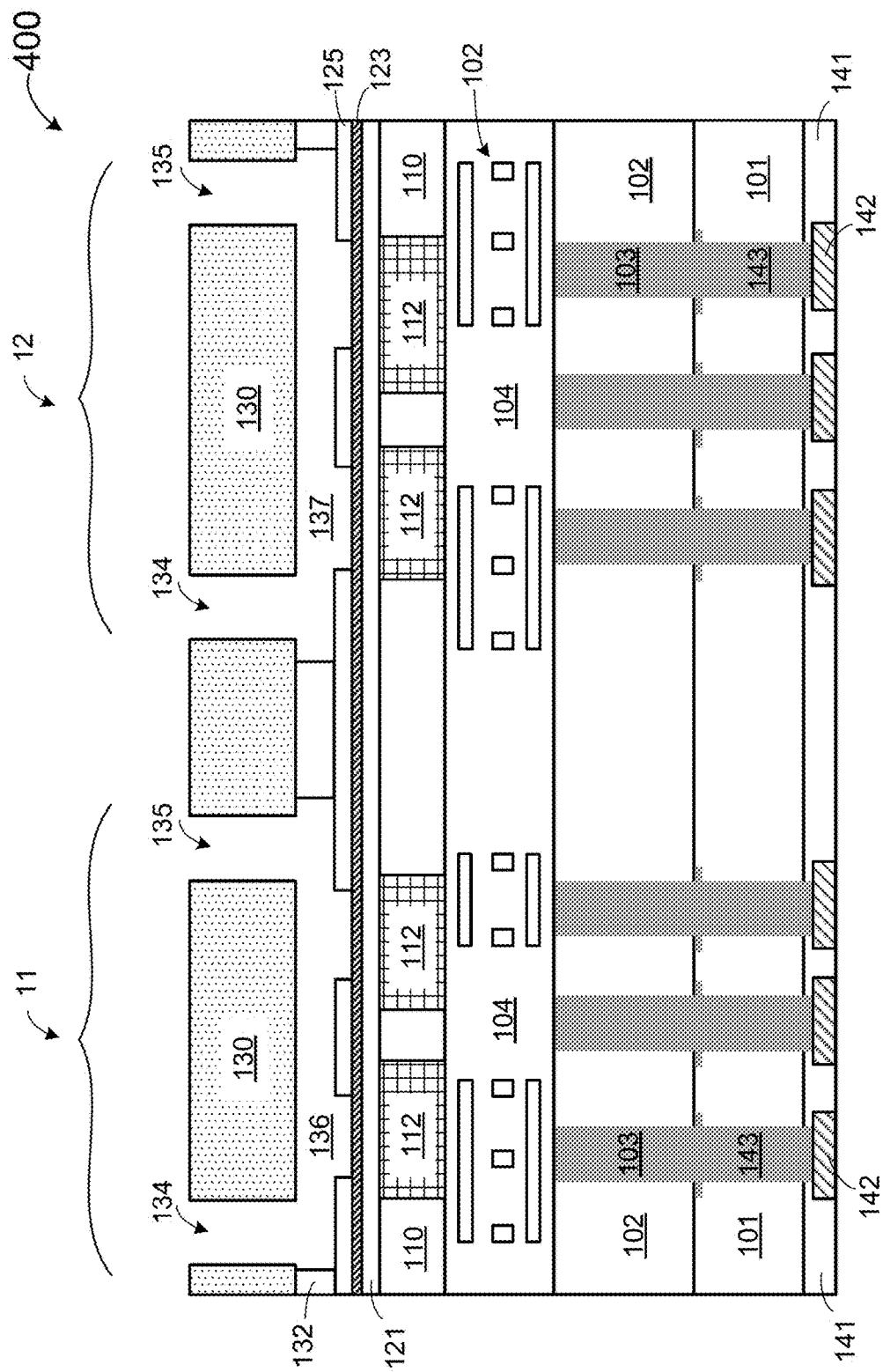
FIG. 4A is a cross-sectional view illustrating a wafer structure 400 with backside packaging on the wafer structure 300 of FIG. 3 according to some embodiments of the invention.
Figure 7:
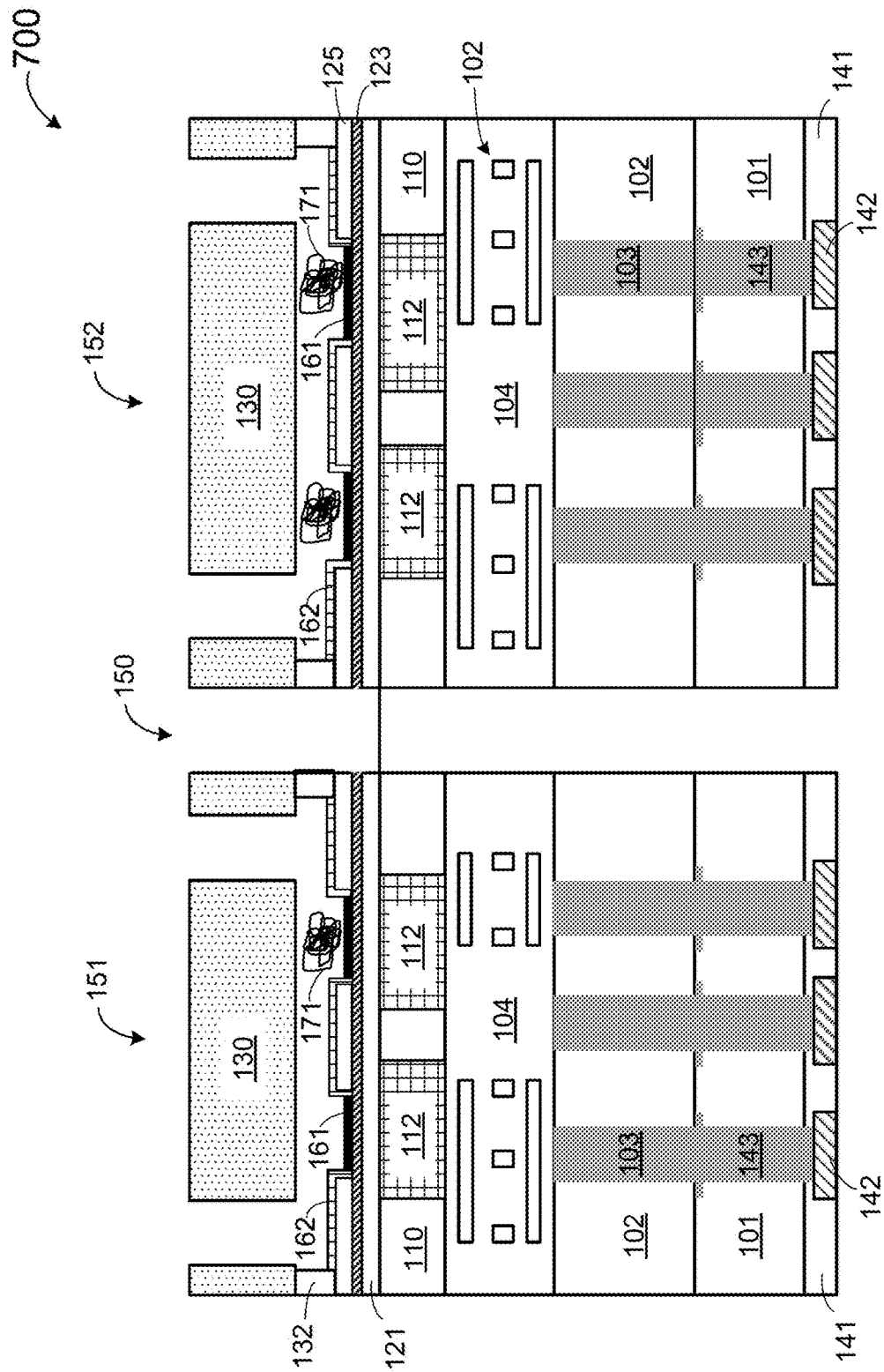

FIG. 4A is a cross-sectional view illustrating a wafer structure 400 with backside packaging on the wafer structure 300 of FIG. 3 according to some embodiments of the invention. FIG. 4A illustrates a backside packaging process at an intermediate stage of manufacture of sequencing flow cells according to embodiments of the invention. Wafer level packaging can include TSV (through-silicon via)/RDL (redistribution layer) passive interposer. The interposer can support chips on its bottom-side as well as on its top-side for 3-D integrated circuit integration. As shown in FIG. 7, through-silicon vias 143 can be formed in silicon wafer 101, which includes CMOS circuits as described above in connection with FIG. 1. Further, metal routing layer 141 and bonding pads can be formed on the backside contacts to allow communication with external circuits and systems.

Figure 4B:
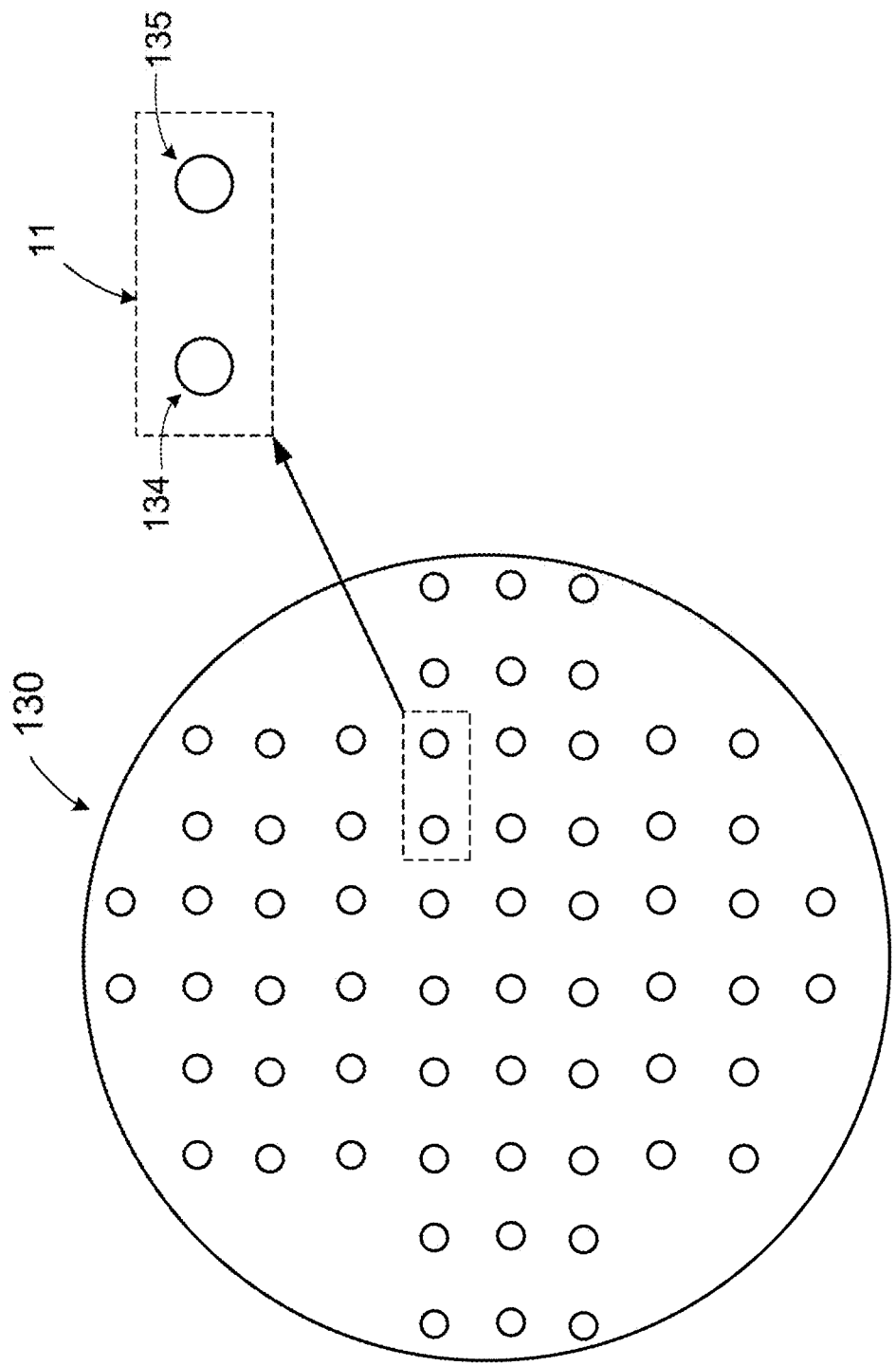
FIG. 4B is a top view of the cover wafer of FIG. 4A according to some embodiments of the invention.

FIG. 4B is a top view of the cover wafer of FIG. 4A according to some embodiments of the invention. As shown in FIG. 4B, cover wafer 130 includes multiple premade holes, which will form the inlets and outlets of the flow cells. As shown in a magnified view of an area 11 designated as a die for a flow cell, there is an inlet hole 134 and an outlet hole 135.

Figure 5:
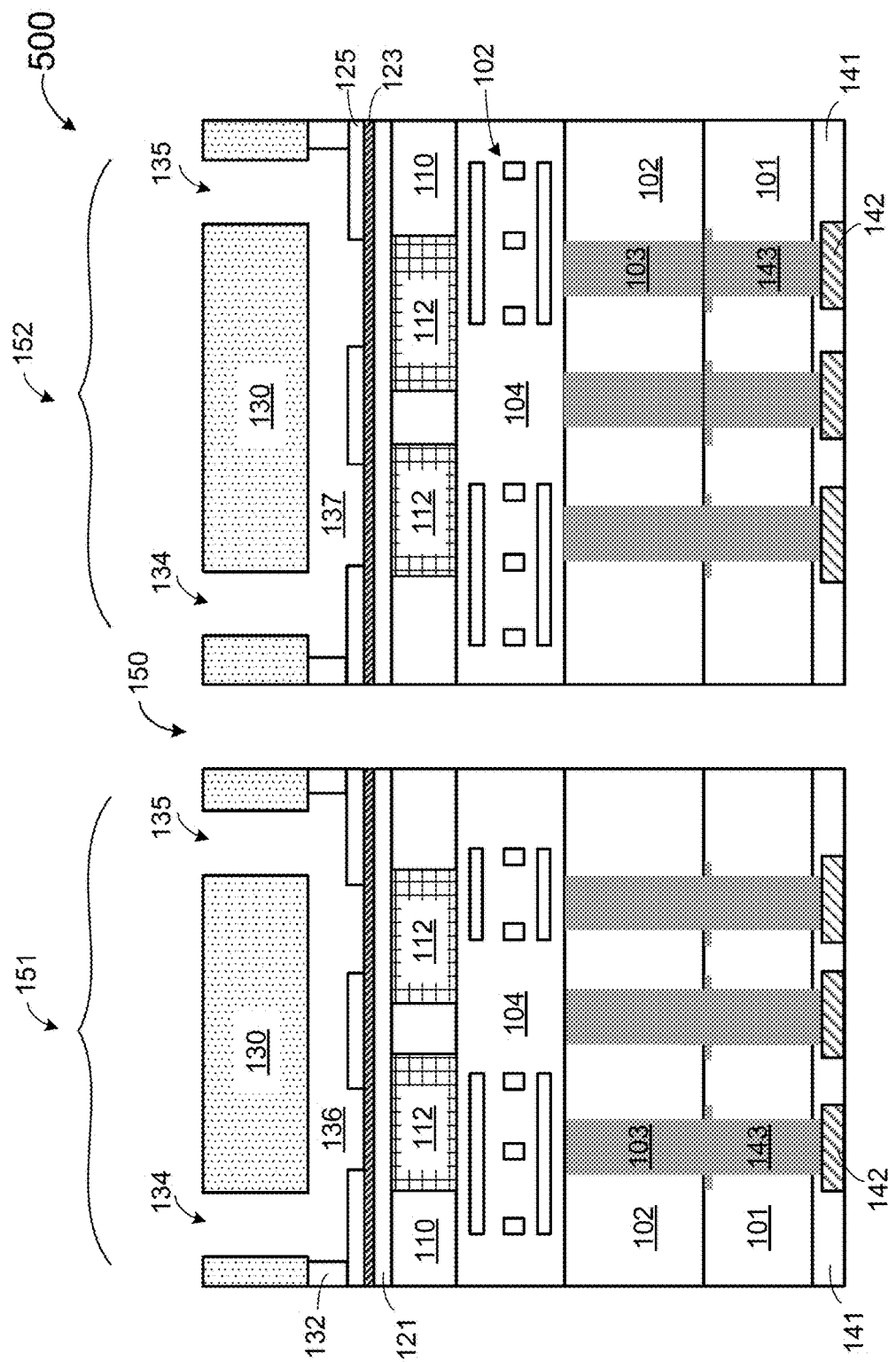

FIG. 5 is a cross-sectional view of a plurality of individual flow cell dies 500 after a wafer singulation process at an intermediate stage of manufacture of sequencing flow cells according to embodiments of the invention. The wafer structure 400 in FIG. 4 can include hundreds or thousands of flow cell structures. In between the flow cell structure, a thin non-functional spacing, also known as a scribe line, is reserved, where a dicing saw can cut the wafer without damaging the structures and circuits. The width of the scribe can be very small, typically around 100 μm. A very thin and accurate saw is therefore needed to cut the wafer into pieces. The dicing can be performed with a water-cooled circular saw with diamond-tipped teeth. In FIG. 5, the wafer structure in FIG. 4 is cut or diced into multiple dies or chips in a singulation process. Each individual die can contain a single flow cell, such as flow cells 151 and 152 separated by a spacing 150, in FIG. 5.

Figure 6:
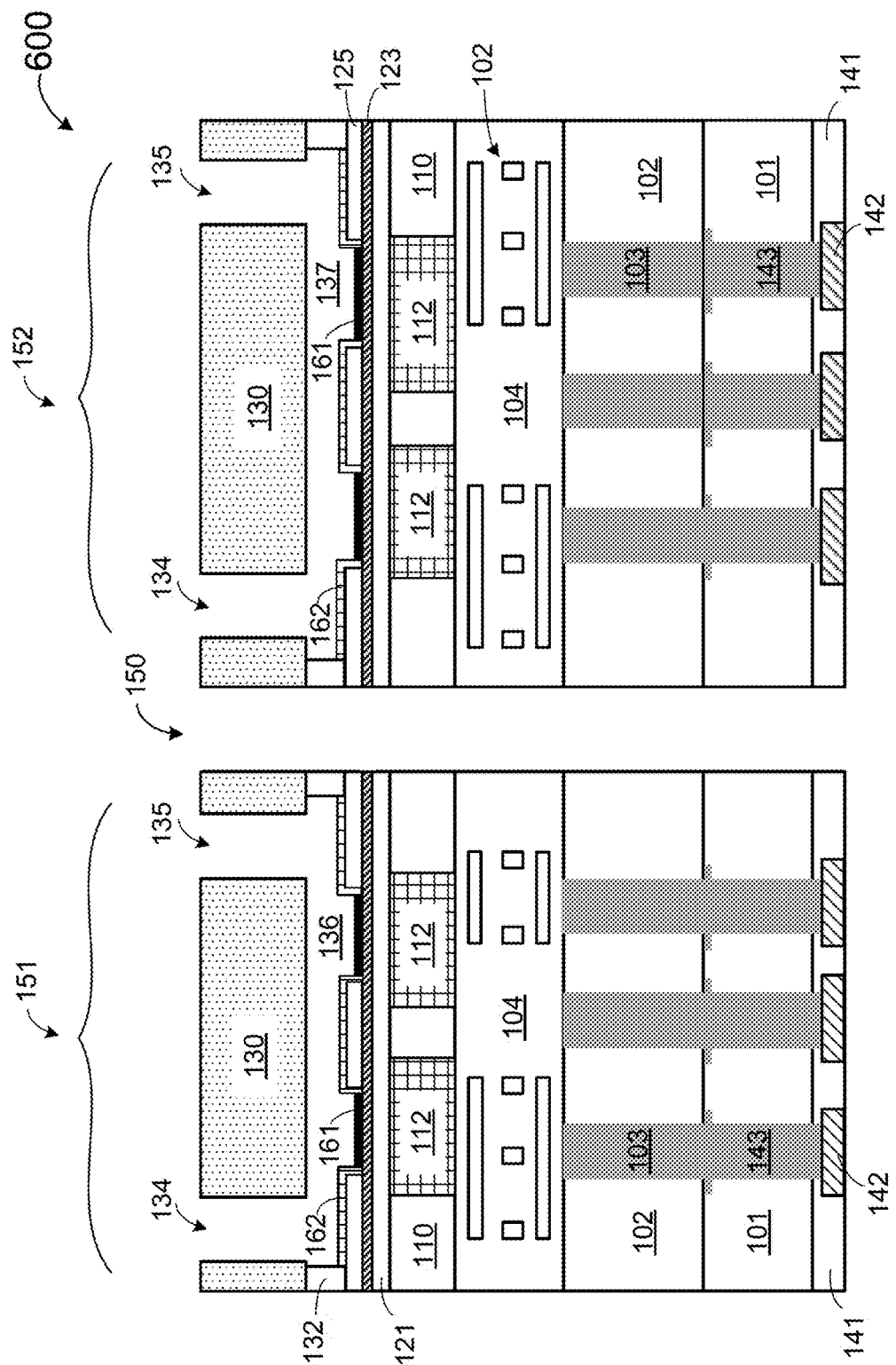

FIG. 6 is a cross-sectional view of a plurality of individual flow cell dies 600 after a functionalization process is applied to the flow cell dies 500 of FIG. 5 at an intermediate stage of manufacture of sequencing flow cells according to embodiments of the invention. For example, a first surface layer 161 and a second surface layer 162, which has properties different from the first surface layer, may be selectively applied based on the differential surfaces of the metal-containing layer 123 and the dielectric layer 125, respectively. The first and second surface layers have different properties, resulting in an array of spots or wells comprising a bottom surface comprising the first surface layer, separated by areas comprising the second surface layer. In some embodiments, macromolecules (e.g., polynucleotides, DNBs, proteins, etc.) of interest preferentially associate with the first surface layer compared with the second surface layer.

The first surface layer 161 may be formed by exposing the flow channels 136 and 137 to a suitable material supplied through the inlet 134 and outlet 135. The first surface layer 161 may also be selectively applied to the metal-containing layer 123 based on its surface properties. For example, the first surface layer 161 may be of such a material that it may bond to and/or be attracted to the metal-containing layer 123. In some embodiments the first surface layer does not bind or adhere to, or is repelled by, the dielectric layer 125. It will be recognized that the term "surface layer" is not intended to ascribe any particular structure or dimensions.

The first surface layer 161 may include any suitable material that adheres or binds the metal-containing material 123. In one approach, the first surface layer 161 is produced by application of a phosphate compound that binds metal, including without limitation, inorganic phosphate, phosphoric acid, organic phosphate compounds such as hexamethyl tetraphosphate, hexamthethylphosphoramide, combinations thereof, and the like.

In some embodiments, the second surface layer 162 may include a material that repels biological or chemical analytes of interest. For example, the second surface layer 162 may include a material that has a negative charge, thus repelling negatively charged biological or chemical samples. In some embodiments, the second surface layer 162 may be hydrophobic. Those of ordinary skill in the art will recognize that combinations (e.g., pairwise combinations) of metals and the second surface layer can be selected and optimized for particular purposes.

In FIG. 6, the second surface layer 162 may be selectively applied to the dielectric layer 125 based on the surface properties of the dielectric layer. For example, the second surface layer 162 may be of such a material that it may bond to and/or be attracted to the dielectric layer 125, but does not bond to or adhere to the first surface layer 161 which covers metal-containing layer 123. The second surface layer 162 may be applied by coating or treating the exposed portions of the dielectric layer 125 with a second material. In one approach, both the exposed dielectric layer 125 and metal-containing layer 123 regions covered by the first surface layer 161 are exposed to the second material, which adheres only on the dielectric layer. The second surface layer 162 may be formed by exposing the flow channels 136 and 137 to a suitable material supplied through the inlet 134 and outlet 135. In one approach the second surface layer 162 is produced by application of silane or a silane compound, including without limitation, 3-aminopropyl-methyldiethoxysilane, aminopropyltrimethoxysilane, 3-aminopropyltriethoxysilane, etc.

In some embodiments, the first surface layer 161 may include a material that attracts biological or chemical samples. For example, the first surface layer 161 may include a material that has a positive charge, thus attracting negatively charged biological or chemical samples. In some embodiments, the first surface layer 161 may be hydrophilic. Those of ordinary skill in the art will recognize that combinations of the first surface layer and the second surface layer can be selected and optimized for particular purposes.

It will be recognized that the term "surface layer" is not intended to limit the first and second surface layers to any particular method of application or structure. As noted, different properties of the first and the second surface layers may be selected to differentially retain target macromolecule(s), e.g., DNA macromolecules. It will also be recognized that the first and/or second surface layers may be functionalized such that the functionalized surface has a property that results in differential retention of target macromolecule(s). For illustration, after application of the first and second surface layers a DNA binding molecule (e.g., oligonucleotide) with affinity to the second surface layers, but not to the first surface layers, may be applied to cover second surface layer 162. In some embodiments, the second surface layer 162 can be a functionalized surface on which a single nucleic acid molecule is amplified.

Thus, a structure may be created in which a first surface layer is present in protruding regions, and a second surface layer is present in recessed regions between protruding portions. The recessed regions may form spots or wells into which biological or chemical samples may be placed. It will be recognized that the term "first surface layer" or "second surface layer" may refer to the material applied to the surface as well as the material retained on the surface (e.g., the latter may differ from the former by evaporation of a solvent; by a reaction with the surface material, and the like). It is further noted that the functionalization process described here in connection with FIG. 6 can be performed in other steps of the flow cell formation process. For example, the functionalization process can be performed after the differential surface patterning process described in connection with FIG. 2, or after the disposition of the cover wafer described in connection with FIG. 3, or after the backside packaging process described in connection with FIG. 4.

FIG. 7 is a cross-sectional view illustrating a plurality of individual flow cell dies 700 after a sample loading process in the sequencing flow cells 600 of FIG. 6 according to embodiments of the invention. Biological or chemical samples 171 can be introduced into the flow channels by flowing a liquid through the inlets and outlets of the flow channels. Embodiments of the invention are not limited to any particular method of introduction. In some embodiments, the biological or chemical samples 171 may be attracted to or bind to the first surface layer 161, while being repelled by the second surface layer 162.

The biological or chemical samples may include any of a number of components. For example, a sample may contain nucleic acid macromolecules (e.g., templates, DNA, RNA, etc.), proteins, and the like. The sample may be analyzed to determine a gene sequence, DNA-DNA hybridization, single nucleotide polymorphisms, protein interactions, peptide interactions, antigen-antibody interactions, glucose monitoring, cholesterol monitoring, and the like.

As discussed above, in some embodiments the biomolecule is a nucleic acid, such as DNA. See U.S. Pat. Nos. 8,778,849; 8,445,194; 9,671,344; 7,910,354; 9,222,132; 6,210,891; 6,828,100; 6,833,246; 6,911,345, and Pat. App. Pub. No. 2016/0237488, herein incorporated by reference in their entireties. Without limitation, the DNA biomolecule may be a DNA nanoball (single stranded concatemer) hybridized to labeled probes (e.g., in DNB sequencing by ligation or cPAL methods) or to complementary growing strands (e.g., in DNB sequencing by synthesis methods) or both; or a single DNA molecule (e.g., in single molecule sequencing); or to a clonal population of DNA molecules, such as is created in bridge PCR-based sequencing. Thus, reference to "a biomolecule", "a DNA macromolecule" or "a nucleic acid macromolecule" may encompass more than one molecule (e.g., a DNB associated with multiple growing complementary strands or a DNA cluster comprising clonal population of hundreds or thousands of DNA molecules). Exemplary methods for making DNBs (e.g., DNB libraries)

and for making arrays of discrete spaced apart regions separated by inter-regional areas are well known in the art. See, for example, U.S. Pat. Nos. 8,133,719; 8,445,196; 8,445,197; and 9,650,673, herein incorporated by reference in their entireties. In some embodiments DNBs or other macromolecules are immobilized on discrete spaced apart regions, or spots, through attractive noncovalent interactions (e.g., Van der Waal forces, hydrogen bonding, and ionic interactions). In some embodiments discrete spaced apart regions comprise functional moieties (e.g., amines). In some embodiments discrete spaced apart regions comprise capture oligonucleotides attached thereto, for binding template DNAs (e.g., DNBs). Generally the discrete spaced apart regions are arranged in a rectilinear pattern, however, regular arrays with other arrangements (e.g., concentric circles of regions, spiral patterns, hexagonal patterns, and the like) may be used.

In some embodiments, the nucleic acid macromolecules may be amplicons of genomic DNA fragments or a cDNA library. As used herein, an "amplicon" may be the product of amplification of a nucleic acid molecule, typically a fragment of genomic DNA or a cDNA library. Methods of amplification include, but are not limited to, rolling circle amplification, as described, for example, in U.S. Pat. No. 8,445,194 (herein incorporated by reference in its entirety), or bridge polymerase chain reaction (PCR), as described, for example, in U.S. Pat. No. 7,972,820, herein incorporated by reference in its entirety. The amplification may be performed before the nucleic acid is contacted with the biosensor, or in situ, as described, for example, in U.S. Pat. No. 7,910,354, herein incorporated by reference in its entirety.

For example, a biological sample, such as a DNA macromolecule, oligonucleotide, or nucleotide, associated with a fluorescent or chemiluminescent dye, may be placed above a photodiode 117. In the case of fluorescence, the dye may be illuminated by excitation light from an excitation light source. The excitation light may correspond to any suitable type or intensity of light, including, for example, visible light, infrared (IR), ultraviolet (UV), and the like. The excitation light may also come from any suitable source, such as light emitting diodes (LEDs), lamps, lasers, combinations thereof, and the like. When the dye is illuminated with excitation light at a certain wavelength, the biological sample may absorb the light, then emit light of a different wavelength. For example, the biological sample may absorb excitation light having a 450 nm wavelength, but emit light with a 550 nm wavelength. In other words, fluorescent light of a characteristic wavelength may be emitted when the dye is illuminated by light of a characteristic different wavelength (i.e., the excitation light source). Because excitation light is used to measure fluorescence, however, it must be filtered out in order to take accurate measurements at the photodiode 117.

In the case of chemiluminescence, no excitation light source is needed for the photodiodes 112 to detect emitted light. Instead, the biological sample may emit light due to a chemical or enzymatic reaction that may occur between the biological sample and the chemiluminescent dye (or other solution), causing light to be emitted due to breaking or forming chemical bonds (e.g., the action of a luciferase protein on a luciferin substrate).

For both fluorescence and chemiluminescence, the photodiodes 117 may detect the intensity of the emitted light and transform it into an electronic signal based on the intensity of the light that may be provided to an external device via metal wiring 105. The external device may correlate the electronic signal to a particular wavelength and brightness, based on the electronic signal.

In some embodiments, the active spot or well on the surface of the biosensor and the nucleic acid macromolecule may be mutually configured such that each spot binds only one nucleic acid macromolecule. This may be achieved, for example, by contacting the surface with amplicons that correspond in size to the active spot (e.g., an amplicon having a diameter that is effectively as large or larger than the diameter of the active spot). See U.S. Pat. No. 8,445,194, herein incorporated by reference in its entirety. Alternatively, the active spot can be chemically adapted to bind a single DNA fragment, which may then be amplified to fill a larger region at and around the original binding site.

Some embodiments of the invention may be used to determine different labels corresponding to different wavelengths of light. The labels may be, for example, fluorescent, chemiluminescent or bioluminescent labels. For example, in gene sequencing (or DNA sequencing), embodiments of the invention may be used to determine the precise order of nucleotide bases within a nucleic acid macromolecule (e.g., a strand of DNA). The nucleotide bases may be labeled with a specific fluorescent label (e.g., adenine (A), guanine (G), cytosine (C), or thymine (T)). Alternatively, one color, two color, or three color sequencing methods, for example, may be used.

With respect to fluorescence, each of the nucleotide bases may be determined in order by successively exciting the nucleic acid macromolecule with excitation light. The nucleic acid macromolecule may absorb the excitation light and transmit an emitted light of a different wavelength onto a biosensor as described herein. The biosensor may measure the wavelength of emitted light and intensity received by the photodiode. Each nucleotide (e.g., fluorescently labeled nucleotide), when excited by excitation light of a certain wavelength and/or intensity, may emit a certain wavelength of light and/or intensity into the photodiode, allowing identification of the presence of a particular nucleotide base at a particular position in the nucleic acid macromolecule. Once that particular nucleotide base has been determined, it may be removed from the nucleic acid macromolecule, such that the next successive nucleotide base may be determined according to a similar process.

A nucleic acid macromolecule may be labeled with one or more different fluorescent, chemiluminescent, or bioluminescent labels before or after attaching to the biosensor for any purpose. For example, the nucleic acid macromolecule may be hybridized with a labeled oligonucleotide probe or amplification primer. Alternatively, the nucleic acid macromolecule may be hybridized with a non-labeled oligonucleotide, which may then be ligated to a labeled probe, or extended using labeled nucleotide analogs. By way of illustration, the labeling may be done for the purpose of characterizing the nucleic acid macromolecule (for example, the presence of a single nucleotide polymorphism (SNP) associated with a disease), or for nucleic acid sequencing of all or a part of the nucleic acid macromolecule, as described above. DNA sequencing by probe hybridization is described, for example, in U.S. Pat. No. 8,105,771, herein incorporated by reference in its entirety. Sequencing by anchor probe ligation is described, for example, in U.S. Pat. No. 8,592,150, herein incorporated by reference in its entirety. Sequencing by synthesis is described, for example, in U.S. Pat. No. 7,883,869, herein incorporated by reference in its entirety. In general, sequencing by synthesis is a method in which nucleotides are added successively to a free 3' hydroxyl group provided by a sequencing primer hybridized to a template sequence, resulting in synthesis of a nucleic acid chain in the 5' to 3' direction. In one approach, another exemplary type of SBS, pyrosequencing techniques may be employed (Ronaghi et al., 1998, Science 281:363).

In some embodiments, the biosensor may be reversibly coupled to a flow cell (not shown). The nucleic acid macromolecule may be attached to the biosensor by contacting the biosensor with a liquid sample in the flow cell. The flow cell may include one or more flow channels that are in fluid communication with the reaction sites. In one example, the biosensor may be fluidically and electrically coupled to a bioassay system. The bioassay system may deliver reagents to the reaction sites according to a predetermined protocol and perform imaging events. For example, the bioassay system may direct solutions to flow along the reaction sites. The solution may include four types of nucleotides having the same or different fluorescent labels. In some embodiments, the bioassay system may then illuminate the reaction sites using an excitation light source. The excitation light may have a predetermined wavelength or wavelengths. The excited fluorescent labels may provide emission signals that may be detected by the photodiodes 117.

A user may prepare for sequencing by contacting a biosensor according to described embodiments with nucleic acid amplicons, or with a nucleic acid that is subsequently amplified, such that the nucleic acid macromolecule binds and is retained by the active spots or wells, and excess nucleic acid macromolecule may be washed away. The nucleic acid macromolecules may be contacted beforehand or in situ with a labeled reagent. The biosensor may then be operated as described herein to determine light emitted on or around nucleic acid macromolecules on the array. The light may be quantified, or it may be sufficient to determine in a binary fashion which of the nucleic acid macromolecules on the surface have been labeled with labels that emit at a particular wavelength. Different probes or different nucleic acid analogs may be used concurrently that have labels that emit light at different wavelengths, for example, to determine different bases at a particular position in the sequence, or to sequence multiple locations.

Although described herein with respect to a backside illumination CMOS sensor, it is contemplated that embodiments of the invention may be similarly applied to a frontside illumination CMOS sensor. Further, it is contemplated that embodiments of the invention may similarly apply to any suitable biosensor, such as those biosensors described in U.S. Provisional Pat. App. No. 62/416,813, filed Nov. 3, 2016, which is herein incorporated by reference in its entirety.

II. Alternative Wafer Level Fabrication of Flow Cell on CMOS Wafer

FIGS. 8-13 are cross-sectional views illustrating various stages of wafer scale packaging of sequencing flow cells according to another embodiment of the invention. The processes described in FIGS. 8-13 can be carried out on wafer 100 described in FIG. 1.

Figure 8:
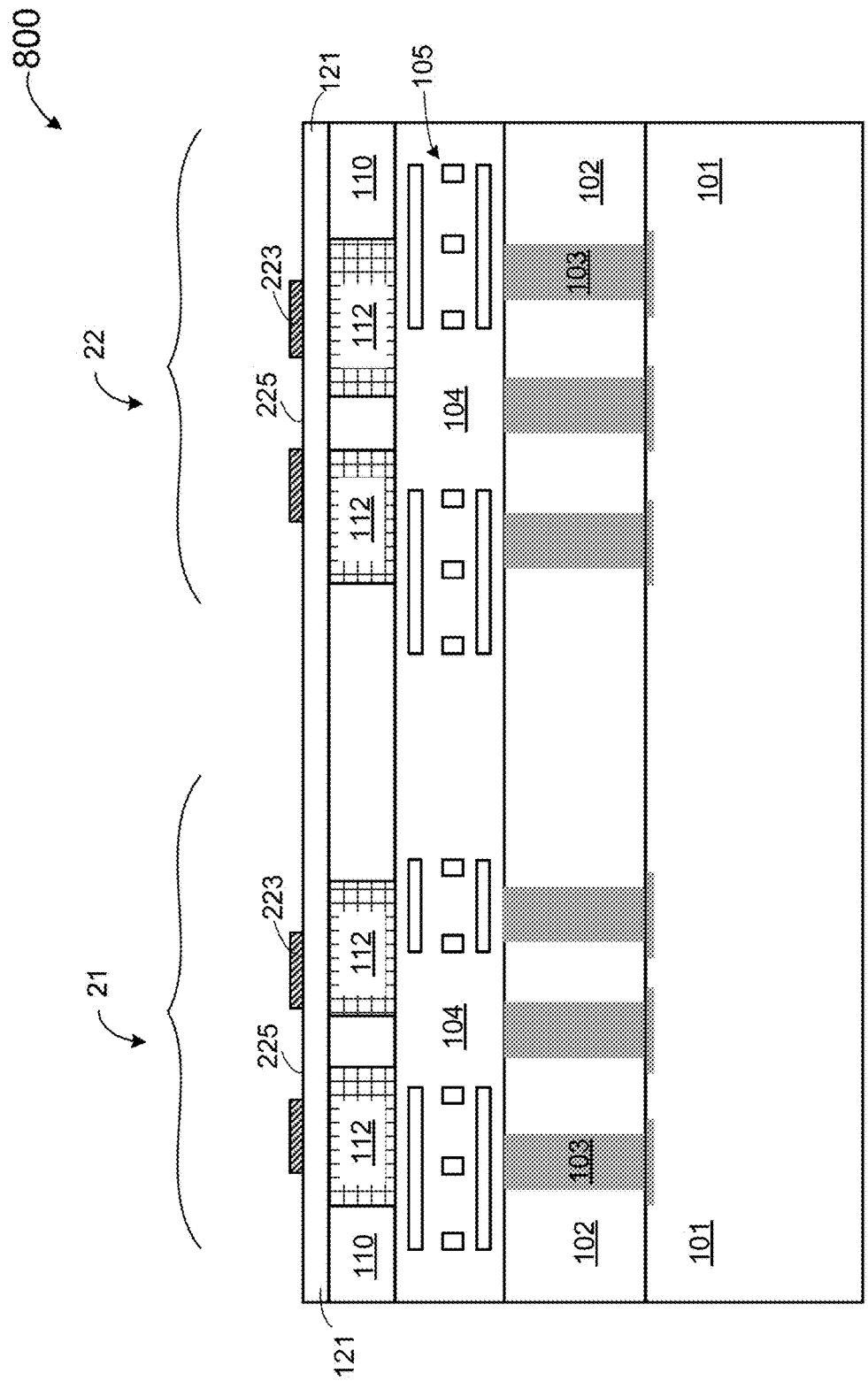
FIGS. 8-13 are cross-sectional views illustrating various stages of wafer scale packaging of sequencing flow cells according to another embodiment of the invention. The processes described in FIGS. 8-13 can be carried out on wafer 100 described in FIG. 1.

FIG. 8 is a cross-sectional view of a wafer structure 800 having differential surface patterning over the wafer structure 100 of FIG. 1 according to some embodiments of the invention. Wafer structure 800, similar to wafer structure 200 of FIG. 2, only shows regions 21 and 22 in semiconductor wafer 800, which are designed for two flow cells in two separate dies. Wafer structure 800 also has alternately exposed regions of a first material and a second material that are formed overlying wafer 100 illustrated in FIG. 1. However, in wafer structure 200, the dielectric regions 125 are formed over the metal-containing regions 123, whereas in wafer structure 800, the metal-containing regions 223 are formed over the dielectric regions 225. In FIG. 8, dielectric regions 225 can be formed using the dielectric layer 121 from wafer 200 of wafer structure 200. Dielectric regions 225 also can be formed in another dielectric layer deposited over dielectric layer 121. The metal-containing regions 223 can be formed by a deposition and patterning process similar to that described above in connection with FIG. 2.

Figure 9:
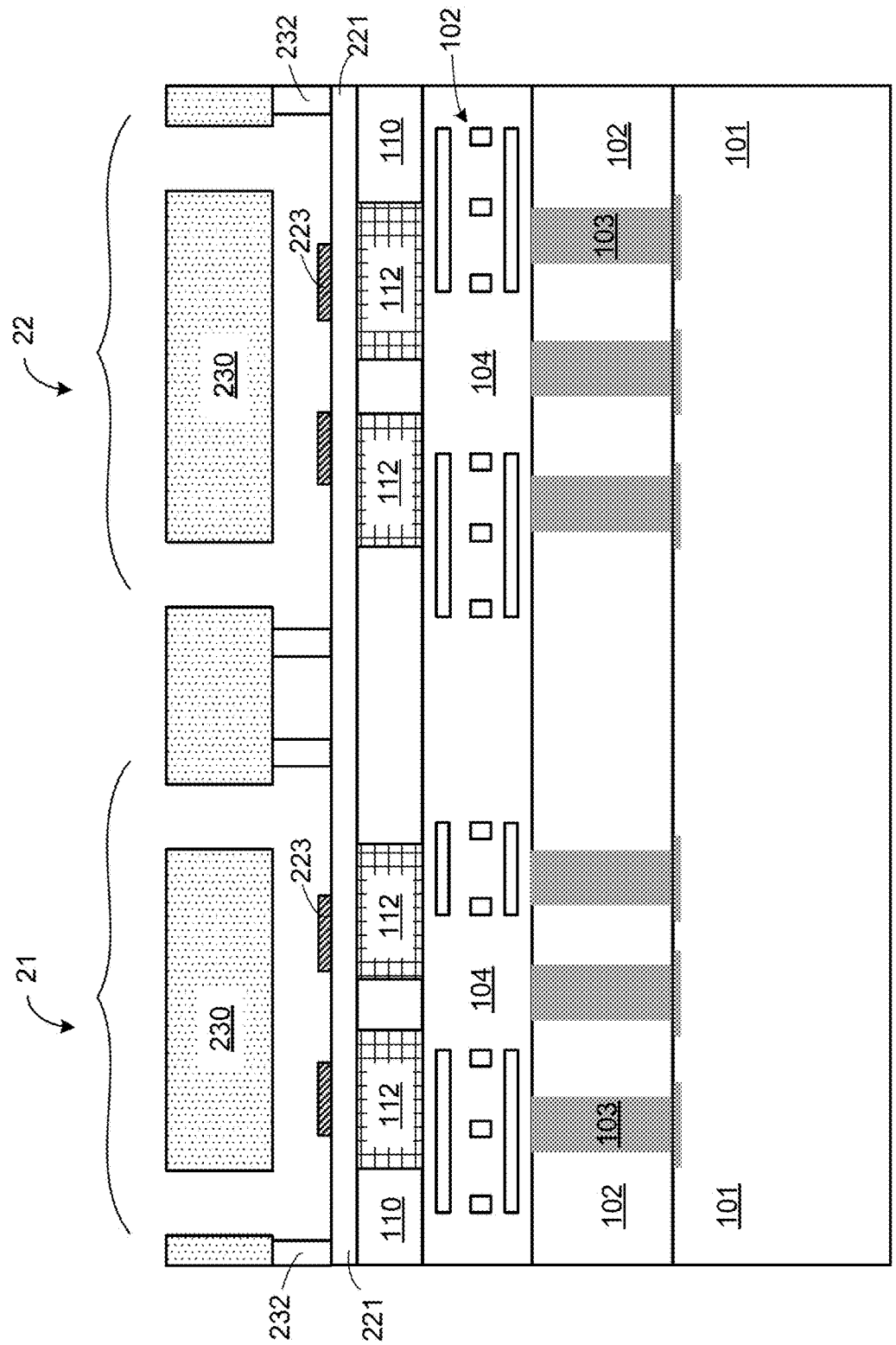

FIG. 9 is a cross-sectional view illustrating a wafer structure 900 having a cover structure disposed over the wafer structure 800 of FIG. 8 according to some embodiments of the invention. Cover structure 230 and support structures 232 can be formed using similar processes as described above in connection with FIG. 3. In FIG. 9, flow channels are formed under the cover structures, and each flow cell can have one or more inlets and one or more outlets, similar to wafer structure 300.

Figure 10:
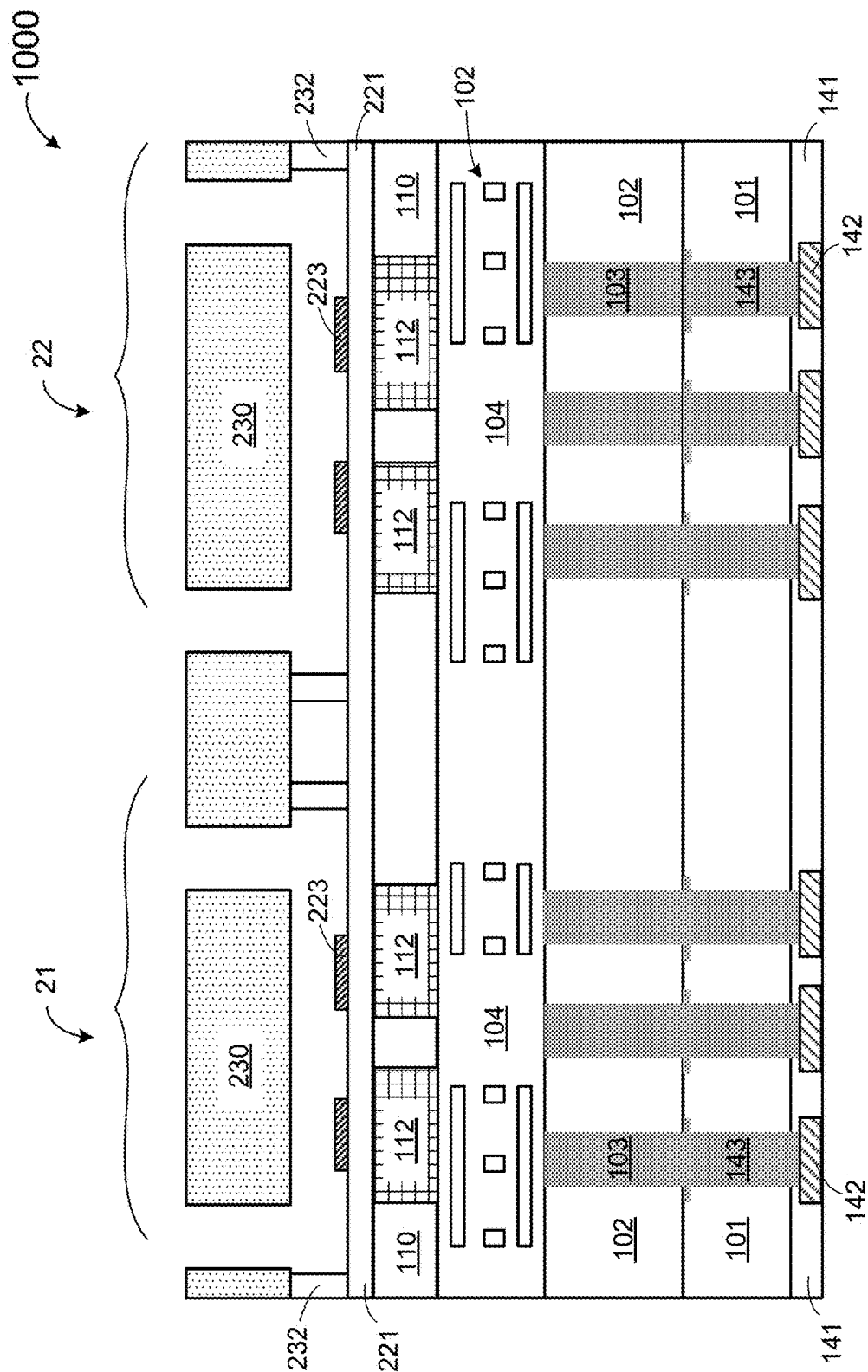

FIG. 10 is a cross-sectional view illustrating a wafer structure 1000 with backside packaging on the wafer structure 900 of FIG. 9 according to some embodiments of the invention. The backside packaging in FIG. 10 is similar to the backside packaging described above in connection with FIG. 4.

Figure 11:
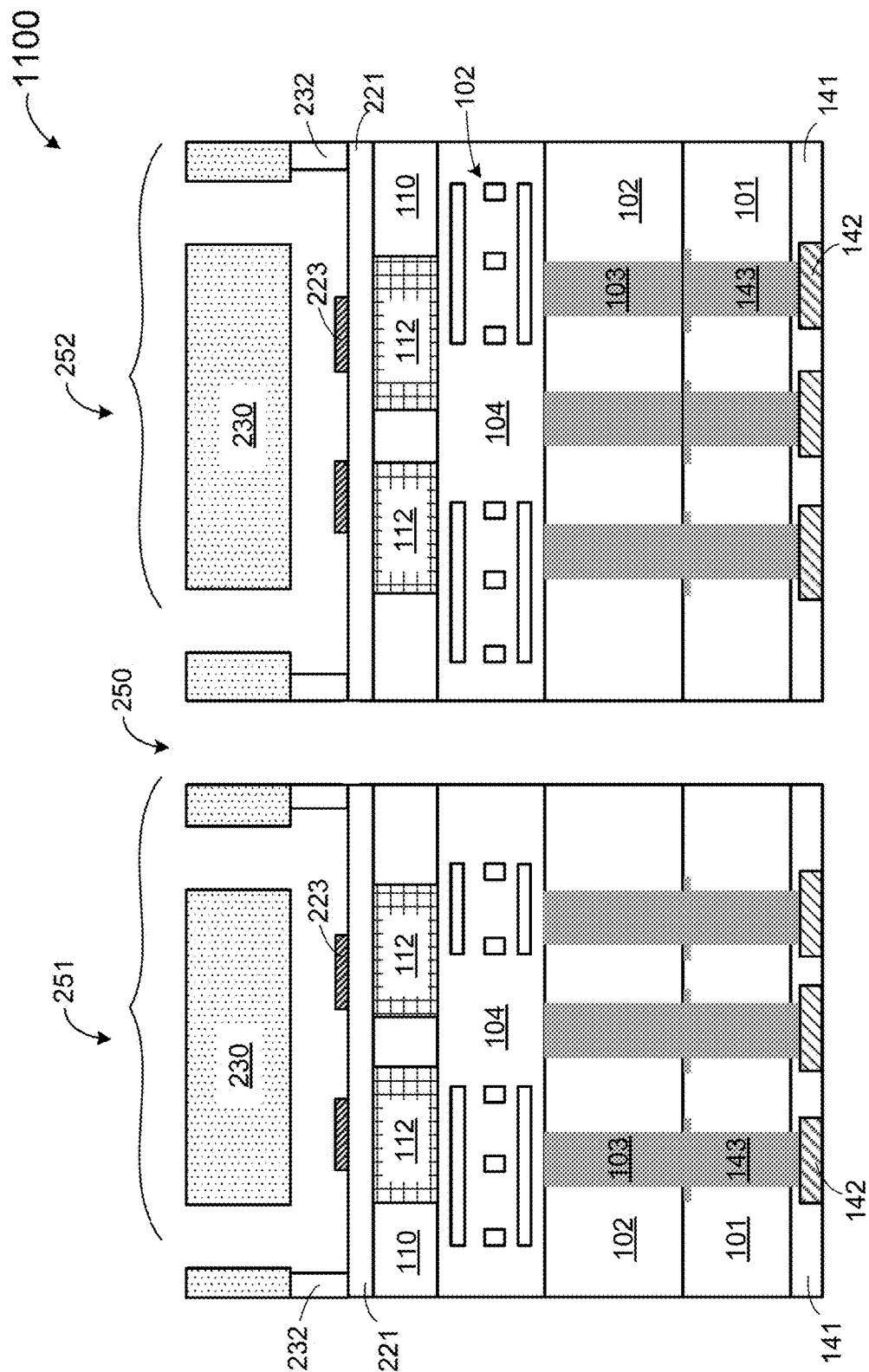

FIG. 11 is a cross-sectional view of a plurality of individual flow cell dies 1100 after a wafer singulation process at an intermediate stage of manufacture of sequencing flow cells according to embodiments of the invention. The singulation process illustrated in FIG. 10 is similar to the process described above in connection with FIG. 5. After singulation, two separate dies 251 and 252 are formed, and divided by scribe line 250.

Figure 12:
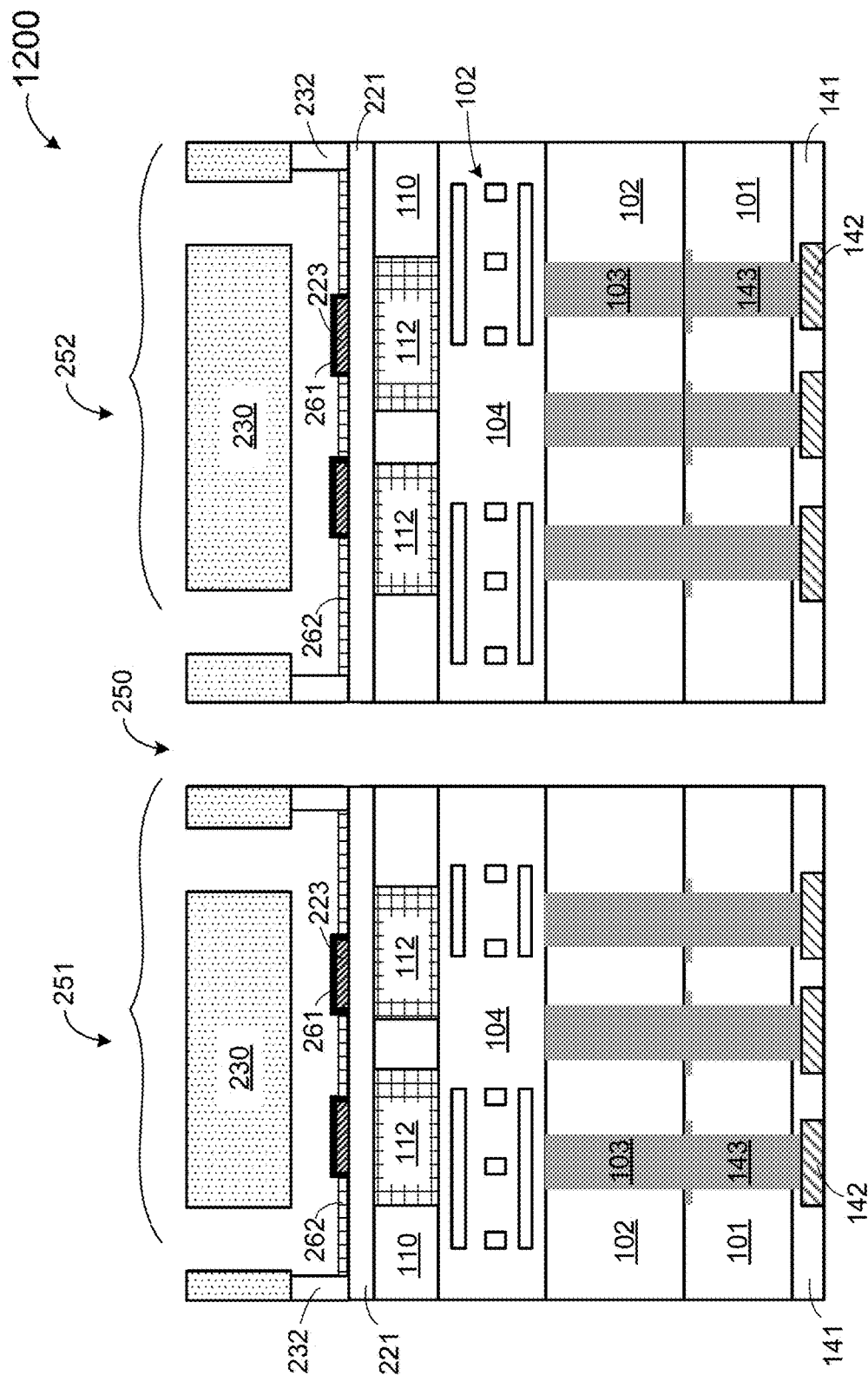

FIG. 12 is a cross-sectional view of a plurality of individual flow cell dies 1200 after a functionalization process is applied to the flow cell dies 1100 of FIG. 11 at an intermediate stage of manufacture of sequencing flow cells according to embodiments of the invention. The functionalization process illustrated in FIG. 12, with two different surfaces 261 and 262, is similar to the process described above in connection with FIG. 6.

Figure 13:
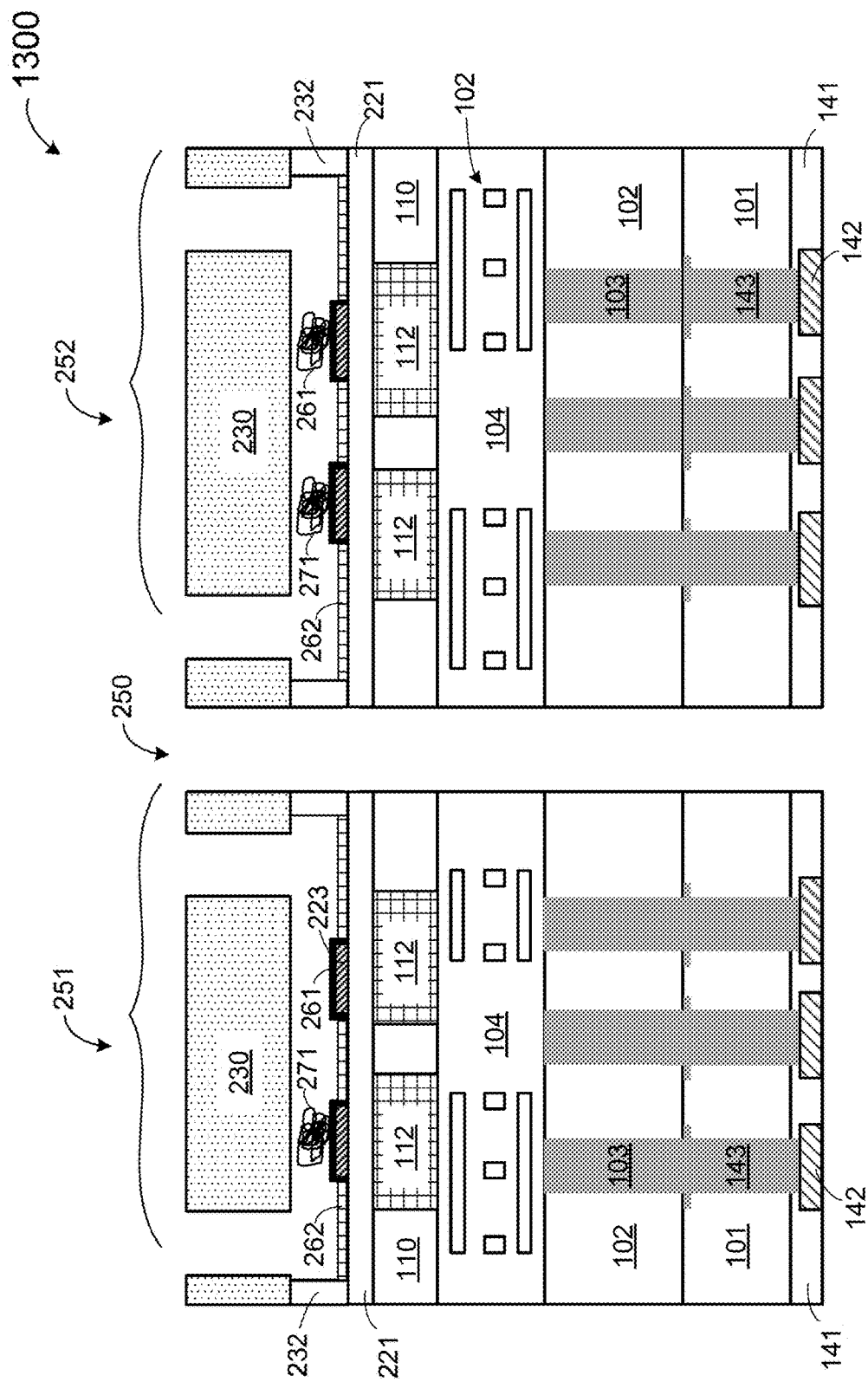

FIG. 13 is a cross-sectional view illustrating a plurality of individual flow cell dies 700 after a sample loading process in the sequencing flow cells 1200 of FIG. 12 according to embodiments of the invention. The loading of samples 271 illustrated in FIG. 13 is similar to the process described above in connection with FIG. 7.

III. Wafer Level Fabrication of Flow Cell on Bare Wafer

FIGS. 14-19 are cross-sectional views illustrating various stages of wafer scale packaging of sequencing flow cells according to another embodiment of the invention. The processes described in FIGS. 14-19 are similar to the processes of FIGS. 2-7 carried out on wafer 100 described in FIG. 1 that already has CMOS circuitry built in. In alternative embodiments, the processes described in FIGS. 14-19 can be carried out on a bare silicon wafer or other semiconductor wafers without built-in circuitry, as described below.

Figure 14:
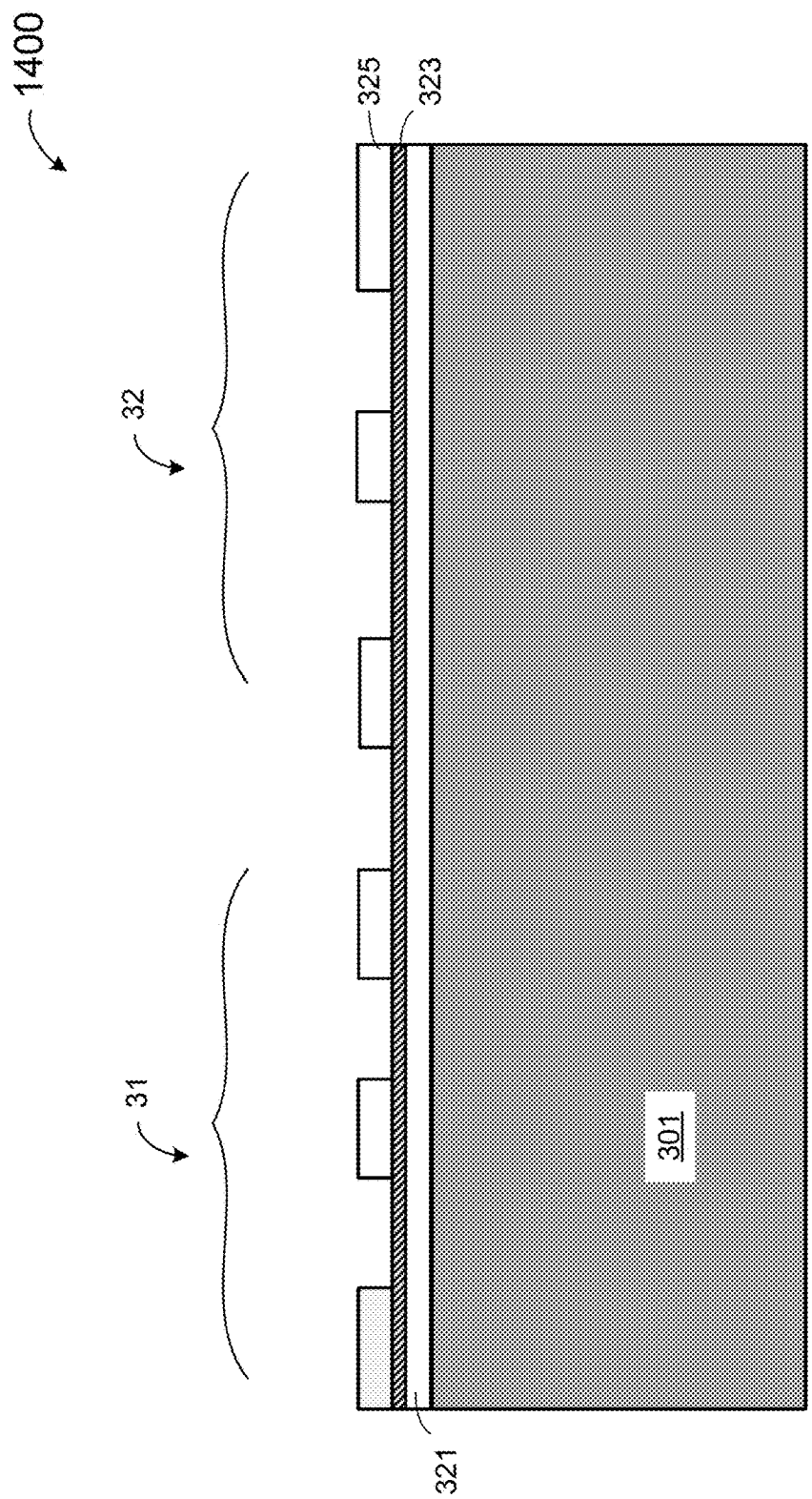
FIGS. 14-19 are cross-sectional views illustrating various stages of wafer scale packaging of sequencing flow cells according to another embodiment of the invention. The processes described in FIGS. 14-19 are similar to the processes of FIGS. 2-7 carried out on wafer 100 described in FIG. 1 that already has CMOS circuitry built in. In alternative embodiments, the processes described in FIGS. 14-19 can be carried out on a bare silicon wafer or other semiconductor wafers without built-in circuitry, as described below.

FIG. 14 is a cross-sectional view of a wafer structure 1400 having differential surface patterning over a bare wafer 301 according to some embodiments of the invention. Wafer structure 1400, similar to wafer structure 200 of FIG. 2, only shows regions 31 and 32, which are designed for two flow cells in two separate dies. Wafer structure 1400 also has alternately exposed regions of a first material and a second material that are formed overlying wafer 100 illustrated in FIG. 1. Bare wafer 301 is covered with a dielectric layer 321, which can be formed by a deposition process. In wafer structure 1400, the dielectric regions 325 are formed over the metal-containing regions 323. The dielectric regions 325 can be formed by a deposition and patterning process similar to that described above in connection with FIG. 2.

Figure 15:
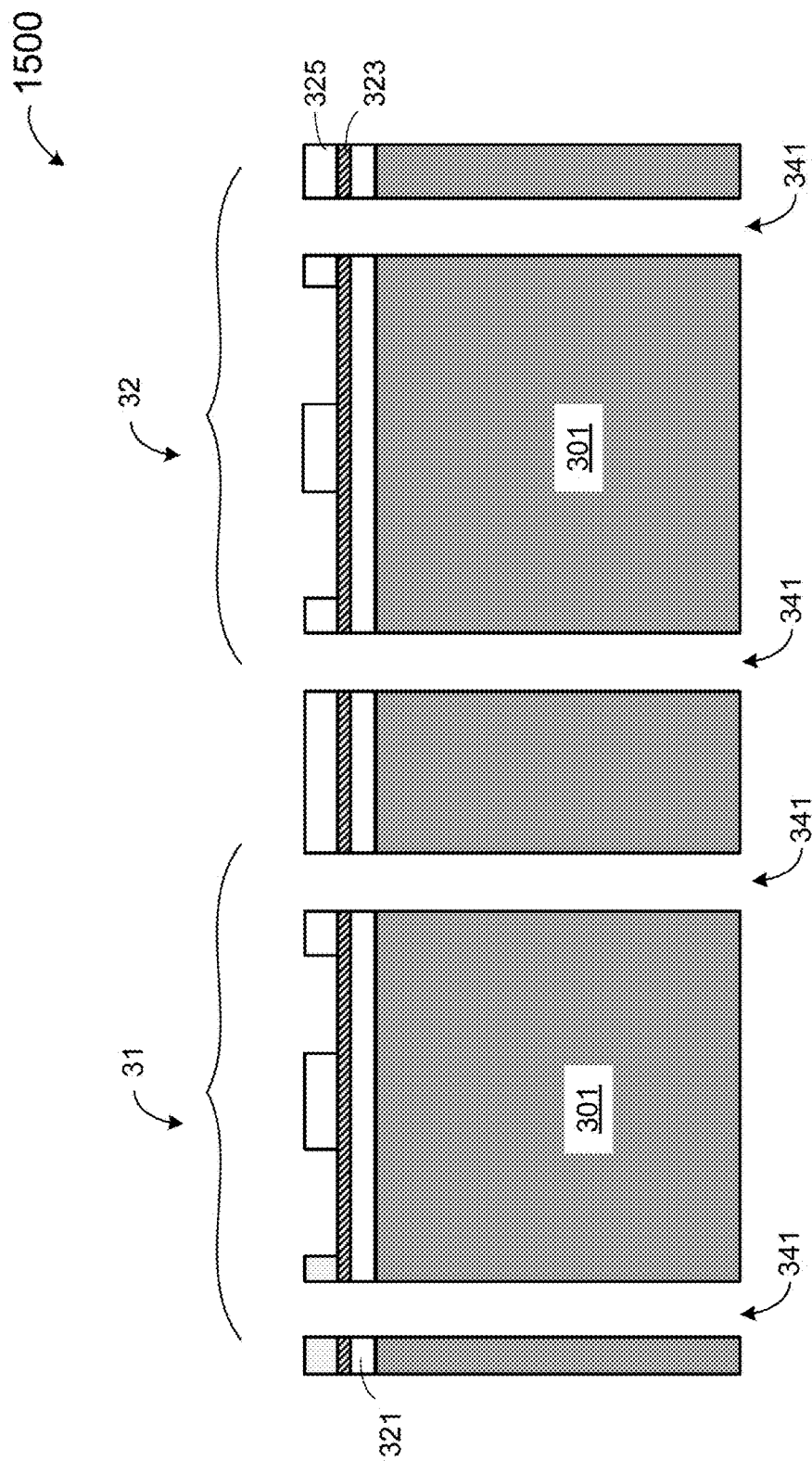

FIG. 15 is a cross-sectional view illustrating a wafer structure 1500 having through holes formed in the wafer structure 1400 of FIG. 14 according to some embodiments of the invention. Through holes 341 are formed to provide inlets and outlets for flow cells described below in connection with FIG. 16. The through holes can be formed using conventional patterning and etching processes used in silicon integrated circuit processing. Each area in wafer structure 1500 designated for a flow cell, such as 351 and 352, can have one or more through holes for forming inlets of the flow cell, and one or more through holes for forming outlets of the flow cell.

Figure 16:
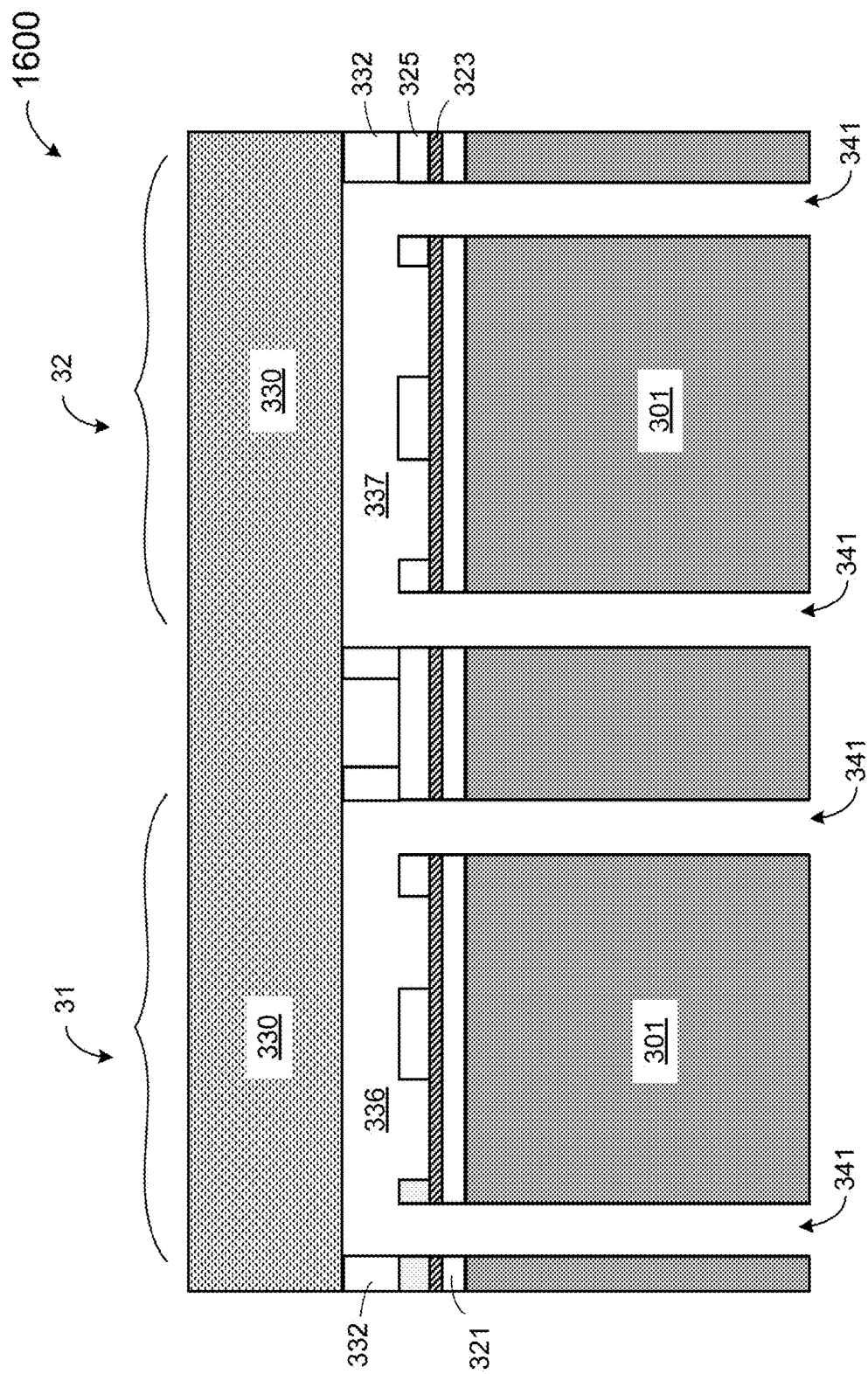

FIG. 16 is a cross-sectional view illustrating a wafer structure 1600 having a cover structure disposed over the wafer structure 1500 of FIG. 15 according to some embodiments of the invention. Cover structure 330 and support structures 332 can be formed using similar processes as described above in connection with FIG. 3. A difference is that in FIG. 16, the cover structure can be a wafer, such as a glass wafer, without any inlet or outlet structures as shown in FIG. 3. In FIG. 16, flow channels 336 and 337 are formed under the cover structure 330, and each flow cell can have one or more inlets and one or more outlets formed by through holes 341.

Figure 17:
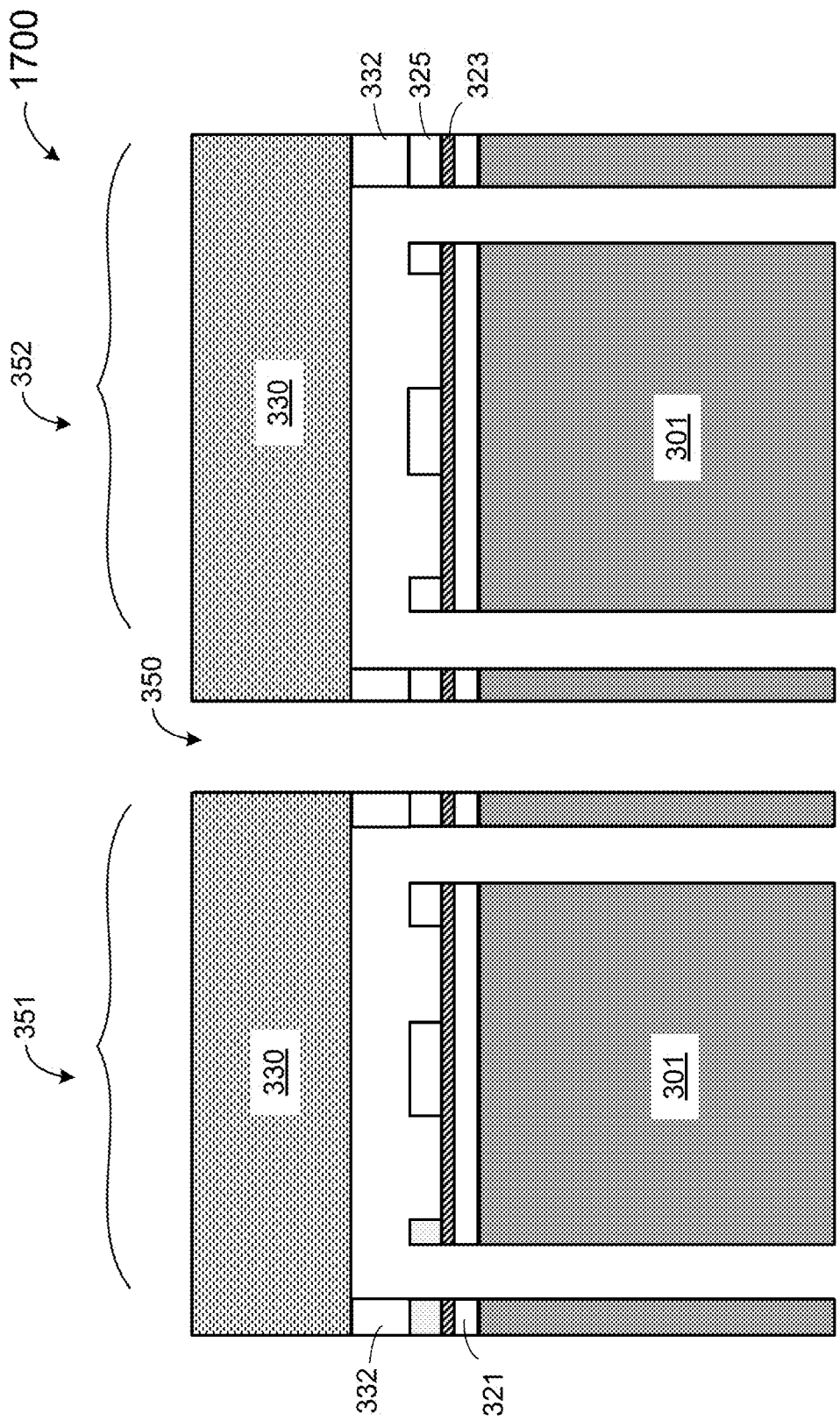

FIG. 17 is a cross-sectional view of a plurality of individual flow cell dies 1700 after a wafer singulation process at an intermediate stage of manufacture of sequencing flow cells according to embodiments of the invention. The singulation process illustrated in FIG. 17 is similar to the process described above in connection with FIG. 5. After the singulation process, flow cell dies or chips 351 and 352 are separated by a space 350 defined by the scribe lines in the wafer.

Figure 18:
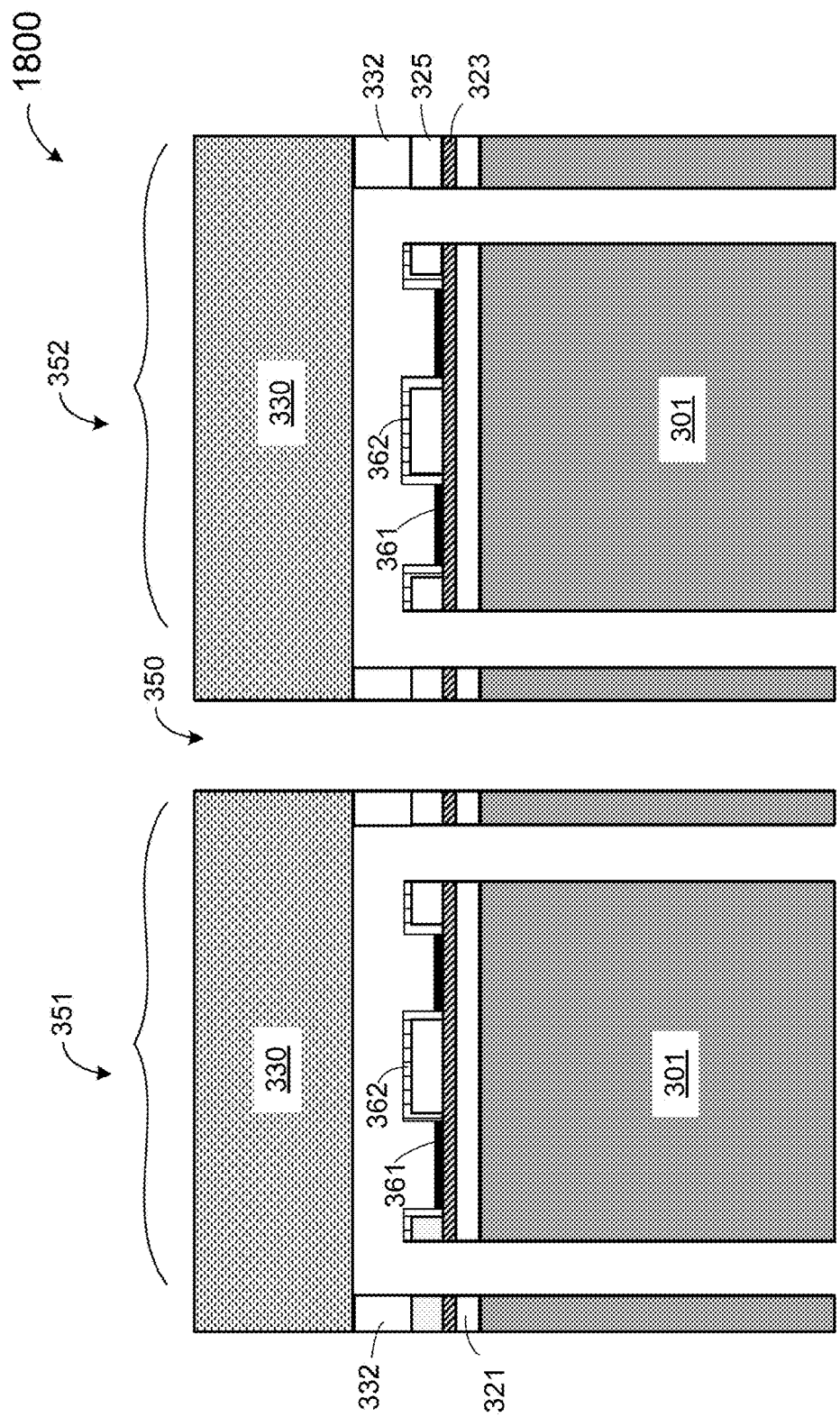

FIG. 18 is a cross-sectional view of a plurality of individual flow cell dies 1800 after a functionalization process is applied to the flow cell dies 1700 of FIG. 17 according to embodiments of the invention. The functionalization process illustrated in FIG. 18 is similar to the process described above in connection with FIG. 6. Regions of two different surface layers 361 and 362 are formed.

Figure 19:
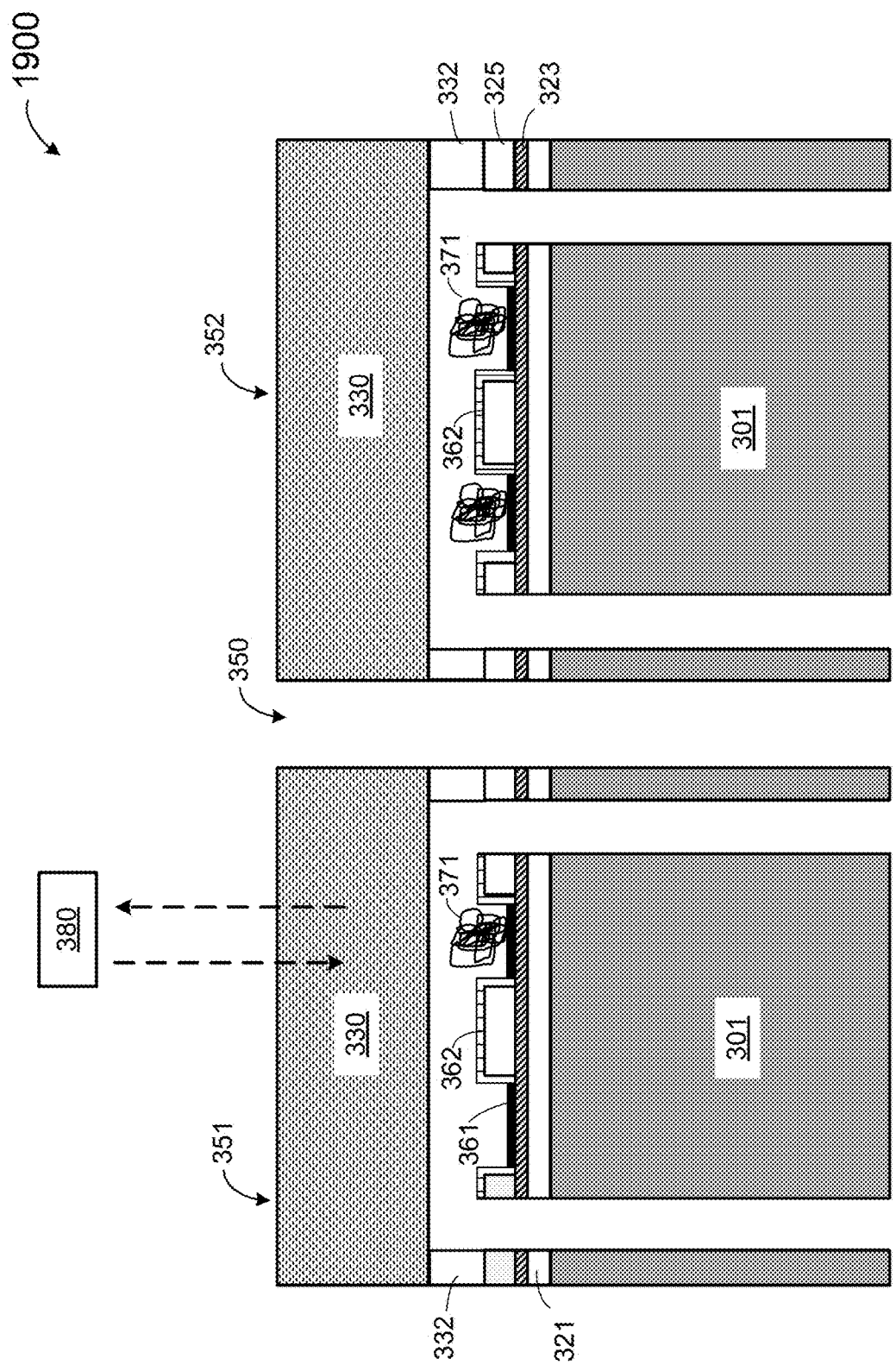

FIG. 19 is a cross-sectional view illustrating a plurality of individual flow cell dies 1900 after a sample loading process in the sequencing flow cells 1800 of FIG. 18 according to embodiments of the invention. The sample loading process illustrated in FIG. 19 is similar to the process described above in connection with FIG. 7. FIG. 19 also shows a light source and camera 380 for providing the illumination and capture of the emission from the flow cells. Alternatively, in applications without illumination, e.g., bioluminescence, block 380 can represent a camera for capture of the emission.

IV. Alternative Wafer Level Fabrication of Flow Cell on Bare Wafer

FIGS. 20-25 are cross-sectional views illustrating various stages of wafer scale packaging of sequencing flow cells according to another embodiment of the invention. The processes described in FIGS. 20-25 are similar to those described above in connection to FIGS. 14-19, which are implemented over a bare wafer.

Figure 20:
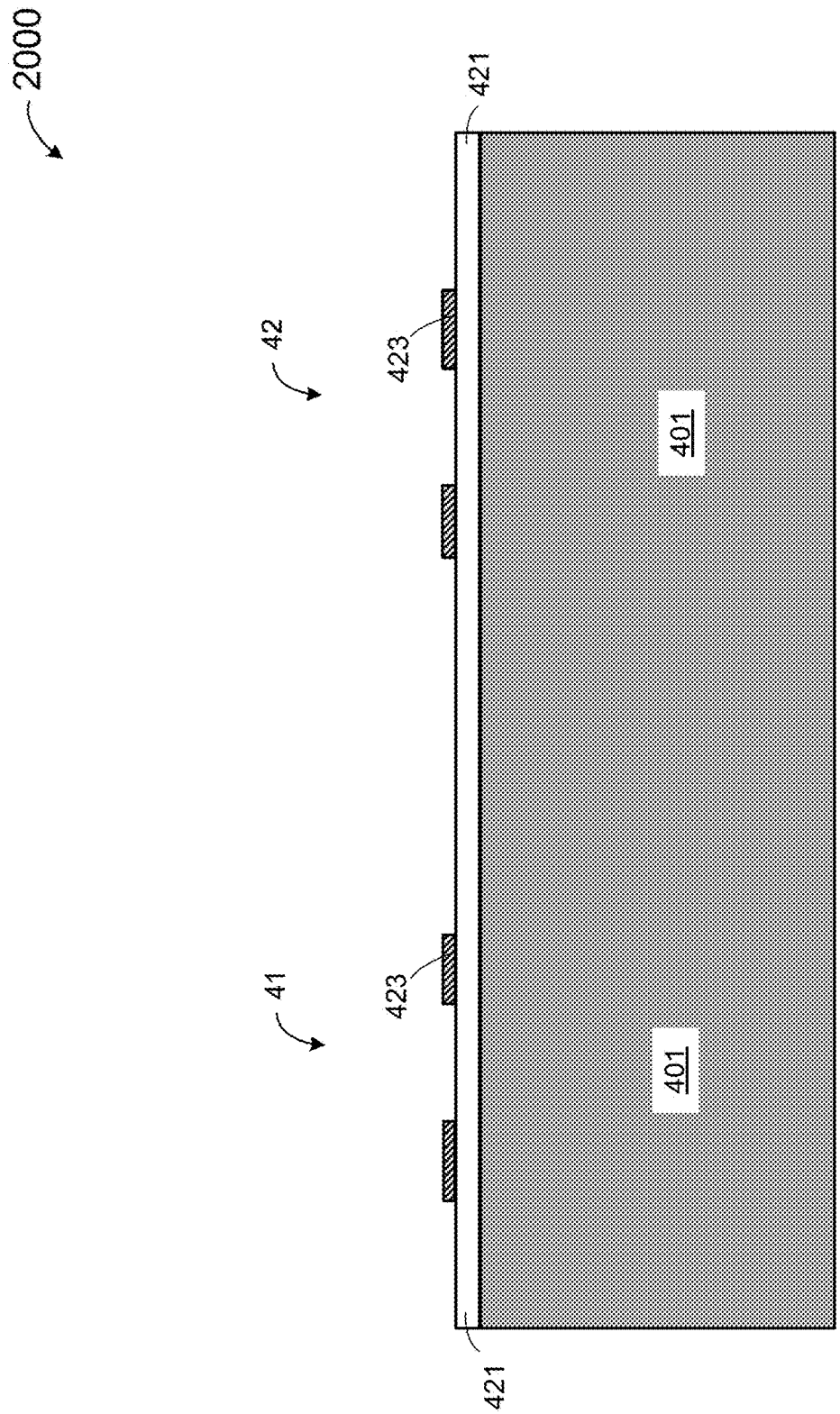
FIGS. 20-25 are cross-sectional views illustrating various stages of wafer scale packaging of sequencing flow cells according to another embodiment of the invention. The processes described in FIGS. 20-25 are similar to those described above in connection to FIGS. 14-19, which are implemented over a bare wafer.

FIG. 20 is a cross-sectional view of a wafer structure 2000 having differential surface patterning over a bare wafer according to some embodiments of the invention. Wafer structure 2000, similar to wafer structure 1400 of FIG. 14, shows two areas designated for flow cells, such as 41 and 42, and has alternately exposed regions of a first material and a second material that are formed overlying a wafer. However, in wafer structure 1400, the dielectric regions 325 are formed over the metal-containing regions 323, whereas in wafer structure 2000, the metal-containing regions 423 are formed over the dielectric layer 421. The metal-containing regions 423 can be formed by a deposition and patterning process similar to that described above in connection with FIG. 2.

Figure 21:
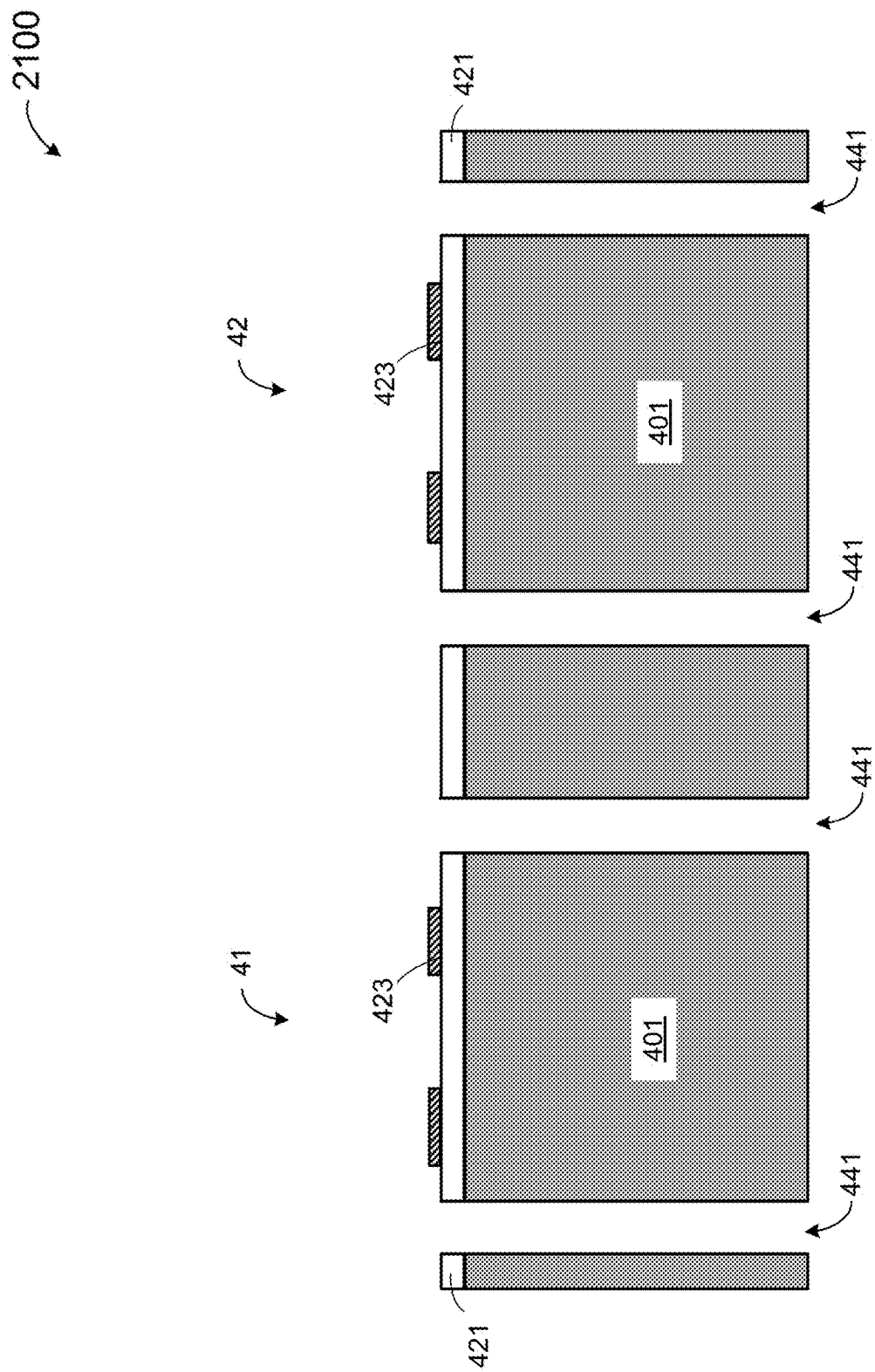

FIG. 21 is a cross-sectional view illustrating a wafer structure 2100 having through holes formed in the wafer structure 2000 of FIG. 20 according to some embodiments of the invention. Through holes 441 are formed to provide inlets and outlets for flow cells described below in connection with FIG. 16. The through holes can be formed using conventional patterning and etching processes used in silicon integrated circuit processing. Each area in wafer structure 2100 designated for a flow cell, such as 41 and 42, can have one or more through holes for forming inlets of the flow cell, and one or more through holes for forming outlets of the flow cell.

Figure 22:
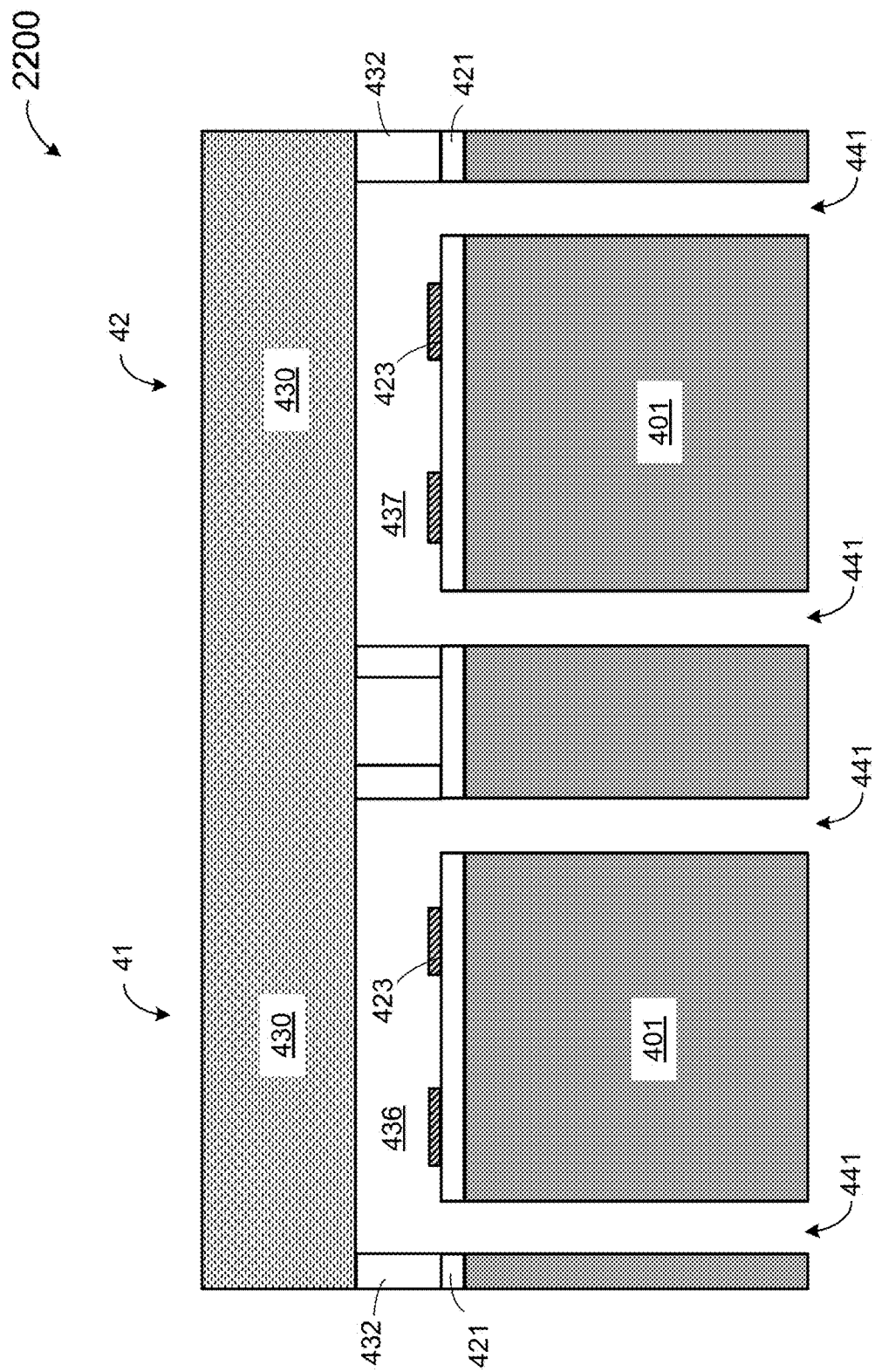

FIG. 22 is a cross-sectional view illustrating a wafer structure 2200 having a cover structure disposed over the wafer structure 2100 of FIG. 21 according to some embodiments of the invention. Cover structure 430 and support structures 432 can be formed using similar processes as described above in connection with FIG. 3. Similar to the cover structure 330 in FIG. 16, the cover structure 430 can be a wafer, such as a glass wafer, without any inlet or outlet structures as shown in FIG. 3. In FIG. 22, flow channels 436 and 437 are formed under the cover structure 430, and each flow cell can have one or more inlets and one or more outlets formed by through holes 441.

Figure 23:
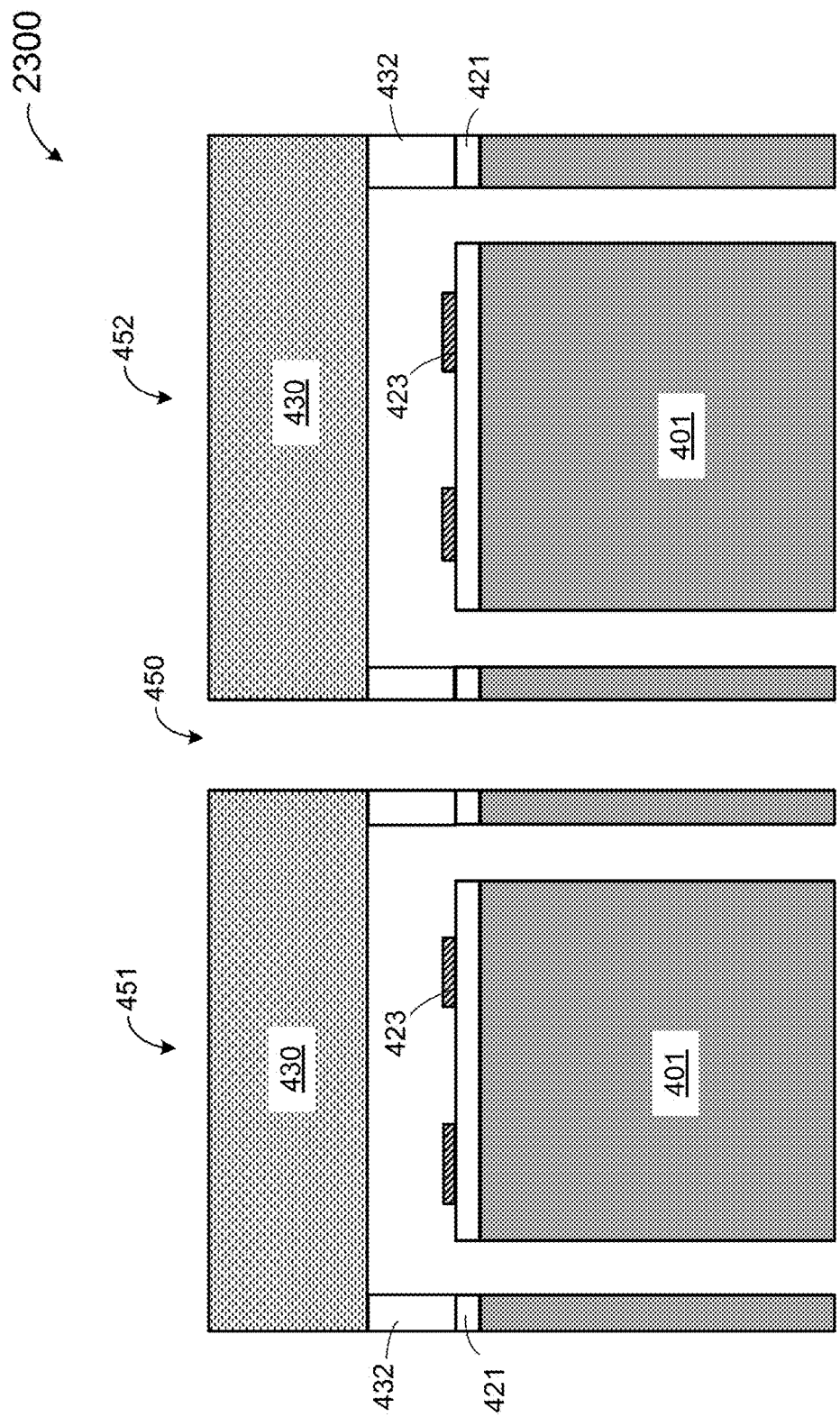

FIG. 23 is a cross-sectional view of a plurality of individual flow cell dies 2300 after a wafer singulation process at an intermediate stage of manufacture of sequencing flow cells according to embodiments of the invention. The singulation process illustrated in FIG. 23 is similar to the process described above in connection with FIG. 5. After the singulation process, flow cell dies or chips 451 and 452 are separated by a space 450 defined by the scribe lines in the wafer.

Figure 24:
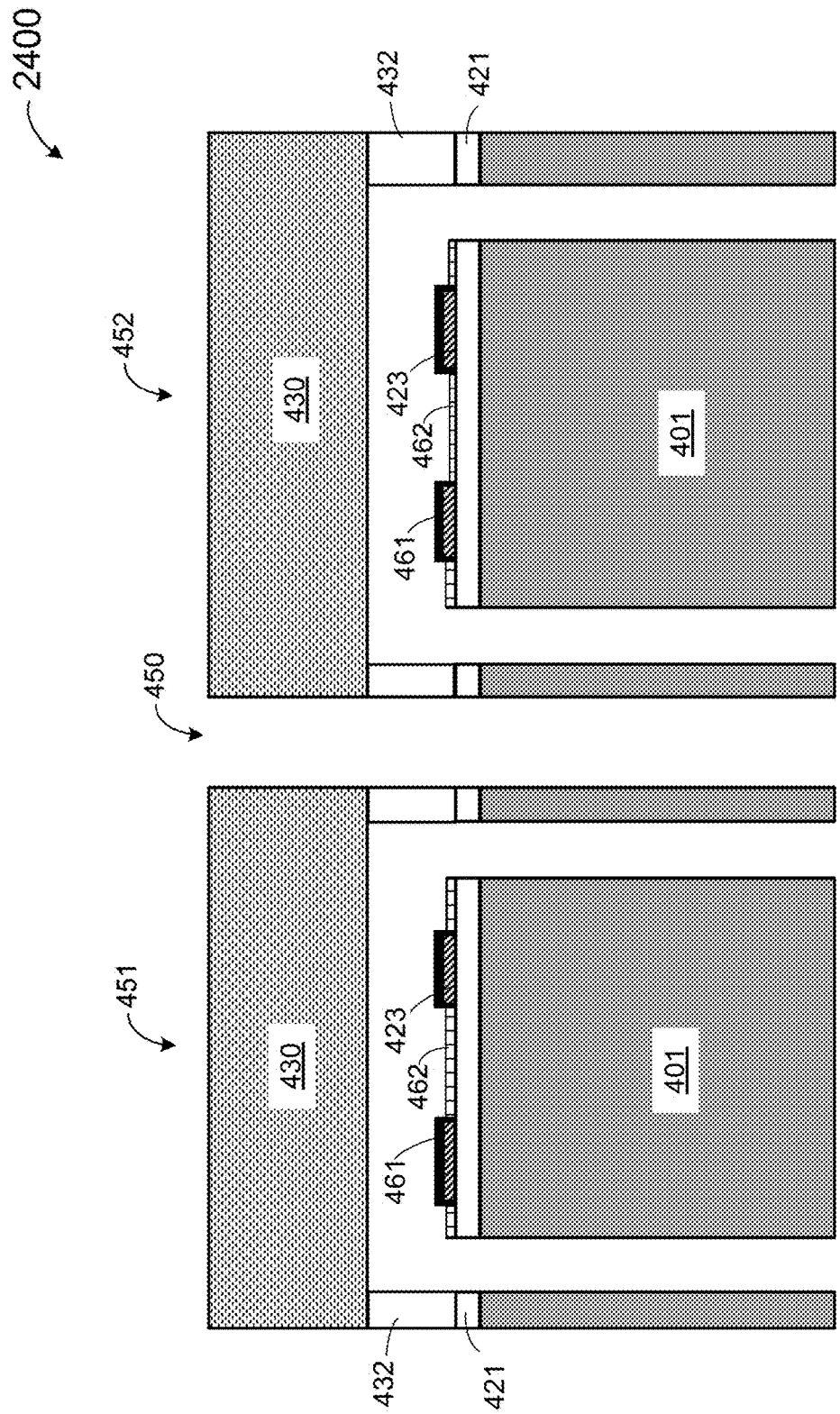

FIG. 24 is a cross-sectional view of a plurality of individual flow cell dies 2400 after a functionalization process is applied to the flow cell dies 2300 of FIG. 23 according to embodiments of the invention. The functionalization process illustrated in FIG. 24 is similar to the process described above in connection with FIG. 6. In FIG. 24, two different surface layers 461 and 462 are formed.

Figure 25:
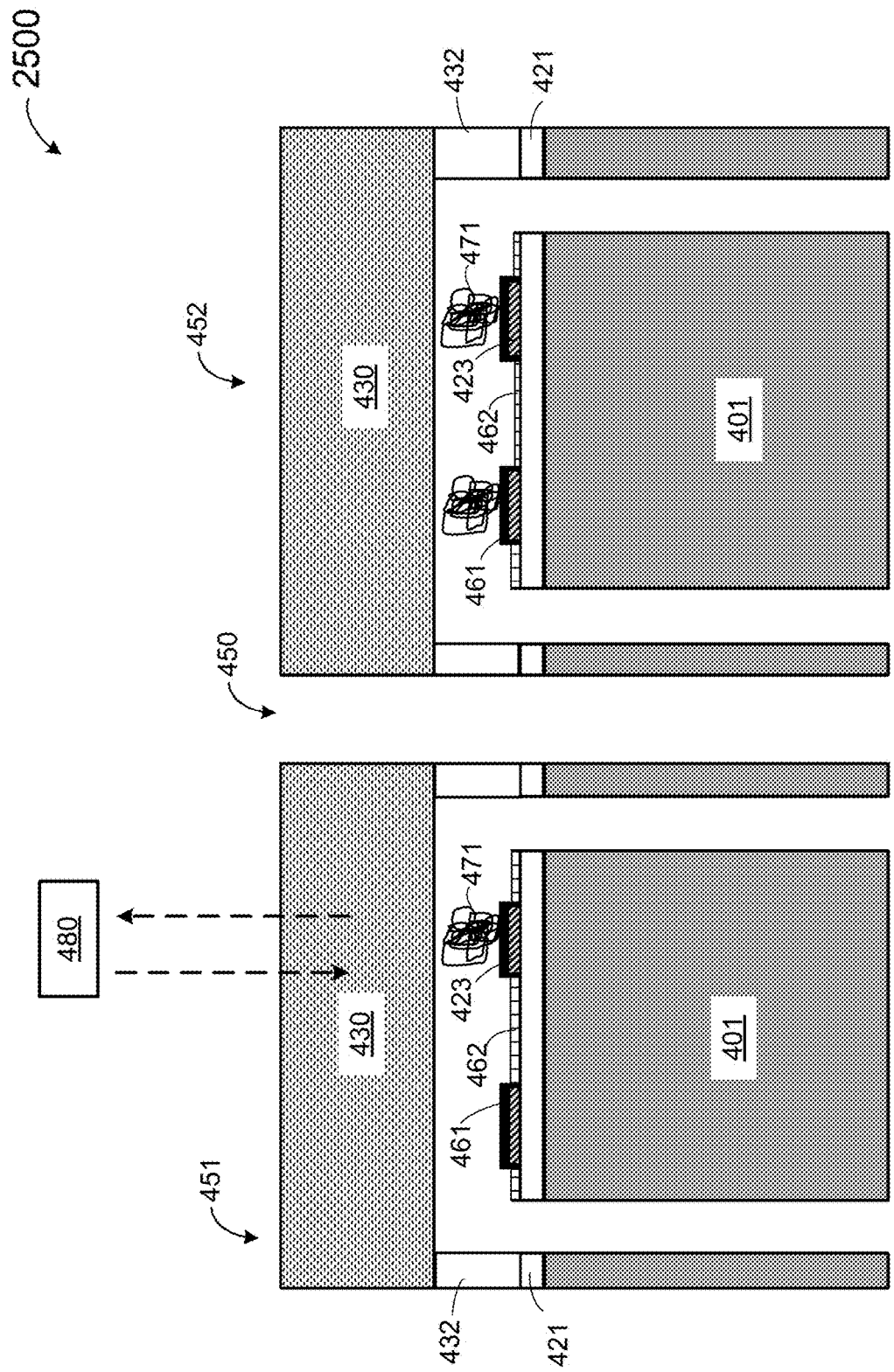

FIG. 25 is a cross-sectional view illustrating a plurality of individual flow cell dies 2500 after a sample loading process in the sequencing flow cells 2400 of FIG. 2 according to embodiments of the invention. The sample loading process illustrated in FIG. 25 is similar to the process described above in connection with FIG. 7. In some embodiments, the biological sample comprises DNA nanoballs (DNBs) 471 which may be attracted to or bind to the first surface layer 161. FIG. 25 also shows a light source and camera 480 for providing the illumination and capture of the emission from the flow cells. Alternatively, in applications without illumination, e.g., bioluminescence, block 480 can represent a camera for capture of the emission.

Although the processes described herein are described with respect to a certain number of steps being performed in a certain order, it is contemplated that additional steps may be included that are not explicitly shown and/or described. Further, it is contemplated that fewer steps than those shown and described may be included without departing from the scope of the described embodiments (i.e., one or some of the described steps may be optional). In addition, it is contemplated that the steps described herein may be performed in a different order than that described.

V. Differential Surfaces for Flow Cells

Hydrophobic/hydrophilic interstitial surface with dimension from micrometers to nanometer has many important biotech applications, such as forming droplets array inside oil for droplet digital PCR, DNA nanoball array for DNA sequencing, and single cell array for single cell analysis, etc. In different embodiments, various methods are described for forming hydrophobic and hydrophilic interstitial surfaces based on patterned inorganic surfaces by semiconductor processing techniques. Traditional fabrication methods involve patterning organic hydrophobic polymer like Teflon, Cytop using special processes and materials, which are hard to incorporated into standard semiconductor foundry processes. Therefore, such processes are unsuitable for mass production, and their cost can be too high to many applications.

Figure 26:
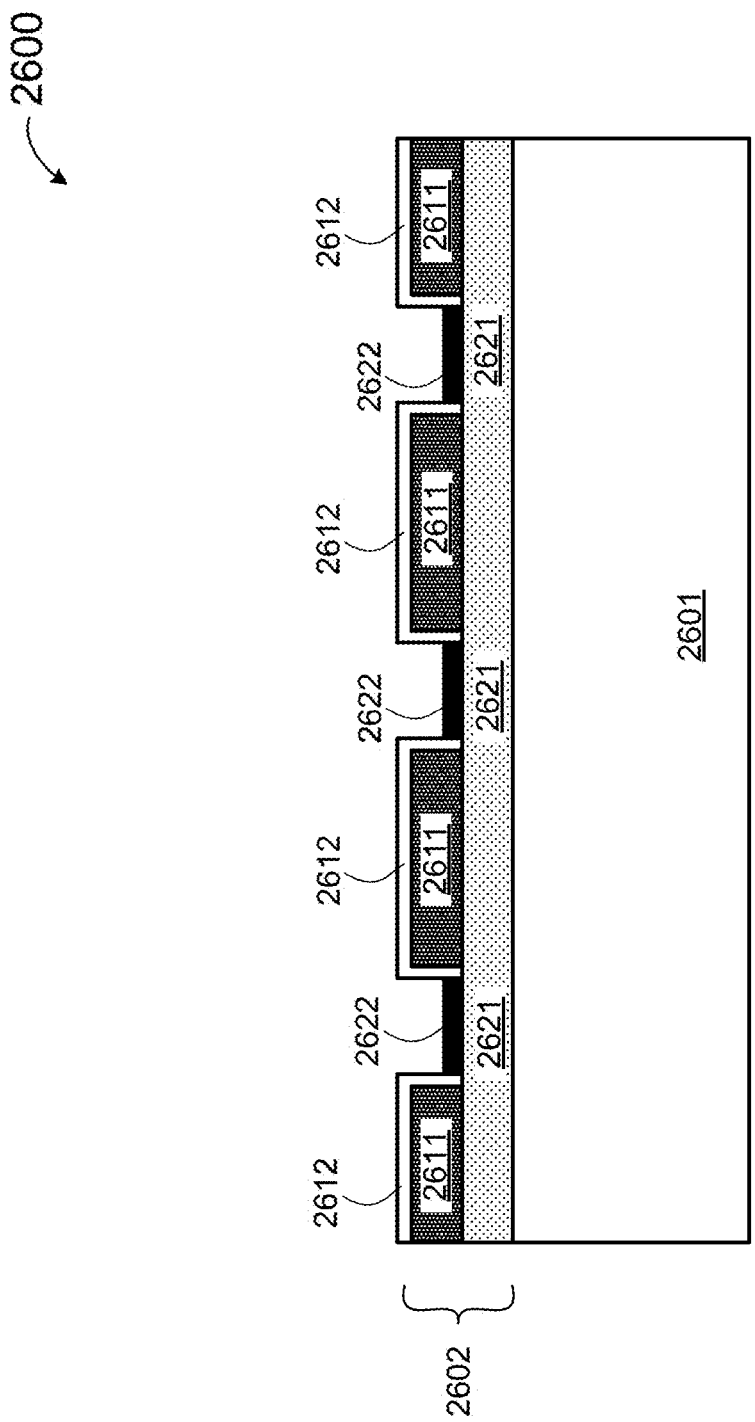
FIG. 26 is a cross-sectional view of a device structure 2600 having differential surface regions according to some embodiments.

FIG. 26 is a cross-sectional view of a device structure 2600 having differential surface regions according to some embodiments of the invention. Device structure 2600 includes a substrate 2601. A surface layer 2602 including a plurality of first thin film regions 2611 and a plurality of second thin film regions 2621 are disposed on substrate 2601. It is further noted that the methods described here are applicable to forming a layer having differential surface regions on any suitable substrate 2601, for example, a CMOS device with sensors, a bare semiconductor wafer, a glass substrate, etc. Further details are described below in connection with FIGS. 27A, 41, and 44.

A first covering layer 2612 is formed on the top surfaces of the first thin film regions 2611, and a second covering layer 2622 is formed on the top surfaces of the second thin film regions 2621. In some embodiments, a differential surface layer is formed by alternating regions of first covering layer 2612 and regions of second covering layer 2622.

According to some embodiments, methods are provided for selecting the first material and the second material to adjust the hydrophobicity of the first covering layer and the second covering layer to form a differential hydrophobic/hydrophilic surface.

In some embodiments, differential hydrophobic/hydrophilic surface can have alternating nonpolar molecular regions that repels water and polar molecular regions which can form ionic or hydrogen bond with water molecular. In some embodiments, a method includes first forming alternating regions of inorganic silicon oxide $SiO_2$ and metal oxide material including one or more of various metal oxides, such anodized aluminum ($Al_2O_3$), tantalum oxide ($Ta_2O_5$), niobium oxide ($Nb_2O_5$), zirconium oxide ($ZrO_2$), and titanium oxide ($TiO_2$), etc. These alternating regions can be formed using standard semiconductor thin film deposition and photolithography process on Si or glass substrate, as described further below.

Next, the metal oxide surfaces can be treated to modify the surface property. One method is to selectively coat it using polyvinylphosphonic acid (PVPA), which is a type of hydrophilic polymer inside the native pH of the phosphonic acid (pH=2), at a temperature in the temperature range of 80° C. to 100° C. In a specific embodiment, the treatment can be carried at, for example, 90° C. In some cases, the treatment can be relatively fast, for example, in less than 2 min. This step can be followed by a dry annealing step intended to support formation of covalent bonds. A dry anneal process can be carried at a suitable temperature, e.g., at 80° C. for about 10 min. This reaction can be selective, i.e., no reaction will take place on the SiO2 surface.

Another method is to selectively coat the metal oxide regions by self-assembled monolayers (SAMs) based on the adsorption of the alkyl phosphate ammonium salts from aqueous solution. SAM formation does not occur on SiO2 surfaces under the same conditions. The coated surface hydrophobicity can be adjusted by the formulation in the aqueous SAM forming solution, and the contact angle of water can range from 50 to 110 degrees. In some cases, the contact angle of water can range from 20 to 130 degrees. Covalent bonds can be formed during the annealing, and unreacted materials rinsed by DI water.

After the PVPA or phosphate treatment, the substrate can be dried and treated with a hydrophobic silane such as Fluorinated Alkyl-Silanes, dialkyl-Silanes etc. Alternatively the substrate can be dried and treated with a hydrophilic silane such as Hydroxyakyl terminated silanes in solution or chemical vapor deposition. These treatment can form stable covalent bonds with the SiO2 surface and change the surface to be hydrophobic or hydrophilic without affecting metal oxide surface's hydrophobicity.

With the highly selective surface treatment of inorganic SiO2 and metal oxide surfaces with different organic chemicals of different hydrophobicity, the differential hydrophobic/hydrophilic surface can be made with well-defined patterns by the semiconductor processes.

FIGS. 27A-27F are cross-sectional views illustrating a method for forming the a device structure of FIG. 26 having differential surface regions according to some embodiments of the invention. The method for forming a device structure having differential surfaces includes providing a substrate, and forming a surface layer having alternating first thin film regions and second thin film regions on the substrate. The surface layer is exposed to a first material to form a first covering layer on the first thin film regions, but not on the second thin film regions. The surface layer is then exposed to a second material to form a second covering layer on the second thin film regions, but not on the first thin film regions which are now covered by the first covering layer. The method includes selecting the first material and the second material to adjust the hydrophobicity of the first covering layer and the second covering layer.

Figure 27A:
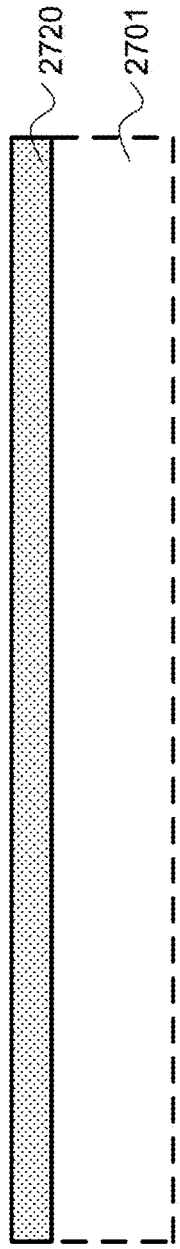
FIGS. 27A-27F are cross-sectional views illustrating a method for forming the a device structure of FIG. 26 having differential surface regions according to some embodiments.

FIG. 27A shows a thin film layer formed on a substrate. In FIG. 27A, a thin film layer 2720 is formed on a substrate 2701. Substrate 2701 may be made of any suitable material, for example, a glass or a semiconductor. A semiconductor substrate can include various semiconductor materials, such as silicon, III-V group on silicon, graphene-on-silicon, silicon-on-insulator, combinations thereof, and the like. Substrate 2701 can be a bare wafer, similar to bare wafer 301 in FIG. 14. Substrate 2701 can also include various device an circuit structures. For example, substrate 2701 can be similar to semiconductor wafer 100 illustrated in FIG. 1, which can include a CMOS image sensor layer 10, a CMOS processing circuitry layer 20, and a stacking layer 30. Optionally, substrate 2701 can also include a top passivation layer or insulating layer (not shown), similar to passivation layer 121 in FIG. 1. The passivation layer may include any suitable protective material. For example, the passivation layer may include materials such as silicon nitride, silicon oxide, other dielectric materials, or combinations thereof. The passivation layer may be deposited by conventional semiconductor thin film deposition techniques, e.g., chemical vapor deposition (CVD), low temperature plasma chemical vapor deposition (LPCVD), plasma-enhanced chemical vapor deposition (PECVD), sputtering, physical vapor deposition (PVD), and atomic layer deposition (ALD), etc.

In FIG. 27A, thin film layer 2720 is formed on substrate 2701. In an embodiment, thin film layer 2720 contains inorganic silicon oxide, e.g., SiO2. In some embodiments, thin film layer 2720 can include silicon, silicon nitride, metal oxides, etc., or combinations thereof. Thin film layer 2720 can also include other materials that can be silanized. Thin film layer 2720 can be formed on substrate 2701 using conventional semiconductor thin film deposition techniques described above.

Figure 27B:
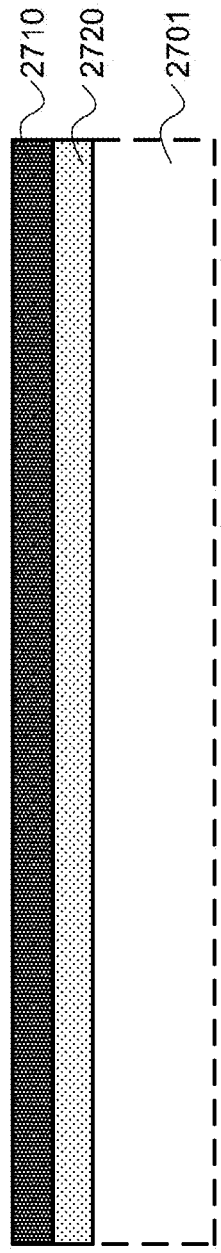

FIG. 27B shows a second thin film layer 2710 formed on a first thin film layer 2720. In some embodiments, 2710 can include metal oxides or metals. Suitable metal oxides can include, for example, anodized aluminum ($Al_2O_3$), tantalum oxide ($Ta_2O_5$), niobium oxide ($Nb_2O_5$), Zirconium oxide ($ZrO_2$), and titanium oxide ($TiO_2$), etc. Thin film layer 2610 can also include metal materials, such as tungsten, titanium, titanium nitride, silver, tantalum, tantalum oxide, hafnium, chromium, platinum, tungsten, aluminum, gold, copper, combinations or alloys thereof, and the like. Thin film layer 2610 can also be formed using conventional semiconductor thin film deposition techniques described above.

Figure 27C:
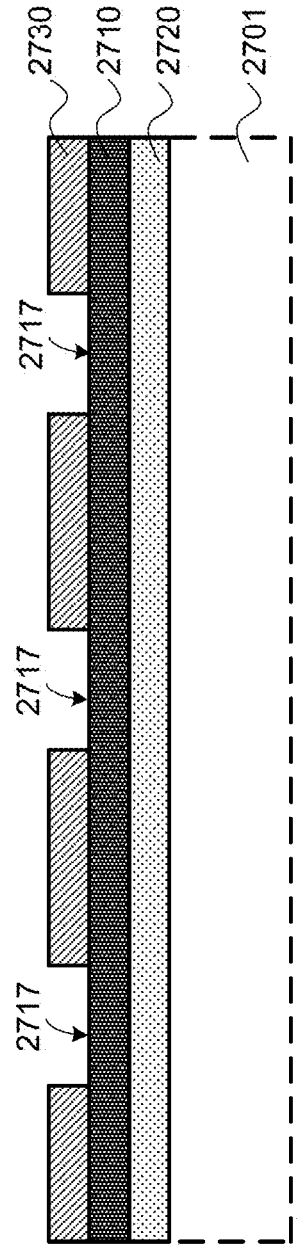

FIG. 27C shows a patterned mask layer 2730 formed on thin film layer 2710. The mask layer 2730 includes openings exposing regions of thin film layer 2710. Mask layer 2730 may be applied according to any suitable method, such as spin coating, dipping, and/or the like. Mask layer 2730 may also be of any suitable material, such as a photoresist. As shown in FIG. 27C, mask layer 2730 is patterned with the openings according to conventional semiconductor lithography techniques. In some embodiments, mask layer 2630 can be a hard mask, which is a patterned layer of suitable thin film material having suitable etch selectivity to serve as an etching mask.

After the patterned mask layer 2730 is formed, an etch process can be carried out to remove the exposed portions 2717 in thin film layer 2710. The etch process can be performed according to conventional semiconductor process techniques. Subsequently, the patterned mask layer 2730 can be removed by conventional semiconductor process techniques. The resulting device structure is illustrated in FIG. 27D.

Figure 27D:
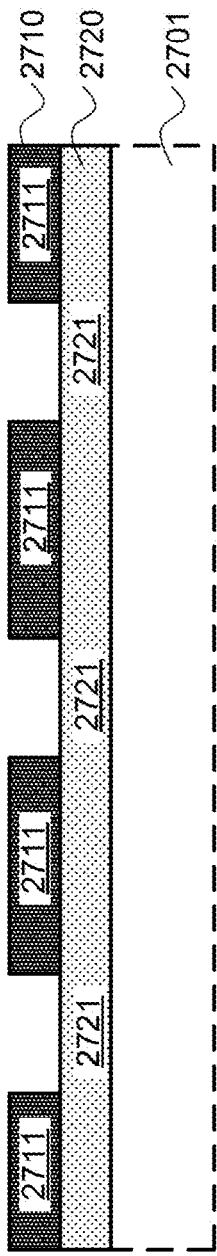

FIG. 27D shows a cross-sectional view of a device structure having alternating thin film regions 2711 of thin film layer 2710 and thin film regions 2721 of thin film layer 2720 according to some embodiments of the invention. After the patterning process, a surface layer including a plurality of first thin film regions 2711 and a plurality of second thin film regions 2621 are formed on substrate 2701.

Figure 27E:
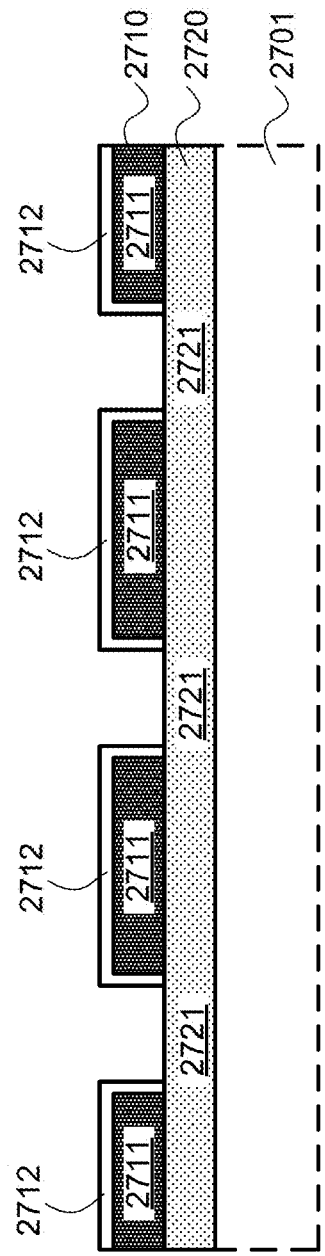

FIG. 27E shows a covering layer 2712 selectively formed on thin film region 2711. The selective covering layer formation is carried out by exposing the device structure to a suitable first material, such that covering layer 2712 is formed on the top surfaces of the thin film regions 2711, but not on the top surfaces of the thin film regions 2721. Depending on the materials for thin film regions 2711 and 2721, various materials can be used, as described in detail below. After the treatment of the material, an annealing process can be performed to selectively form covering layer 2712 on thin film region 2711. The annealing process can be carried out at a temperature in a range of 70°-90° C. for 5-15 minutes. As an example, a dry anneal process can be carried out at a temperature of 80° C. for 10 minutes. The unreacted material can be removed by a rinse process in DI (deionized) water.

Figure 27F:
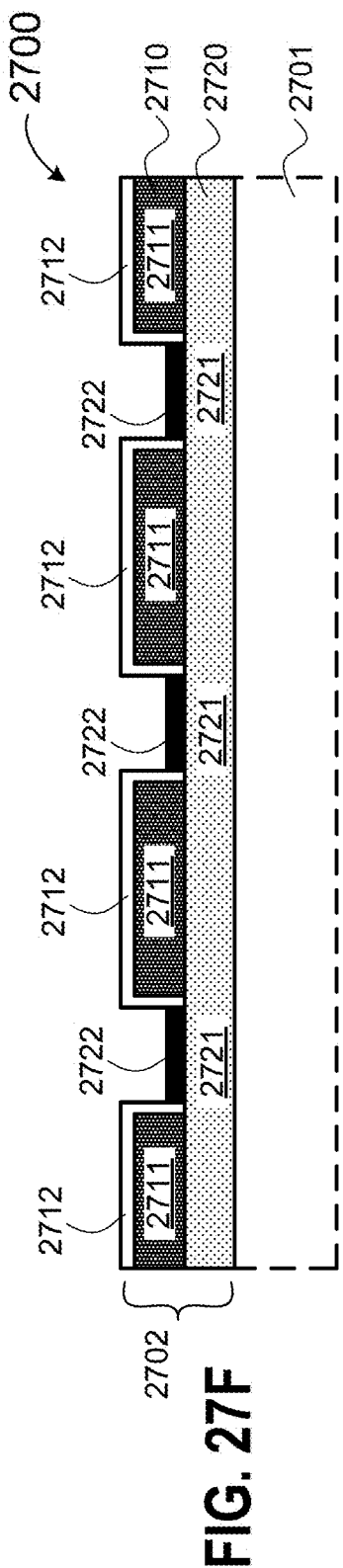

FIG. 27F shows a second covering layer 2722 selectively formed on the top surfaces of the second thin film regions 2721. The selective covering layer formation is by exposing the device structure to a suitable second material, such that covering layer 2722 is formed on the top surfaces of the thin film regions 2721, but not on the top surfaces of thin film regions 2711 with covering layer 2712. Depending on the materials for thin film regions 2711 and 2721, various materials can be used, as described in detail below. After the process with the second material, FIG. 27F shows a cross-sectional view of a device structure 2700, similar device structure 2600 of FIG. 26, having a surface layer 2702 with differential surface regions 2712 and 2722 according to some embodiments of the invention. As shown, device structure 2700 includes a substrate 2701. Surface layer 2702 including a plurality of first thin film regions 2711 and a plurality of second thin film regions 2721 are disposed on substrate 2701.

A first covering layer 2712 is formed on the top surfaces of the first thin film regions 2711, and second covering layer 2722 is formed on the top surfaces of the second thin film regions 2721. In this embodiment, a differential surface layer is formed by alternating regions of first covering layer 2712 and regions of second covering layer 2722.

In some embodiments, the differential surface regions can include alternating hydrophilic surfaces and hydrophobic surfaces. In some embodiments, the differential surface regions can include alternating surfaces of positive charges and surfaces of negative charges. In the description below, thin film regions 2711 are referred to as the first thin film regions, and thin film regions 2721 are referred to as the second thin film regions. Covering layers 2712 are referred to as the first covering layers, which are formed by reaction between the first thin film regions with a first material. Covering layers 2722 are referred to as the second covering layers, which are formed by reaction between the second thin film regions with a second material.

In some embodiments, the first thin film regions can include thin films of metal oxides or metals, as described above. Then the metal oxides or metals can receive a treatment and be exposed to phosphonic acids, such as PVPA (Polyvinylphosphonic acid). In some embodiments, the treatment can be carried out at a temperature ranging from 80° C. to 100° C. for 1-3 minutes. For example, the treatment can be carried out at 90 C for 2 minutes. This treatment can form a hydrophilic covering layer.

In some embodiments, the metal oxides or metals can receive a treatment be exposed to phosphates in a SAM (self-assembled monolayer) process. For example, a SAM process using ammonium salt of hydroxy dodecyl phosphate, $OH-DDPO_4(NH_4)_2$, can form a hydrophobic covering layer with a contact angle of about 110 degrees. In another example, a SAM process using 12-Hydroxy dodecyl phosphate, $(OH-DDPO_4)$, can form a hydrophiliic covering layer with a contact angle of about 50 degrees. In still other examples, a SAM process using a mixture of the different phosphate compounds can form a covering layer with different hydrophobicity, with contact angles ranging from 50 to 110 degrees. Further, with suitable combination of different phosphates, a covering layer with different hydrophobicity can be formed, with contact angles that can ranges from, for example, 20 to 130 degrees.

After the first covering layers formed on the metal oxides or metals thin films, a second covering layer can be formed selectively on the regions of the second thin film regions of, e.g., inorganic silicon oxide. For example, a hydrophobic covering layer can be formed by treating the device in a hydrophobic silane, such as fluorinated Alkyl-Silanes, dialkyl-Silanes, etc. Alternatively, a hydrophilic covering layer can be formed by treating the device in a hydrophilic silane, such as such as Hydroxyalkyl terminated silanes, etc. With appropriate selection of the silane compounds, the second covering layer can be formed only on the second thin film regions of, e.g., inorganic silicon oxide, and not on the first covering layer already formed on the first thin film materials. Besides inorganic silicon oxide, the second thin film regions can also include materials such as silicon, silicon nitride, metals oxides, or combinations thereof.

In the process described above, the alternating first thin film regions 2610 and second thin film layer 2620 are formed in a sequence such that first thin film regions 2610 are formed on second thin film regions 2620. In some other embodiments, second thin film regions 2620 can be formed on first thin film regions 2610, as illustrated below in FIGS. 28A-28C.

Figure 28A:
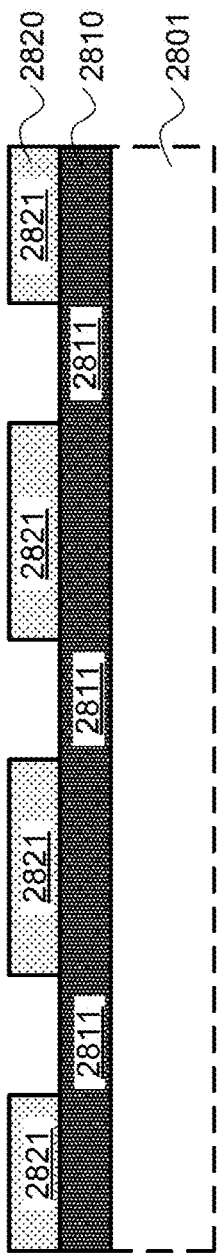
FIGS. 28A-28C are cross-sectional views illustrating a method for forming the a device structure having differential surface regions according to alternative embodiments of the invention.
Figure 28B:
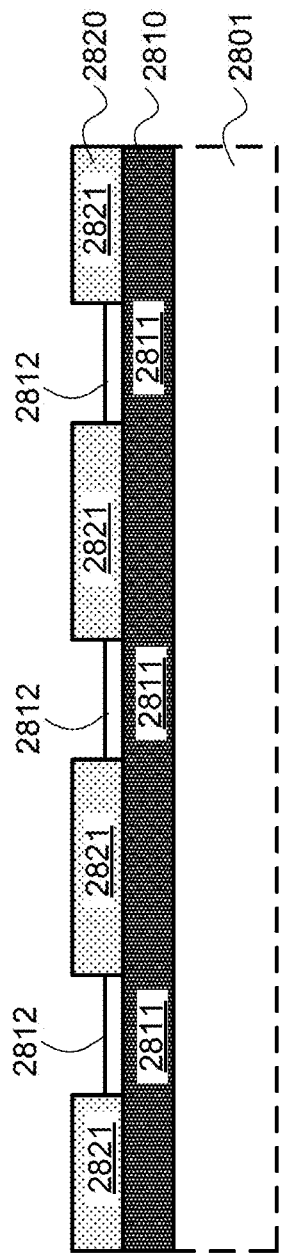
Figure 28C:
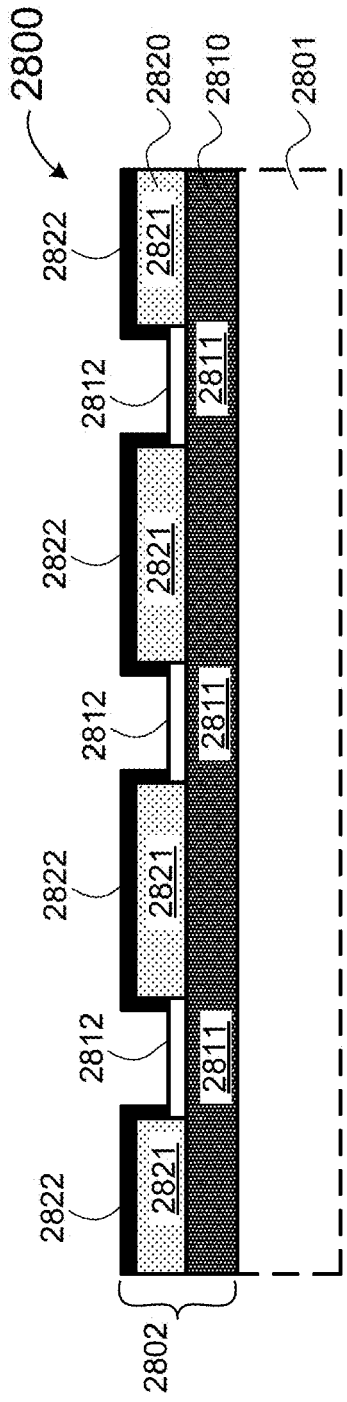

FIGS. 28A-28C are cross-sectional views illustrating a method for forming the a device structure of FIG. 26 having differential surface regions according to alternative embodiments of the invention.

FIG. 28A shows a cross-sectional view of a device structure having alternating surface regions of thin film layer 2810 and thin film layer 2820. In FIG. 28A, a surface layer including a plurality of first thin film regions 2811 and a plurality of second thin film regions 2821 are formed on substrate 2801.

The device structure in FIG. 28A is similar to that in FIG. 27D, with the first thin film layer 2810 corresponding to the first thin film layer 2710 in FIG. 27D, and the second thin film layer 2820 corresponding to the second thin film layer 2720 in FIG. 27D. One difference between the structures in FIGS. 27D and 28A is that the first thin film layer 2810 is below second thin film layer 2820. The device structure in FIG. 28A can be formed using a similar process as described in FIGS. 27A-27C, with the sequence of thin film layer formation reverse.

FIG. 28B shows a covering layer 2812 selectively formed on thin film regions 2811. The selective covering layer formation is by exposing the device structure to a suitable first material, such that covering layer 2812 is formed on the top surfaces of the thin film regions 2810, but not on the top surfaces of the thin film regions 2820. The treatment process and annealing process are similar to those described in connection with FIG. 27E, with covering layer 2812 corresponding to covering layer 2712 in FIG. 27E.

FIG. 28C shows a second covering layer 822 selectively formed on the top surfaces of the second thin film regions 2821. The selective covering layer formation is by exposing the device structure to a suitable second material, such that covering layer 222 is formed on the top surfaces of the thin film regions 2821, but not on the top surfaces of thin film region 2811 with covering layer 2812. The treatment process is similar to that described in connection with FIG. 27F. After the process with the second material, FIG. 28C shows a cross-sectional view of a device structure 2800, having a surface layer 2802 with differential surface regions 2812 and 2822. As shown in FIG. 28C, device structure 2800 includes a substrate 2801. Surface layer 2802 including a plurality of first thin film regions 2811 and a plurality of second thin film regions 2821 are disposed on substrate 2801.

A first covering layer 2812 is formed on the top surfaces of the first thin film regions 2811, and a second covering layer 2822 is formed on the top surfaces of the second thin film regions 2821. In this embodiment, a differential surface layer is formed by alternating regions of first covering layer 2812 and regions of second covering layer 2822.

In alternative embodiments, the processes illustrated in FIGS. 27A-27F and FIGS. 28A-28C can also be modified. For example, the sequence of surface layer formation can be reversed with proper selection of thin film materials and the compounds for surface treatment. In some embodiments, in FIGS. 27D-27F, covering layers 2722 can be formed on thin film regions 2721 in the structure of FIG. 27D first, and then covering layer 2712 can be formed on thin film regions 2711. Similarly, in FIGS. 28A-28C, covering layers 2822 can be formed on thin film regions 2821 in the structure of FIG. 28A first, and then covering layer 2812 can be formed on thin film regions 2811.

Although the processes described herein are described with respect to a certain number of steps being performed in a certain order, it is contemplated that additional steps may be included that are not explicitly shown and/or described. Further, it is contemplated that fewer steps than those shown and described may be included without departing from the scope of the described embodiments (i.e., one or some of the described steps may be optional). In addition, it is contemplated that the steps described herein may be performed in a different order than that described.

For example, the first and second thin film regions can be either metal or metal oxide, or silicon oxide. Even though in the above example, a covering layer formed by phosphonic acid or phosphate on metal oxides is formed first, followed by a covering layer formed by silane on silicon oxide. In some embodiments, a first covering layer can be formed first by silane on silicon oxide, and then a second covering layer can be formed by phosphonic acid or phosphate on metal oxides. In some embodiments, the treatment by phosphonic acid or phosphate on metal oxides is followed by an annealing process as described above.

VI. Bio Sensors for Biological or Chemical Analysis and Methods of Manufacturing the Same CMOS image sensors find use in electronic imaging devices, including digital cameras, medical imaging equipment, radar devices, and the like. Using integrated circuits and a series of photodiodes, CMOS image sensors can capture light and convert it into electrical signals.

CMOS image sensors are typically implemented on chips. The chips may have an amplifier for each pixel. Although the inclusion of many amplifiers in a chip may result in less area for the capture of light, other components can be integrated onto the chip to direct more light into the photodiodes. For example, microlenses may be placed in front of the photodiodes to direct light into the photodiodes. To further increase the amount of light that hits the photodiodes, backside illumination (BSI) can be used. BSI effectively places the photodiodes closer to the light source, instead of under and between the integrated circuit wiring, reducing destructive interference. BSI CMOS sensors also have other advantages. For example, BSI CMOS sensors may have low operating voltage, low power consumption, high efficiency, and low noise.

BSI CMOS image sensors typically have two functional areas: a light sensing area and an electronic circuit area. The light sensing area includes the photodiodes arranged in an array, coupled to metal-oxide-semiconductor (MOS) transistors that detect the light intensity. The electronic circuit area provides connections between the MOS transistors and external connections, such as to other devices for processing the data from the MOS transistors.

In practice, a BSI CMOS image sensor employs filters that divide incident light into bands of light of different wavelengths. The light is received by the photodiodes on a substrate and transformed into electrical signals of different intensity. For example, an incident beam may be divided into red, green, and blue light and received by respective photodiodes for each color. Each photodiode transforms the detected light intensity into electrical signals. This is accomplished by the photodiode accumulating a charge. For example, the higher the intensity of the light, the higher the charge accumulated in the photodiode. The accumulated charge can then be correlated to a color and brightness.

In addition to the uses described above, CMOS image sensors may also be used for biological or chemical analysis. For such analysis, a biological or chemical sample may be placed above a photodiode, and light emitted by the biological or chemical sample may be directed to the photodiode. The fluorescence or chemiluminescence of the sample can be detected by the photodiode, and a color and brightness can be determined. This color and brightness may be used to identify the biological or chemical sample.

Embodiments of the invention address the drawbacks associated with previous approaches by providing an improved biosensor for biological or chemical analysis. According to embodiments of the invention, BSI CMOS image sensors can be used to effectively analyze and measure fluorescence or chemiluminescence of a sample. This measured value can be used to help identify a sample. Embodiments of the invention also provide methods of manufacturing an improved biosensor for biological or chemical analysis. As used herein, the term "biosensor" may be used to refer to an apparatus for determining a light emitting substance within or attached to a biological molecule, particularly a nucleic acid macromolecule exemplified by DNA and branched or otherwise derivatized nucleic acids. As used herein, the term "nucleic acid macromolecule" may refer to, for example, DNB or single strand embodiments.

According to some embodiments of the invention, a biosensor is provided. The biosensor comprises a backside illumination complementary metal-oxide-semiconductor (CMOS) image sensor. The backside illumination CMOS image sensor includes an electronic circuit layer and a photo sensing layer over the electronic circuit layer. The photo sensing layer includes a substrate layer and a photodiode in contact with the electronic circuit layer. A light receiving surface is defined by a surface of the photodiode opposite to the electronic circuit layer. The biosensor can also include a color filter material over the photodiode. The biosensor can also include a spot or well above the color filter material that is sized and functionalized to receive a nucleic acid macromolecule, and to absorb light from the nucleic acid macromolecule or to pass the light to the light receiving surface from the nucleic acid macromolecule.

A method of manufacture according to some embodiments comprises providing a backside illumination complementary metal-oxide-semiconductor (CMOS) image sensor. Providing the backside illumination CMOS image sensor includes providing an electronic circuit layer and providing a photo sensing layer over the electronic circuit layer. The photo sensing layer includes a substrate layer and a photodiode in contact with the electronic circuit layer. A light receiving surface is defined by a surface of the photodiode opposite to the electronic circuit layer. The method can also include depositing a color filter material over the photodiode. The method can also include providing a spot or well above the color filter material that is sized and functionalized to receive a nucleic acid macromolecule, and to absorb light from the nucleic acid macromolecule or to pass light to the light receiving surface from the nucleic acid macromolecule.

A method of DNA sequencing according to some embodiments comprises iteratively performing a process that may include labeling a nucleic acid macromolecule with a fluorescent label that identifies a nucleotide base at a particular position in the nucleic acid macromolecule. The process further includes detecting the fluorescent label associated with the nucleic acid macromolecule. Detecting the fluorescent label includes illuminating the nucleic acid macromolecule with excitation light. The nucleic acid macromolecule absorbs the excitation light and transmits emitted light through a color filter and onto a photodiode of a backside illumination complementary metal-oxide-semiconductor (CMOS) image sensor. Detecting the fluorescent label further includes measuring at least one parameter of the emitted light received at the photodiode. Detecting the fluorescent or chemiluminescent label further includes correlating the at least one parameter of the emitted light to the fluorescent label. The process further includes removing the fluorescent label from the nucleic acid macromolecule. Without limitation, the biosensors of embodiments of the invention may be used to carry out sequencing-by-synthesis (SBS), sequencing-by-ligation, cPAL sequencing, pyrosequencing, and combinations of the foregoing.

FIGS. 29-42 describe various stages of manufacture of a biosensor according to embodiments of the invention. Other embodiments of manufacture and configuration will be evident from this description to those of skill in the art. It is therefore intended that the following description be descriptive but not limiting.

For ease of reading, the text below is organized into sections. However, it will be understood that a description of subject matter in one section (e.g., descriptions of macromolecules, filters, sequencing methods, etc.) may also apply to subject matter in other sections.

Biosensors according to embodiments of the invention are not limited to a particular use. In one aspect, the biosensors of embodiments of the invention find particular use for massively parallel DNA sequencing. DNA sequencing technologies are well known (see, e.g., Drmanac et al., 2010, "Human genome sequencing using unchained base reads on self-assembling DNA nanoarrays," Science 327:78-81; Shendure & Ji, (2008, "Next-generation DNA sequencing," Nature Biotechnology 26:1135-45) and are therefore described only in general terms in sections below. The following paragraphs provide a brief initial discussion of sequencing and associated terminology so that certain features of the biosensors described below may be more easily understood.

A variety of DNA sequencing methods are known. In many approaches, large molecules (e.g., genomic DNA) are broken into many smaller fragments, each having a characteristic DNA sequence. In array based technologies, the fragments are distributed to an array of positions on a substrate so that each position in the array contains a DNA fragment with a single characteristic sequence. Sequence information ("reads") is obtained from DNAs at each of thousands, or more often, millions, of positions simultaneously and assembled by a computer. In most sequencing approaches, the fragments are amplified prior to sequence determination. The amplification may occur prior to the positioning of the fragments at each position, after the positioning of the fragments at each position, or both before and after positioning. The amplification step(s) produce "amplicons" which serve as "templates" in a sequencing process. Thus, for illustration, amplification may use RCA to produce a single-stranded concatemer (e.g., a DNA nanoball) at each position on the array or use bridge PCR to produce a clonal population (or cluster) of DNA molecules with the same sequence at each position.

It will be understood that reference to a "DNA macromolecule," and the like, encompasses DNA nanoballs, branched structures, and clustered clonal populations (i.e., more than a single molecule) or their precursors. In addition, a "DNA macromolecule," and the like, may encompass auxiliary DNA molecules such as primers and growing strands produced by primer extension or other processes encompasses. In many sequencing technologies, it is the auxiliary DNA molecules that comprise (or are "labeled" with) a detectable (e.g., fluorescent or chemiluminescent) dye that emit light detected by photodiodes of the biosensor. Thus, a phrase such as "illuminating the nucleic acid macromolecule with an excitation light source and detecting light emitted from the macromolecule" will be understood to encompass "exposing a DNA nanoball or clonal cluster and associated labeled auxiliary molecules with an excitation light source and detecting light emitted from the dyes of the labeled auxiliary molecules."

In array-based sequencing methods, and the biosensors of embodiments of the invention, DNA macromolecules are positioned on a substrate in wells or on "spots." The wells or spots are able to receive and retain the macromolecule. Often, the spots, sometimes called "discrete spaced apart regions" or "pads", comprise a substrate functionalized to receive a nucleic acid macromolecule and the spots are separated by areas that are "inert" in the sense that DNA macromolecules do not bind such areas. For example, and without limitation, see Drmanac 2010, supra. "Wells" are a type of spot comprising walls that form a boundary or barrier to the DNA macromolecules. Except where clear from context, reference to "spots" below may include wells.

In biosensors of embodiments of the invention, spots generally have uniform dimensions and are organized as a regular (i.e., not random) array. The spots of an array are generally organized in a rectilinear pattern, often in columns and rows, but other regular patterns may be used (e.g., a spiral). The spots of an array may have characteristic dimensions, pitch, and density. The spots themselves may be circular, square, hexagonal or other shape. In the discussion below, the spots are generally assumed to be circular (i.e., can be described as having a diameter). It will be understood that reference to a "diameter" can also refer to linear dimensions of other shaped spots (e.g., diagonal, length or width). Thus, as used herein, "linear dimension" can refer to a diameter of a circle, width of a square, diagonal, and the like. In the context of biosensors of embodiments of the invention, the size of the spots is meaningful in two ways. First, the spots may be sized and/or functionalized in a way that limits occupancy to a single target sequence. This may be a single DNA nanoball (a concatemer of a single target sequence) or a clonal cluster with a single target sequence. See, e.g., U.S. Pat. No. 8,133,719 and U.S. Pat. App. Pub. No. 2013/0116153, both incorporated by reference in their entireties for all purposes. Secondly, generally the spots may be sized and positioned relative to underlying photodiodes so that each photodiode receives emitted light from a single spot. In some embodiments, an array of spots may be positioned over an array of corresponding photodiode(s) (and/or color filters) with a 1 to 1 correlation. That is, light emitted from an, e.g., DNA macromolecule at individual spot passes into an underlying filter and light not blocked by the filter is detected by a single photodiode associated with the filter, or light emitted from an, e.g., DNA macromolecule, at individual spot passes into a plurality of underlying filters, each associated with a filter (specific for particular wavelengths), each associated with a single photodiode, and light not blocked by a filter is detected by the associated photodiode. Thus, as also discussed below, in some embodiments, light emitted from a single spot may be detected by more than one photodiode (e.g., 2, 3, 4, etc.) photodiodes. In these embodiments, a group of multiple photodiodes associated with a single spot may be referred to as a "unit cell" of photodiodes. The spots and filters (e.g., single filters or unit cells) may be arranged in the biosensor such that each photodiode in the unit cell receives light emitted from the same single spot. In addition, in some embodiments, the area of the light receiving surface of a photodiode, or combined area of the light receiving surfaces of multiple photodiodes associated with the same spot, is less than the area of the spot (from which light is emitted). Put another way, the spot may be smaller than the underlying photodiode(s) such that the boundary of the spot, if projected onto the light receiving surface of the photodiode(s), is contained within the light receiving surface.

As is well known, nucleic acid sequencing generally involves an iterative process in which a fluorescent or chemiluminescent label is associated in a sequence in a specific way with the DNA template (amplicon) being sequenced, the association is detected, and the label is removed in the sense that it no longer emits a signal. See, e.g., U.S. Pat. App. Pub. No. 2016/0237488; U.S. Pat. App. Pub. No. 2012/0224050; U.S. Pat. Nos. 8,133,719; 7,910, 354; 9,222,132; 6,210,891; 6,828,100, 6,833,246; and 6,911, 345, herein incorporated by reference in their entireties. Thus it will be appreciated that, for example, "labeling a nucleic acid macromolecule with a fluorescent label" may refer to associating a labeled auxiliary molecule(s) with a DNA template immobilized on a spot.

Figure 29:
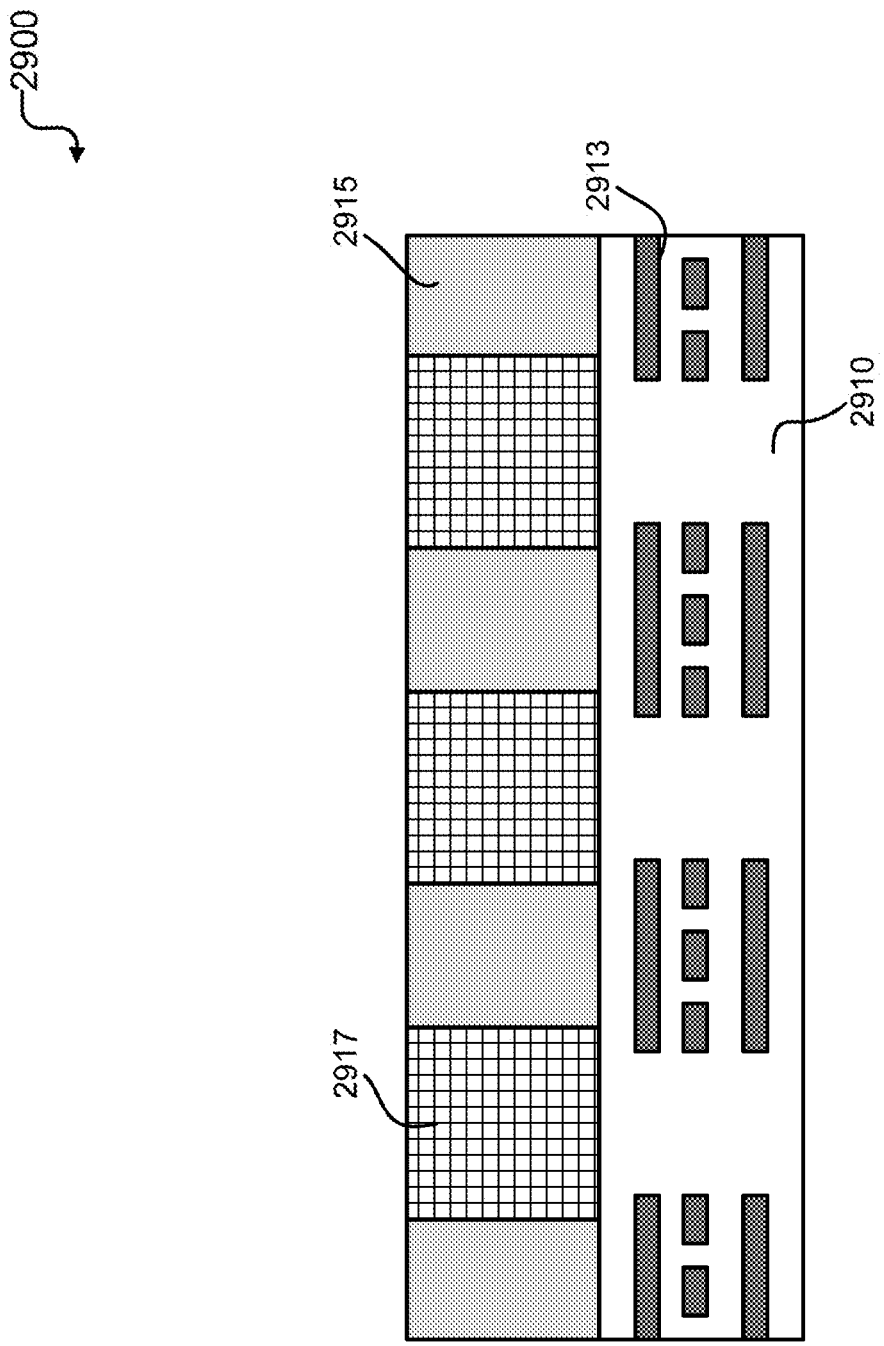
FIG. 29 is a cross-sectional view of a backside illumination CMOS image sensor, according to some embodiments

Turning now to the drawings, FIG. 29 is a cross-sectional view of a backside illumination (BSI) CMOS image sensor 2900 according to some embodiments. The BSI CMOS image sensor 2900 may include a first dielectric layer 2910. Although described as being dielectric, it is contemplated that the first dielectric layer 2910 may include any suitable electrically insulating material. The first dielectric layer 2900 may include metal wiring 2913. The metal wiring 2913 may include integrated circuit materials and external connections. Together, the first dielectric layer 2900 and the metal wiring 2913 may be collectively referred to herein as an "electronic circuit layer" of the BSI CMOS image sensor.

A substrate layer 2915 may be provided over the first dielectric layer 2910 and the metal wiring 2913. The substrate layer 2915 may be made of any suitable material, such as, for example, silicon, III-V group on silicon, graphene-on-silicon, silicon-on-insulator, combinations thereof, and the like. The substrate layer 2915 may include openings in which light sensing components (e.g., photodiodes 2917) may be positioned. Although described herein with respect to photodiodes 2917, it is contemplated that any suitable light sensing component may be used. The photodiodes 2917 may be configured to convert measured light into current. Photodiodes 2917 may include the source and drain of a MOS transistor (not shown) that may transfer the current to other components, such as other MOS transistors. The other components may include a reset transistor, a current source follower or a row selector for transforming the current into digital signals, and the like. Together, the substrate layer 2915 and the photodiodes 2917 may be collectively referred to herein as a "photo sensing layer" of the BSI CMOS image sensor.

The photodiodes 2917 may be in contact with metal wiring 2913 to communicate the digital signals to external connections via the metal wiring 2913. In the BSI CMOS image sensor 2900 illustrated in FIG. 29, the light receiving surface is positioned at the top of the photodiodes 2917 (i.e., on a surface not in contact with the electronic circuit layer and opposite to the electronic circuit layer), and incident light is received by the photodiodes 2917 at this light receiving surface.

Figure 30:
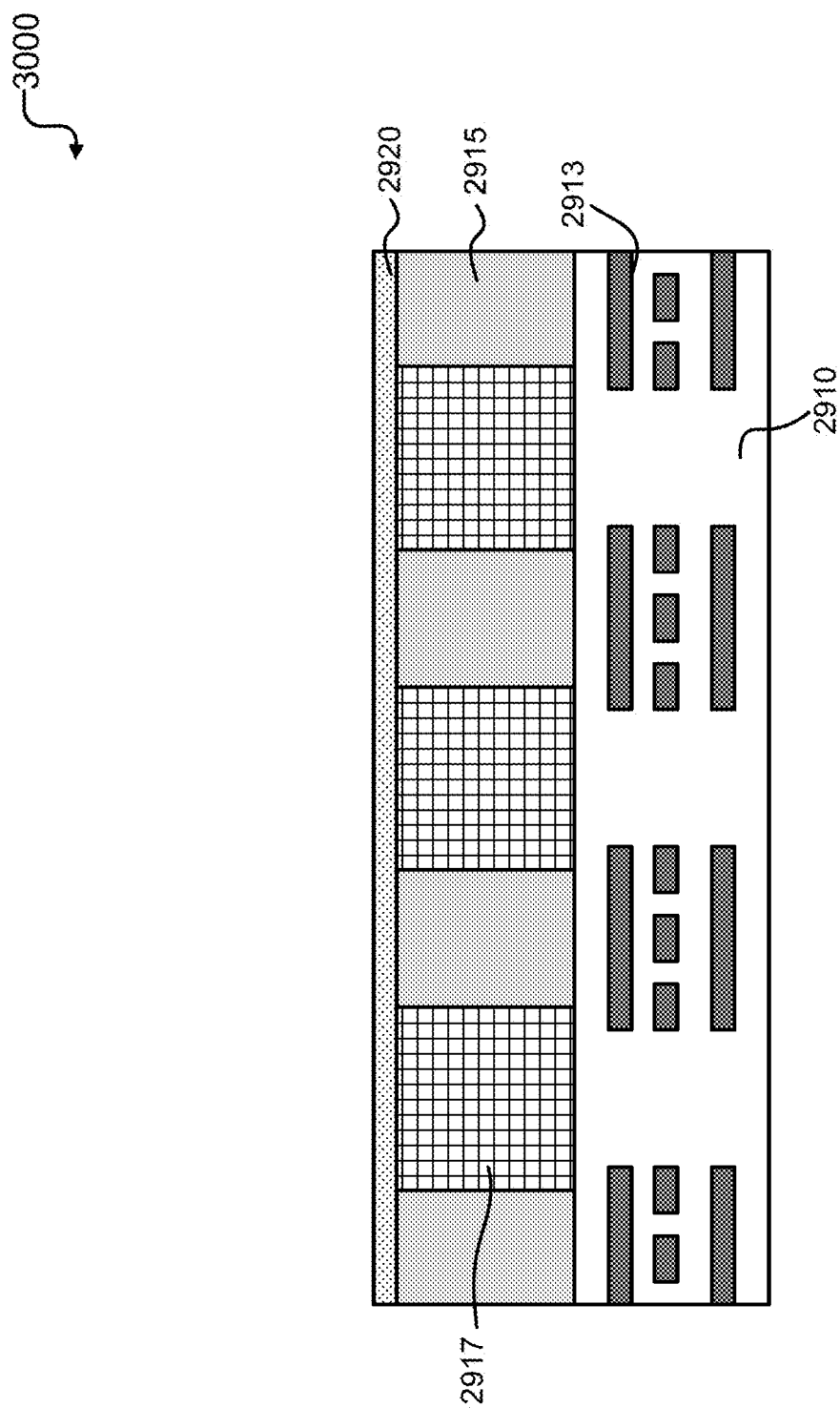
FIG. 30 is a cross-sectional view of a backside illumination CMOS image sensor with a first passivation layer, according to some embodiments.
Figure 31:
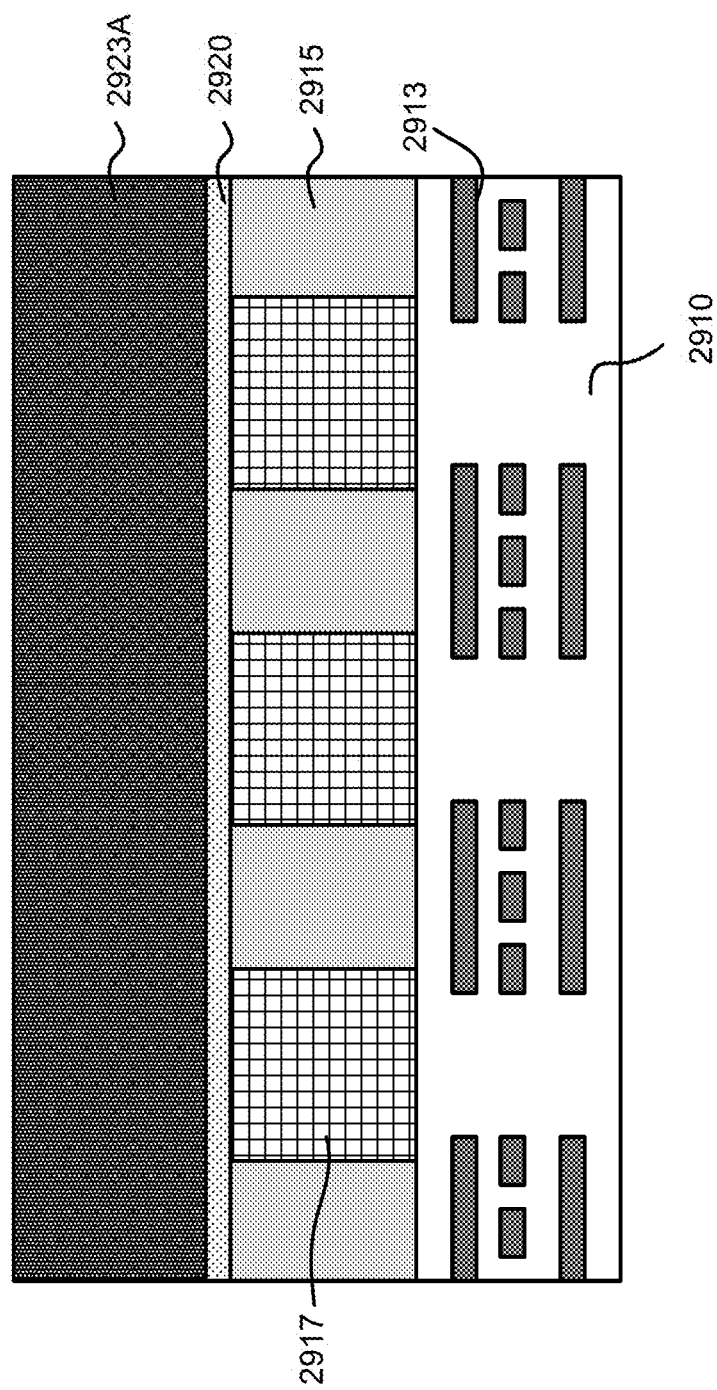
FIG. 31 is a cross-sectional view of a backside illumination CMOS image sensor with a first metal layer, according to some embodiments.

According to FIG. 30, in order to construct a biosensor 3000, a first passivation layer 2920 may be deposited by conventional semiconductor processing techniques (e.g., low temperature plasma chemical vapor deposition) on the substrate layer 2915 and the photodiodes 2917 of the BSI CMOS image sensor 2900. The first passivation layer 2920 may include any suitable protective material. For example, the first passivation layer 2920 may include materials such as silicon, oxide, metals, combinations thereof, and the like. The first passivation layer 2920 may act as an etch stop for later etching steps, as described further herein. The first passivation layer 2920 may alternatively or additionally act to protect the active device (i.e., the backside illumination CMOS sensor). The first passivation layer 2920 may alternatively or additionally act to protect photodiodes 2917 from wear caused by frequent use. The first passivation layer 2920 may be transparent. In one example, the first passivation layer 2920 may have a thickness of 100 nanometers or less.

A. Biosensor 3000 of FIG. 30

FIG. 30 illustrates a biosensor 3000 that may be used for biological or chemical analysis (e.g., to detect the chemiluminescence of a macromolecule or macromolecular complex), according to some embodiments. The biosensor 3000 includes a backside illumination CMOS image sensor 2900. The backside illumination CMOS image sensor 2900 includes an electronic circuit layer (comprised of the first dielectric layer 2910 and the metal wiring 2913) and a photo sensing layer over the electronic circuit layer (comprised of a substrate layer 2915 and photodiodes 2917). The photodiodes 2917 may be in contact with the electronic circuit layer such that electronic signals may be transmitted from the photodiode 2917 to the electronic circuit layer, and in some embodiments, to an external device. A light receiving surface is defined by a surface of the photodiodes 2917 that is opposite to the electronic circuit layer (i.e., the surface in contact with the first passivation layer 2920).

The biosensor 3000 may further include the first passivation layer 2920 over the backside illumination CMOS image sensor 2900, and spots or wells (not shown) formed over or in the first passivation layer 2920 on or over which chemical or biological samples may be placed for analysis. In some embodiments, the biosensor 3000 may be adapted for detecting an optical signal (e.g., fluorescent or chemiluminescent emission) from a corresponding array of biomolecules, where individual biomolecules may be positioned over (e.g., in spots or wells) one or more photodiodes such that the one or more photodiodes receive light from the biomolecule, as discussed in greater detail below.

Various further embodiments for constructing biosensors using a backside illumination CMOS sensor 3000 may now be described. According to FIG. 31, a first metal layer 2923A may be deposited by conventional semiconductor processing techniques on the first passivation layer 2920 of biosensor 3000 (e.g., by metal deposition techniques). The first metal layer 2923A may include any suitable metal material. For example, the first metal layer 2923A may include materials such as tungsten, aluminum, gold, copper, combinations or alloys thereof, and the like. In some embodiments, the first metal layer 2923A may be a thick layer, e.g., thicker than the first passivation layer 2920. For example, the first metal layer 2923A may be up to 3 micrometers.

Figure 32:
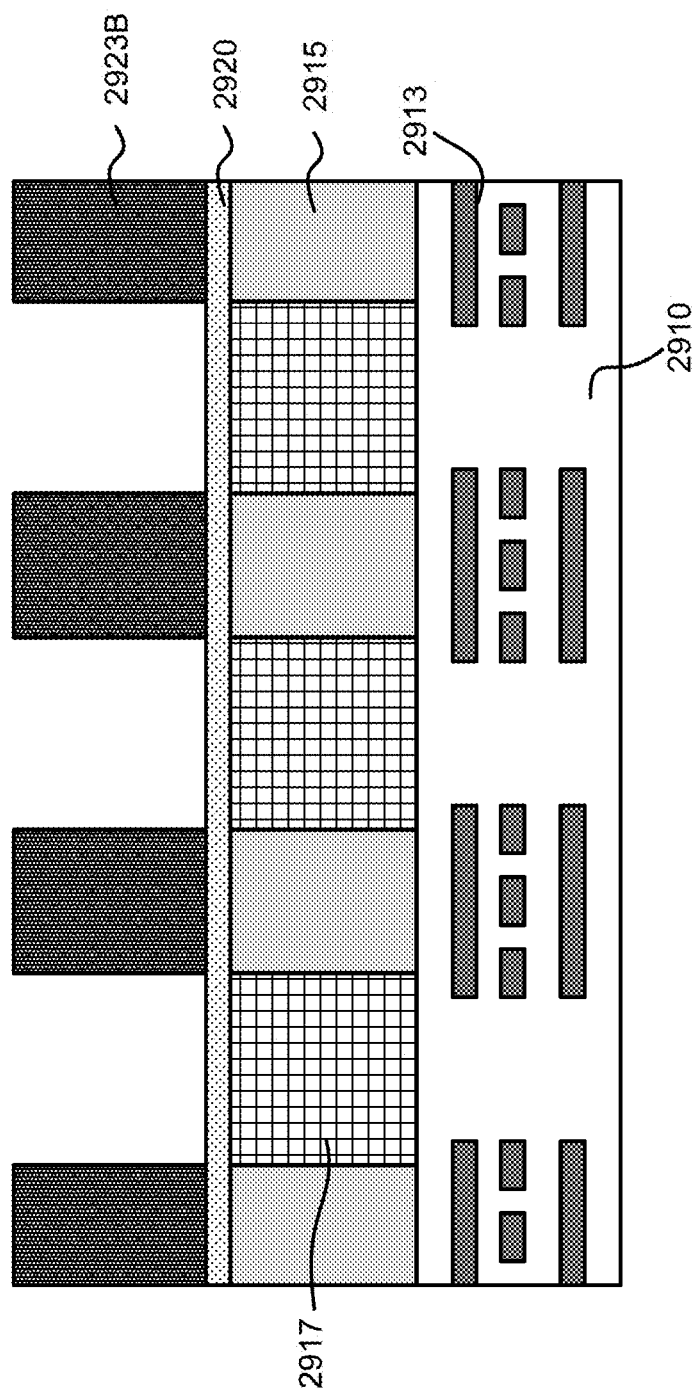
FIG. 32 is a cross-sectional view of a backside illumination CMOS image sensor with an etched first metal layer, according to some embodiments.

According to FIG. 32, the first metal layer 2923A may be etched to provide first openings above the photodiodes 2917, leaving first metal layer 2923B. The first metal layer 2923A may be etched by any suitable process, such as, for example, wet etching, dry etching, combinations thereof, and the like. It is contemplated that etching the first metal layer 2923A may involve use of a mask, for example. The etching may be completed using any of a variety of materials, such as, for example, acids (e.g., hydrochloric acid, hydrofluoric acid, nitric acid, etc.), alkali with oxidizers, combinations thereof, and the like. It is contemplated that the type of acid needed to etch the first metal layer 2923A may depend on the material used for forming the first metal layer 2923A. In some embodiments, the first openings may be aligned center to center with the photodiodes 2917, maximizing efficiency of the photodiodes 2917 in later use. A mask (not shown) may define the openings over the photodiodes 2917, leaving first metal layer 2923B remaining, and the first passivation layer 2920 may act as an etch stop when etching the openings in the first metal layer 2923A. As described herein, the pillars of the first metal layer 2923B may separate light received by separate color filters and may reflect back light intended for a certain color filter back into that color filter or into the corresponding photodiode 2917.

Figure 33:
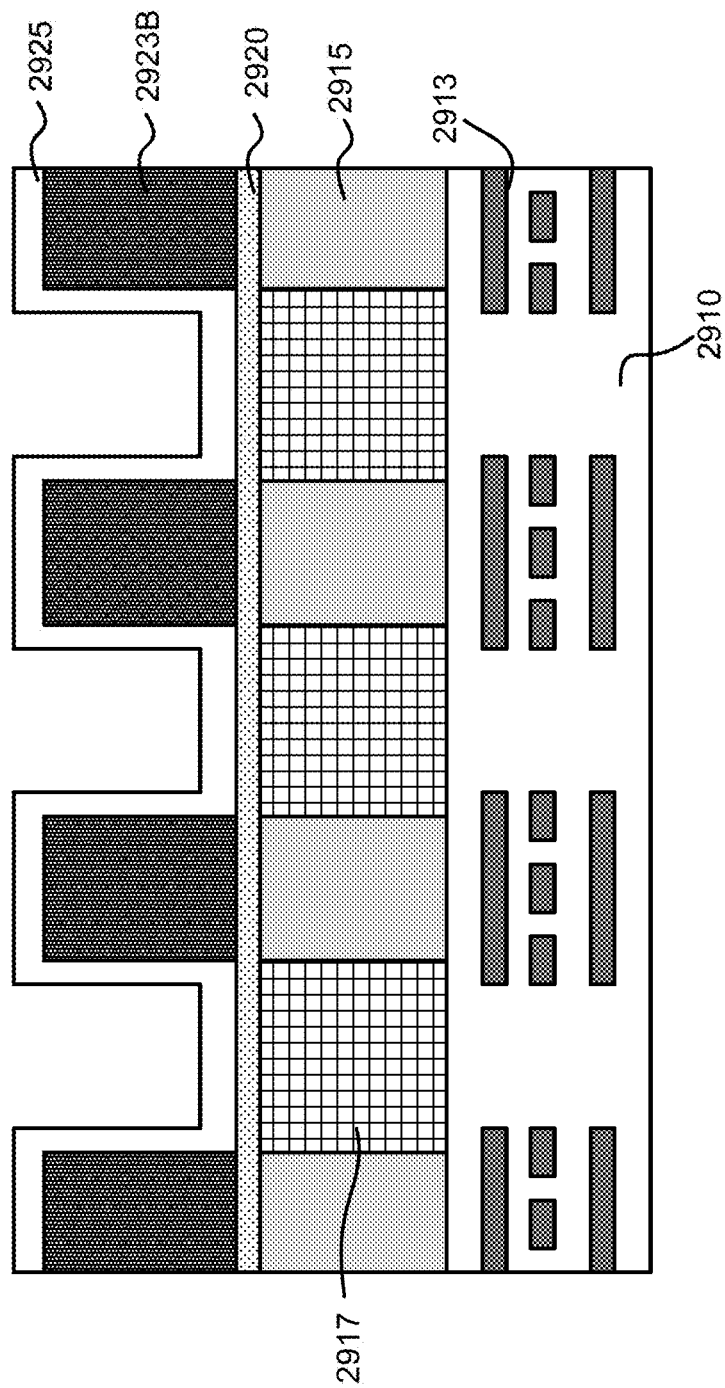
FIG. 33 is a cross-sectional view of a backside illumination CMOS image sensor with a dielectric layer, according to some embodiments.

According to FIG. 33, a second dielectric layer 2925 may be deposited over the first metal layer 2923B and in the first openings by conventional semiconductor processing techniques. In some embodiments, the second dielectric layer 2925 may be formed on all exposed sides of the first metal layer 2923B. Although described as being dielectric, it is contemplated that the second dielectric layer 2925 may include any suitable electrically insulating material, such as silicon nitride, tantalum oxide, combinations thereof, and the like. The second dielectric layer 2925 may be formed of a same or different material than the first dielectric layer 2910.

Figure 34:
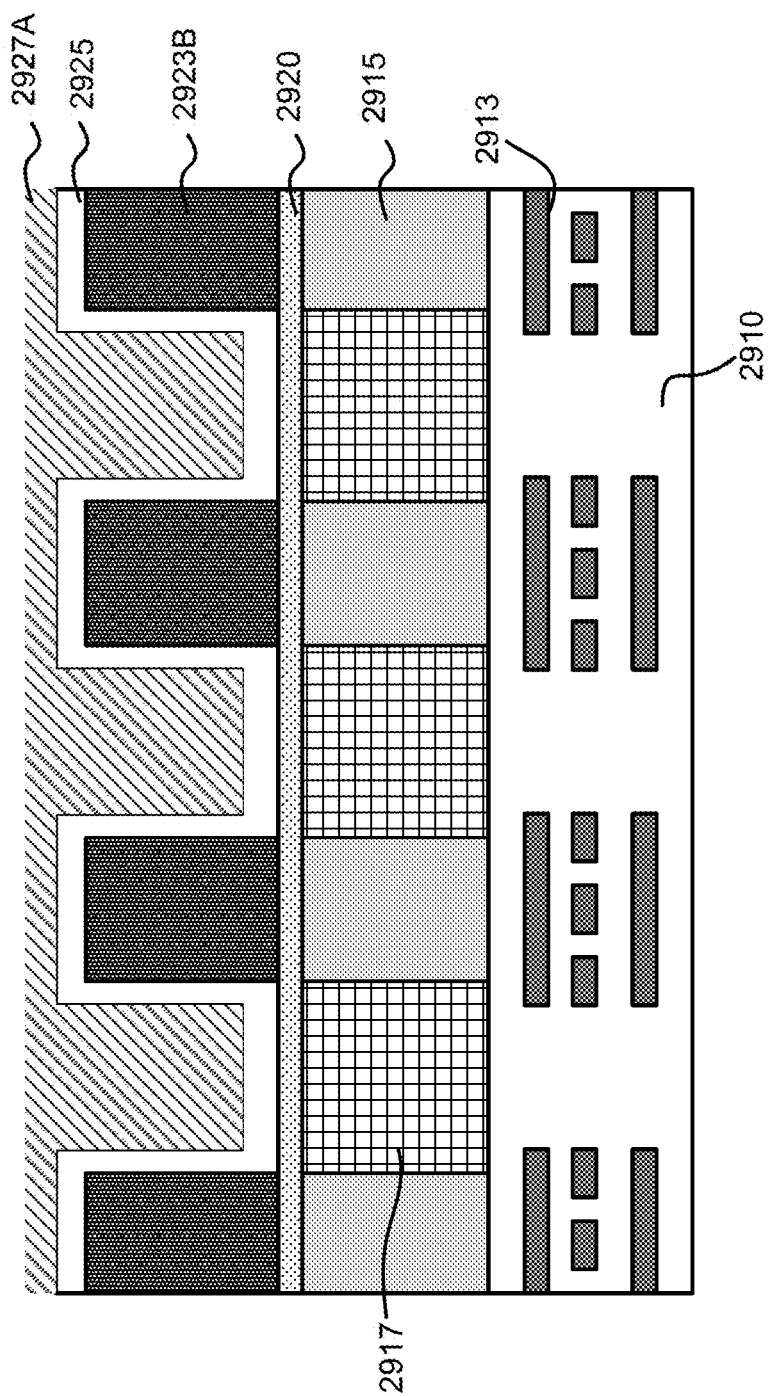
FIG. 34 is a cross-sectional view of a backside illumination CMOS image sensor with a color filter layer, according to some embodiments.
Figure 35:
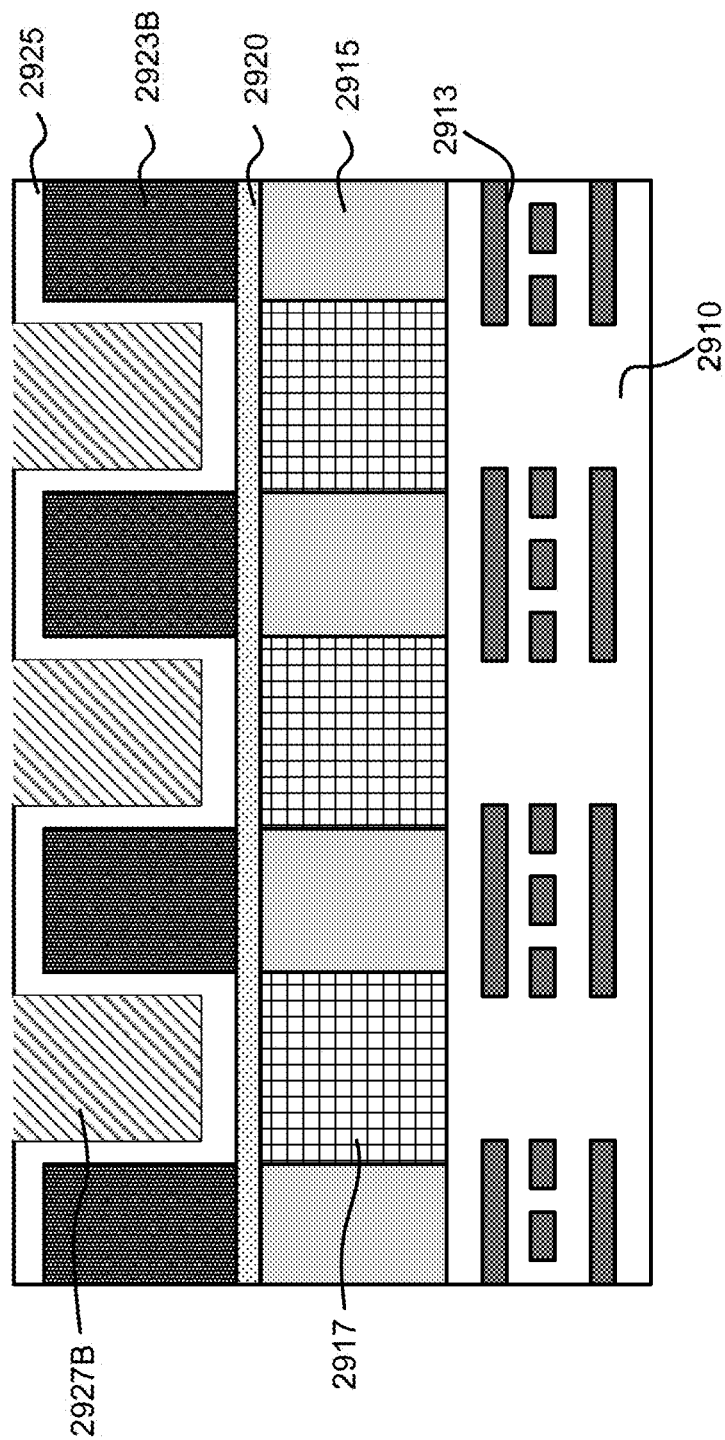
FIG. 35 is a cross-sectional view of a backside illumination CMOS image sensor with a planarized color filter layer, according to some embodiments.

According to FIG. 34, color filter material 2927A may be deposited over the second dielectric layer 2925. In some embodiments, color filter material 2927A may be deposited by spin coating. Color filter material 2927A fills the openings created by second dielectric layer 2925. In this embodiment, color filter material 2927A is also deposited on the portions of second dielectric layer 2925 between the openings. Thus, according to FIG. 35, the excess color filter material 2927A above the openings of the second dielectric layer 2925 may be removed, such as by, for example, chemical-mechanical planarization (CMP), leaving color filter material 2927B in the openings of the second dielectric layer 2925.

However, it is also contemplated that in some embodiments, the color filter material may be formed using an alternative process. For example, as in FIG. 35, color filter material 2927B may be selectively deposited only in the openings of the second dielectric layer 2925, such that more than one (e.g., 2, 3 or 4) different color filter material 2927B may be placed above the photodiodes 2917. In some applications, each different color filter material 2927B may be associated with a separate photodiode 2917.

The color filter material 2927B may include, for example, a pigment-based polymer, a pigment-based dye, a dye-based polymer, a resin or other organic based material, combinations thereof, and the like. Color filter material 2927B may be necessary for the biosensor, for example, because the photodiodes 2917 may alone detect light intensity with little or no wavelength specificity, and thus cannot separate color information.

Color filter material 2927B may include blue filter material, red filter material, green filter material, emerald filter material, cyan filter material, yellow filter material, magenta filter material, white filter material, combinations thereof, and the like. Thus, the color filter material 2927B may filter incident light by wavelength range, such that the separate filtered intensities include information about the color of light. For example, red color filter material 2927B may give information about the intensity of light in red wavelength regions. Blue color filter material 2927B may give information about the intensity of light in blue wavelength regions. Green color filter material 2927B may give information about the intensity of light in green wavelength regions, and so on and so forth.

Figure 42B:
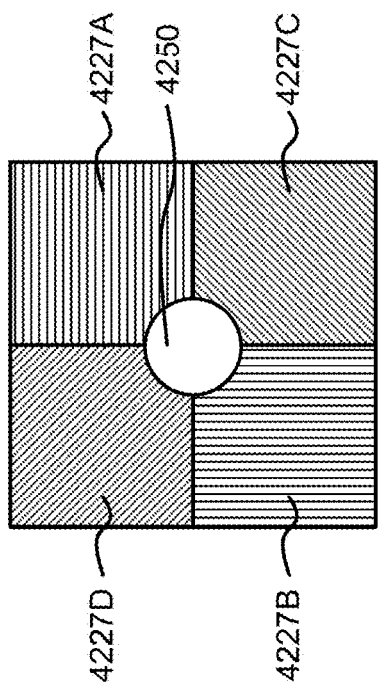
FIG. 42B is a top view of a four-channel color filter that may be used in a biosensor, according to some embodiments.
Figure 42A:
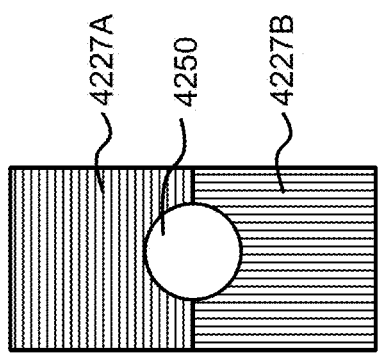
FIG. 42A is a top view of a two-channel color filter that may be used in a biosensor, according to some embodiments.

In some embodiments, color filter material 2927B may include material of a single color. For example, each of the color filter materials 2927B may be red. In some embodiments, color filter material 2927B may include material of different colors, with each color filter material 2927B corresponding to a separate photodiode 2917. For example, one color filter material 2927B may be red, and a neighboring color filter material 2927B may be green. FIG. 42A illustrates such an embodiment, in which a two-channel color filter is used. In FIG. 42A, a biological or chemical sample (e.g., a DNA macromolecule) may be positioned in a spot or well 1450 such that emissions from the macromolecule enter both the red color filter material 4227B and the green color filter material 4227A (e.g., overlapping both the red color filter material 4227B and the green color filter material 4227A), and such that the emitted wavelength of light through the different colors of the color filter material may be detected. In another example, more than two surrounding color filter materials 127B may include material of different colors. FIG. 42B illustrates such an embodiment, in which a four-channel color filter is used. The four-channel color filter may include one color filter material 4227B that is red, one color filter material 4227D that is yellow, one color filter material 4227A that is green, and one color filter material 4227C that is blue. In this example, a biological or chemical sample may be placed in a spot or well 4250 at the intersection of the four color filters, such that the emitted wavelength of light through the four colors of the color filter material may be detected. In some embodiments, spot or well 4250 may lie above each of the underlying color filter materials (and corresponding photodiodes) equally, i.e., so that equal areas of each filter underlies the spot.

Figure 36A:
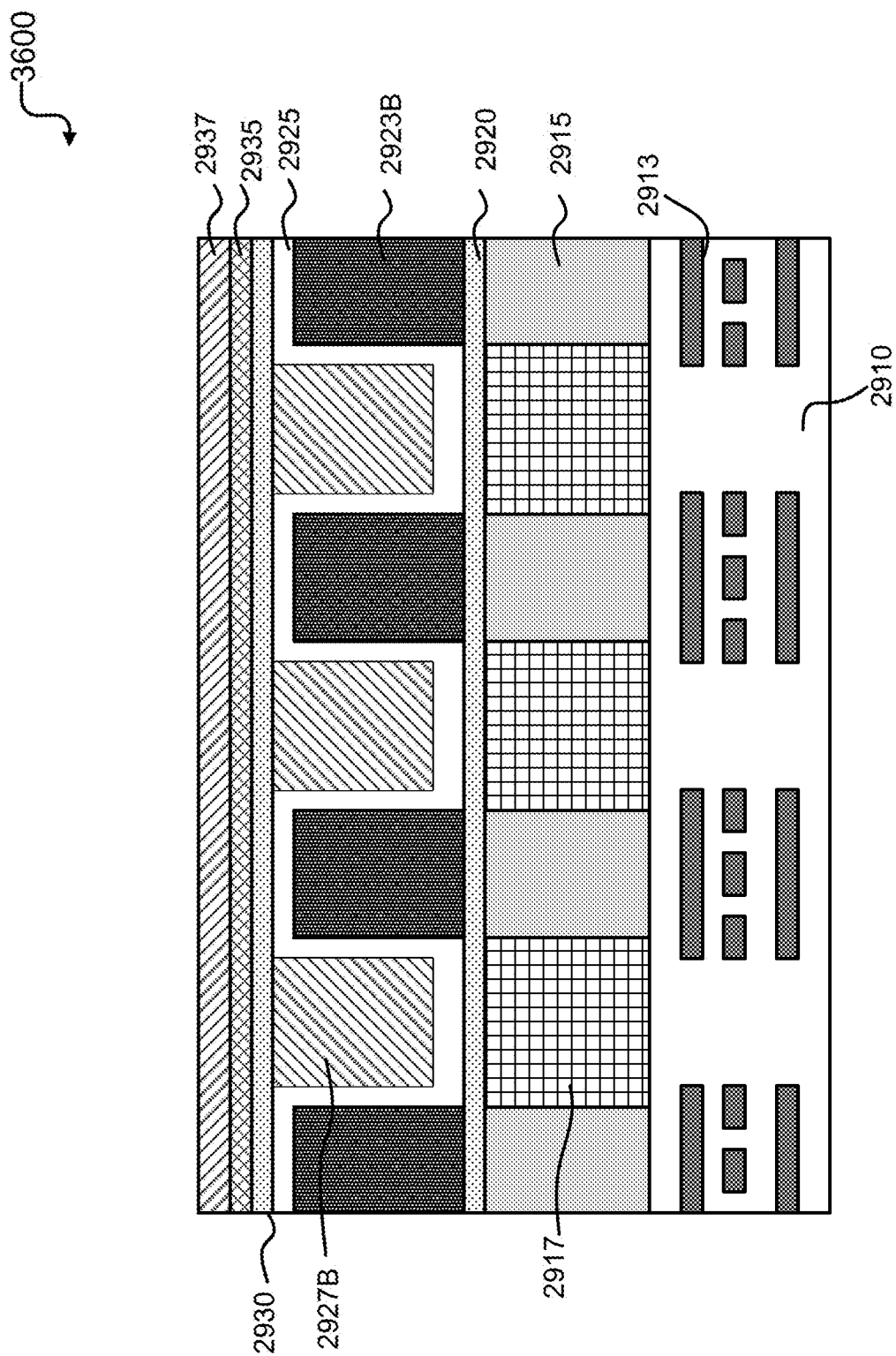
FIG. 36A is a cross-sectional view of a backside illumination CMOS image sensor with a second passivation layer, a first material layer, and a second metal layer, according to some embodiments.

FIG. 36A illustrates an embodiment in which biosensor 3600 is constructed. According to FIG. 36A, the second passivation layer 2930 may be deposited according to conventional semiconductor techniques over the second dielectric layer 2925 and the color filter material 2927B. The second passivation layer 2930 may be as described below with respect to FIG. 36B. A first material layer 2935 may be deposited over the second passivation layer 2930. The first material layer 2935 may include any suitable materials, such as silicon nitride, tantalum oxide, combinations thereof, and the like. A second material layer 2937 may be deposited over the first material layer 2935. The second material layer 2937 may include any suitable materials, such as silicon dioxide and the like. In some embodiments, the first material layer 2935 may have a refractive index that is higher than the refractive index of the second material layer 2937. In some embodiments, the first material layer 2935 may have a refractive index that is higher than the second passivation layer 2930. Thus, the embodiment of FIG. 36A may result in efficient delivery of excitation light to the light receiving surface in the case of fluorescence measurement. For example, the first material layer 2935 may form the core of an optical waveguide, thus permitting low loss transmission of excitation light. In some embodiments, biological or chemical samples may be placed on the second material layer 2937 above the photodiodes 2917 (in some embodiments, in openings or wells formed on the second material layer 2937), and their fluorescence or chemiluminescence may be measured by the photodiodes 2917, as described further herein. When measuring fluorescence in the embodiment shown in FIG. 36A, however, the excitation light may be directed sideways, along the surface of the biosensor 3600, in some examples.

B. Biosensor 3600 of FIG. 36A

Thus, FIG. 36A illustrates a biosensor 3600 that may be used for biological or chemical analysis according to some embodiments. The biosensor 3600 may include a backside illumination CMOS image sensor 2900. The backside illumination CMOS image sensor 2900 includes an electronic circuit layer (comprised of the first dielectric layer 2910 and the metal wiring 2913) and a photo sensing layer over the electronic circuit layer (comprised of a substrate layer 2915 and photodiodes 2917). The photodiodes 2917 may be in contact with the electronic circuit layer such that electronic signals may be transmitted from the photodiode 2917 to the electronic circuit layer, and in some embodiments, to an external device. A light receiving surface is defined by a surface of the photodiodes 2917 that is opposite to the electronic circuit layer (i.e., the surface in contact with the first passivation layer 2920).

The biosensor 3600 may further include the first passivation layer 2920 over the backside illumination CMOS image sensor 2900, and a first metal layer 2923B over the first passivation layer 2920. The first metal layer 2923B may also be positioned over substrate layer 2915. The first metal layer 2923B may include first openings. The biosensor 3600 may further include a second dielectric layer 2925 over the metal layer 2923B and the first passivation layer 2920. The second dielectric layer 2925 may also be positioned in the first openings of metal layer 2923B.

The biosensor 3600 may further include color filter material 2927B over the second dielectric layer 2925 and in and above the first openings of metal layer 2923B, such that a top surface of color filter material 2927B may be planar with a top surface of the second dielectric layer 2925 over the metal layer 2923B. The biosensor 3600 may further include a second passivation layer 2930 over the second dielectric layer 2925 and the color filter material 2927. The biosensor 3600 may further include a first material layer 2935 and a second material layer 2937. The first material layer 2935 may have a higher refractive index than the second material layer 2937. A biological or chemical sample may be placed in spots or wells (not shown) formed in or on the second material layer 2937 for analysis, as described further herein.

Figure 36B:
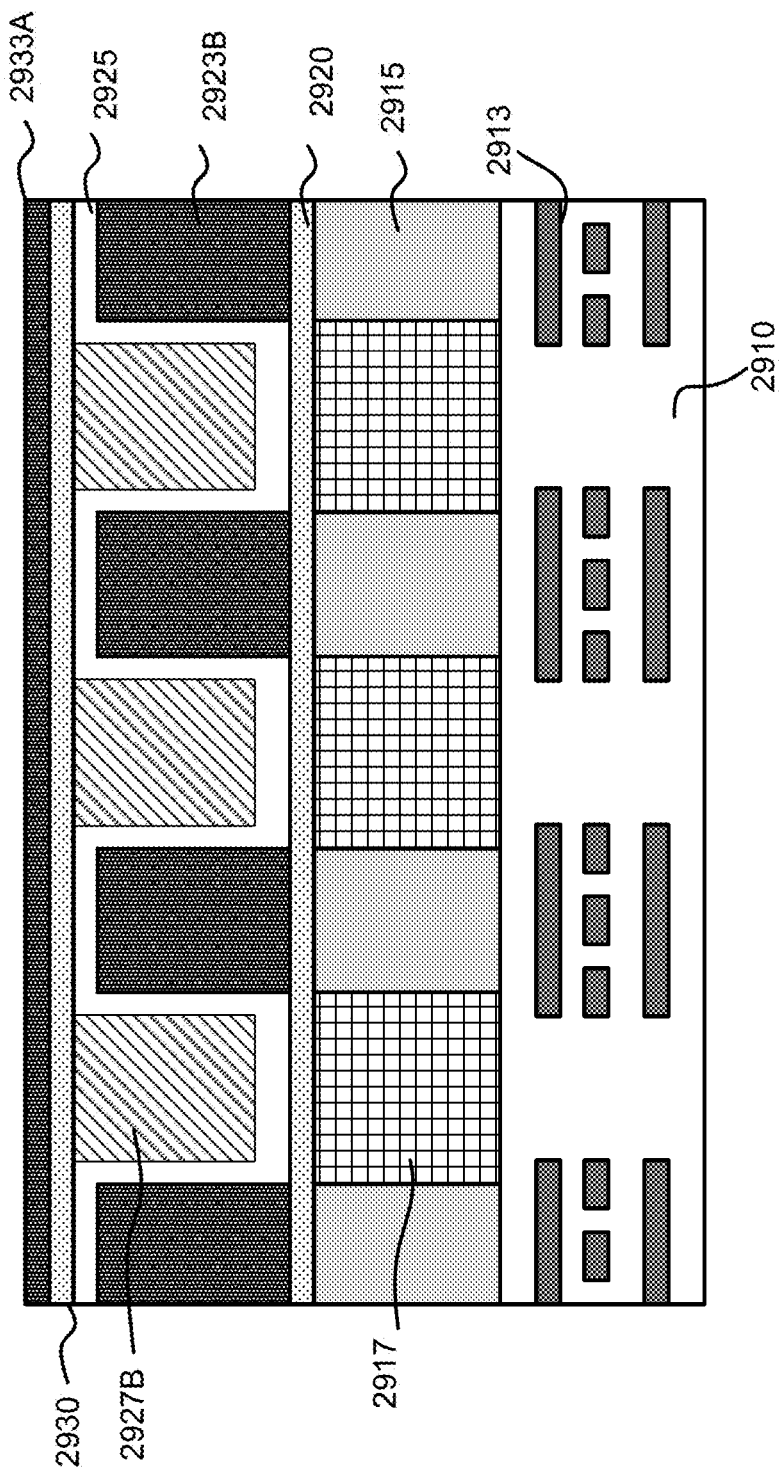
FIG. 36B is a cross-sectional view of a backside illumination CMOS image sensor with a second passivation layer and a second metal layer, according to some embodiments.

FIG. 36B illustrates an alternative embodiment than FIG. 36A. According to FIG. 36B, a second passivation layer 2930 may be deposited according to conventional semiconductor techniques over the second dielectric layer 2925 and the color filter material 2927B. The second passivation layer 2930 may include any suitable materials, such as, for example, silicon nitride, tantalum oxide, combinations thereof, and the like. In some embodiments, the second passivation layer 2930 may include one or more high-k materials. The second passivation layer 2930 may include the same or different materials than the first passivation layer 2920. In some embodiments, the second passivation layer 2930 is made of a denser material than the first passivation layer 2920. The second passivation layer 2930 may, in some embodiments, act as a protective material between a sample being analyzed and the color filter material 2927B. In some embodiments, the second passivation layer 2930 acts as an etch stop for later etching steps. The second passivation layer 2930 may be transparent.

Further according to FIG. 36B, a second metal layer 2933A may be deposited according to conventional semiconductor techniques over the second passivation layer 2930. The second metal layer 2933A may include any suitable metal material, such as, for example, tungsten, aluminum, copper, combinations thereof, and the like. The second metal layer 2933A may be made of the same or a different material than the first metal layer 2923B. The second metal layer 2933A may be opaque to incident or excitation light.

Figure 37:
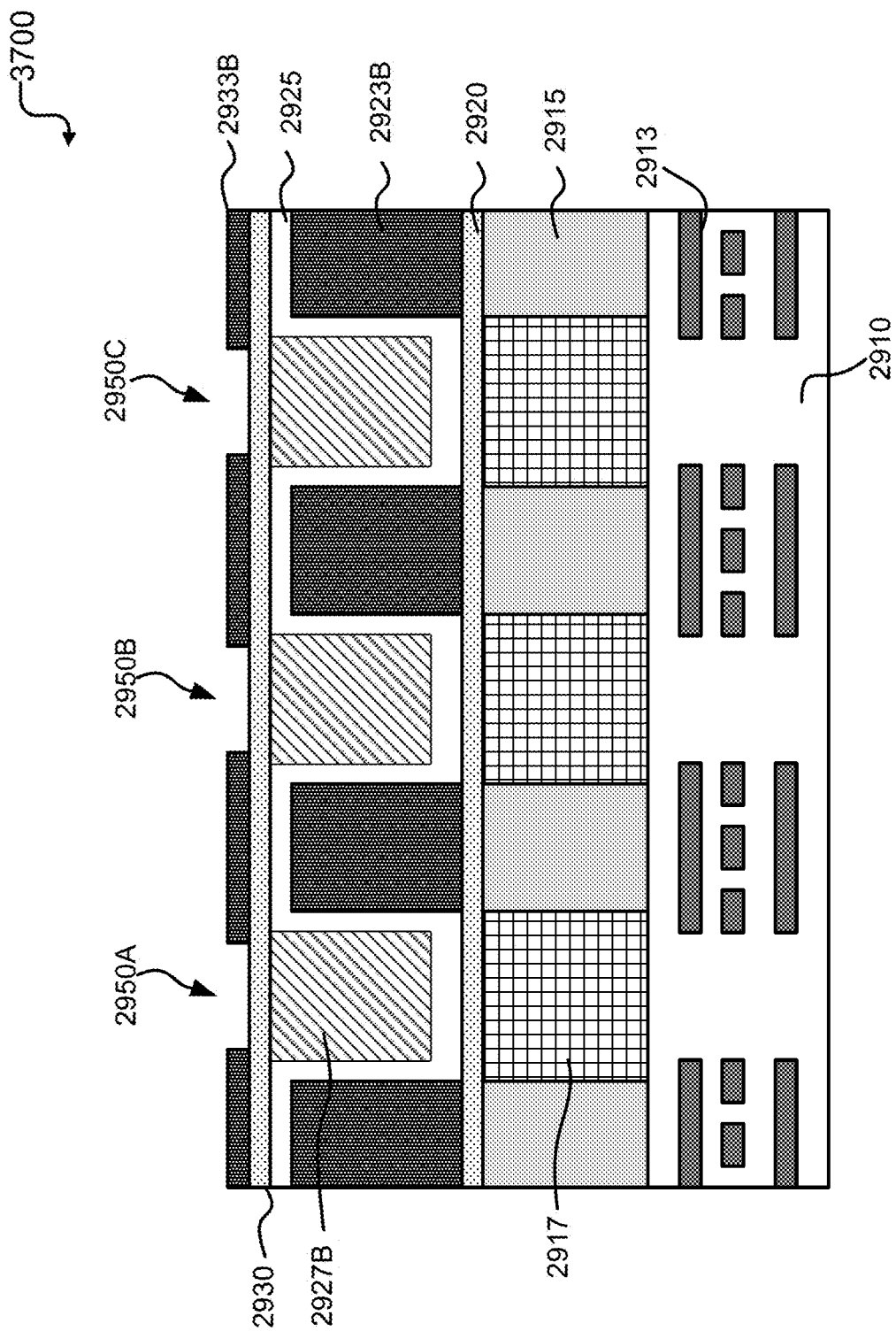
FIG. 37 is a cross-sectional view of a biosensor using a backside illumination CMOS image sensor, according to some embodiments.
Figure 38:
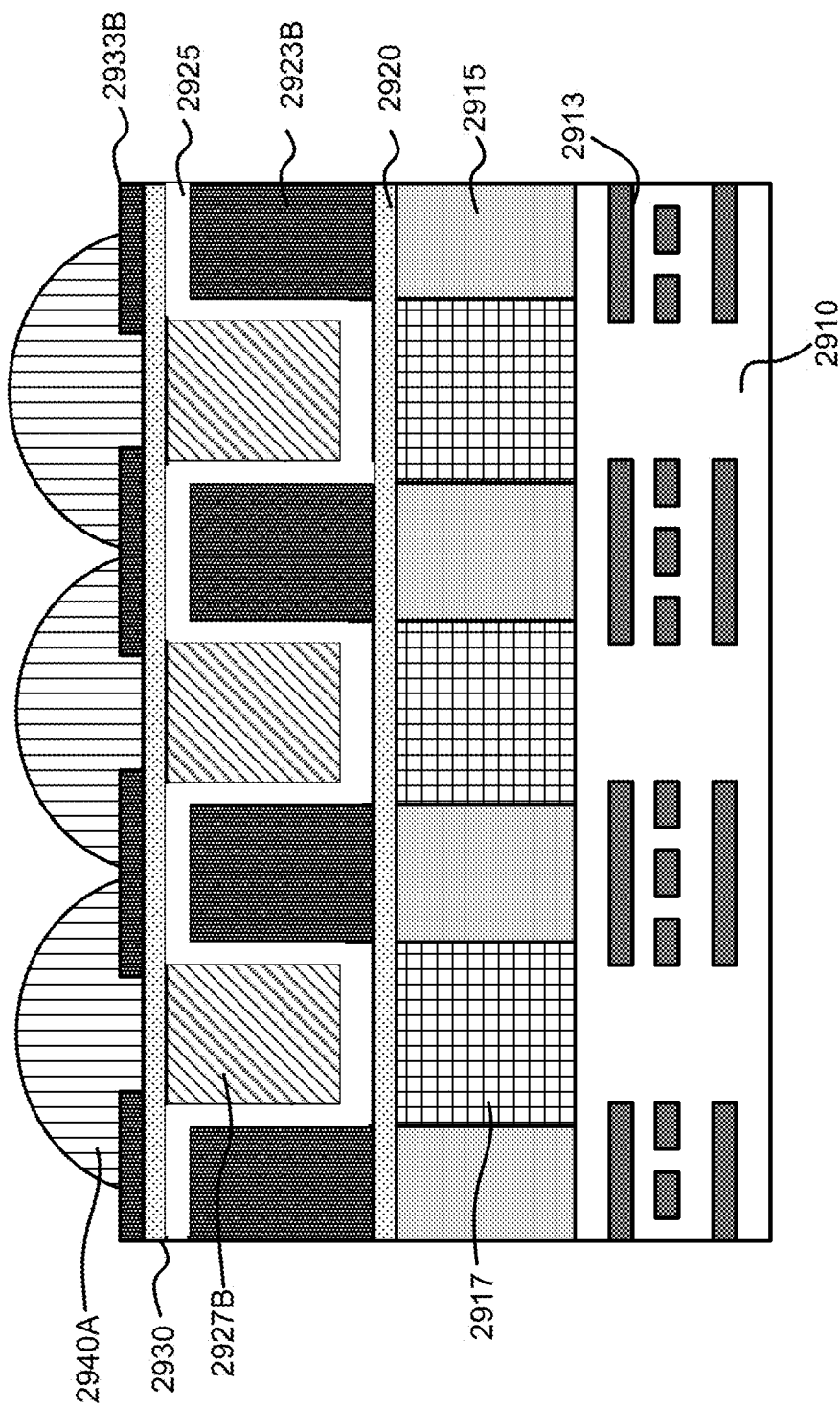
FIG. 38 is a cross-sectional view of a biosensor using a backside illumination CMOS image sensor and microlenses, according to some embodiments.

Then, according to FIG. 37, the second metal layer 2933B may be etched out of the second metal layer 2933A or patterned, creating second openings 2950A-C in the second metal layer 2933A. In some embodiments, the second openings 2950A-C may be aligned center to center with the photodiodes 2917. In some embodiments, the second openings 2950A-C may have a diameter in the range of 100 nanometer to 1 micrometer. The second openings 2950A-C may have a smaller width or diameter than the color filter material 2927B. In some embodiments, biological or chemical samples may be placed in the second openings 2950A-C, and light emitted from the samples may be used to measure their fluorescence or chemiluminescence, as described further herein. In embodiments in which the second openings 2950A-C are smaller in width or diameter than the color filter material 2927B, there may be increased blockage of incident or excitation light, resulting in less noise in detection of the fluorescence or luminescence of a sample. The width or diameter of the second openings 2950A-C may approximately correspond to the size of the biological or chemical sample being analyzed.

C. Biosensor 3700 of FIG. 37

Thus, FIG. 37 illustrates a biosensor 3700 that may be used for biological or chemical analysis according to some embodiments. The biosensor 3700 includes a backside illumination CMOS image sensor 2900. The backside illumination CMOS image sensor 2900 includes an electronic circuit layer (comprised of the first dielectric layer 2910 and the metal wiring 2913) and a photo sensing layer over the electronic circuit layer (comprised of a substrate layer 2915 and photodiodes 2917). The photodiodes 2917 may be in contact with the electronic circuit layer such that electronic signals may be transmitted from the photodiode 2917 to the electronic circuit layer, and in some embodiments, to an external device. A light receiving surface is defined by a surface of the photodiodes 2917 that is opposite to the electronic circuit layer (i.e., the surface in contact with the first passivation layer 2920).

The biosensor 3700 may further include the first passivation layer 2920 over the backside illumination CMOS image sensor 2900, and a first metal layer 2923B over the first passivation layer 2920. The first metal layer 2923B may also be positioned over substrate layer 2915. The first metal layer 2923B may include first openings. The biosensor 3700 may further include a second dielectric layer 2925 over the metal layer 2923B and the first passivation layer 2920. The second dielectric layer 2925 may also be positioned in the first openings of metal layer 2923B.

The biosensor 3700 may further include color filter material 2927B over the second dielectric layer 2925 and in and above the first openings of metal layer 2923B, such that a top surface of color filter material 2927B may be planar with a top surface of the second dielectric layer 2925 over the metal layer 2923B. The biosensor 3700 may further include a second passivation layer 2930 over the second dielectric layer 2925 and the color filter material 2927. The biosensor 3700 may further include a second metal layer 2933B having second openings 2950A-C. The second openings 2950A-C may function as spots or wells configured to receive biological or chemical samples, as described further herein.

Referring again to the embodiment of FIG. 37, various further manufacturing techniques may be implemented for further signal enhancement, as described herein with respect to FIGS. 38-41. According to FIG. 38, microlenses 2940A may be grown over the second passivation layer 2930 and the second metal layer 2933B. In some embodiments, the microlenses 2940A may be aligned center to center with the photodiodes 2917. The microlenses 2940A may include a variety of materials, such as glass, polymers, plastics, combinations thereof, and the like. The microlenses 2940A may be included in the device above each of the color filters 2927B to focus light emitted into each of the color filters 2927B.

The microlenses 2940A may be grown according to any suitable microlens fabrication process, such as those commonly used with respect to CMOS image sensors. As one example, photolithography may be performed on a photoresist or ultraviolet curable epoxy material and the material may be melted to form arrays of microlenses 2940A. As another example, small filaments of glass may be melted, and the surface tension of the molten glass may form smooth spherical surfaces. The spherically-surfaced glass may then be mounted and grinded as appropriate to form microlenses 2940A. In still another example, wafer-level optics (WLO) may be used, in which multiple lens wafers are precision aligned, bonded together, and diced to form multi-element stacks that may be used as microlenses 2940A.

Figure 39:
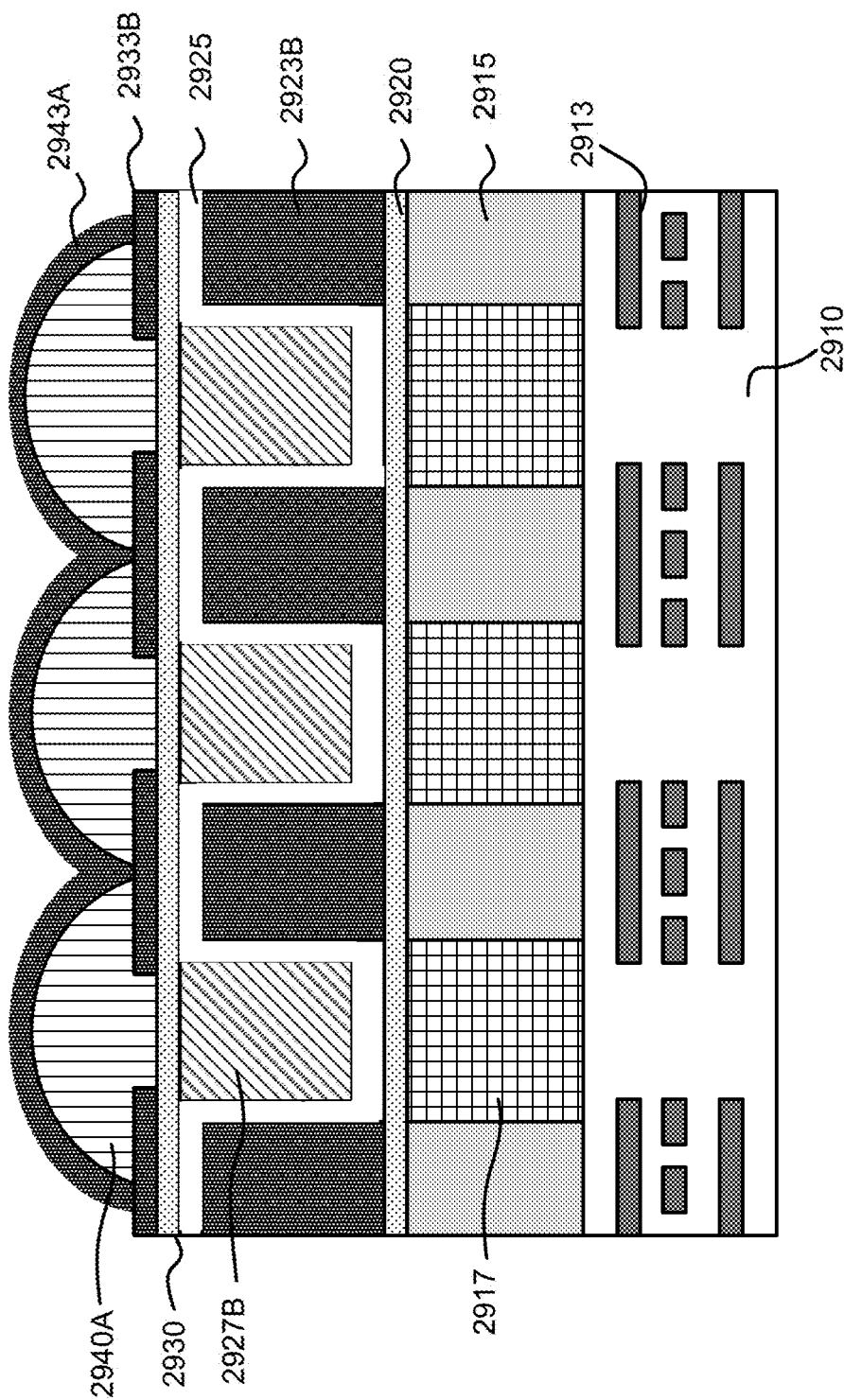
FIG. 39 is a cross-sectional view of a biosensor using a backside illumination CMOS image sensor, microlenses and a third metal layer, according to some embodiments.

According to FIG. 39, a third metal layer 2943A may be deposited according to conventional semiconductor processing techniques over the microlenses 2940A. The third metal layer 2943A may include any suitable materials, such as tungsten, aluminum, copper, combinations thereof, and the like. The third metal layer 2943A may be a relatively thin layer, e.g., thinner than the second metal layer 2923B. The third metal layer 2943A may be made of the same or different materials than the first metal layer 2923B and/or the second metal layer 2933B.

Figure 40:
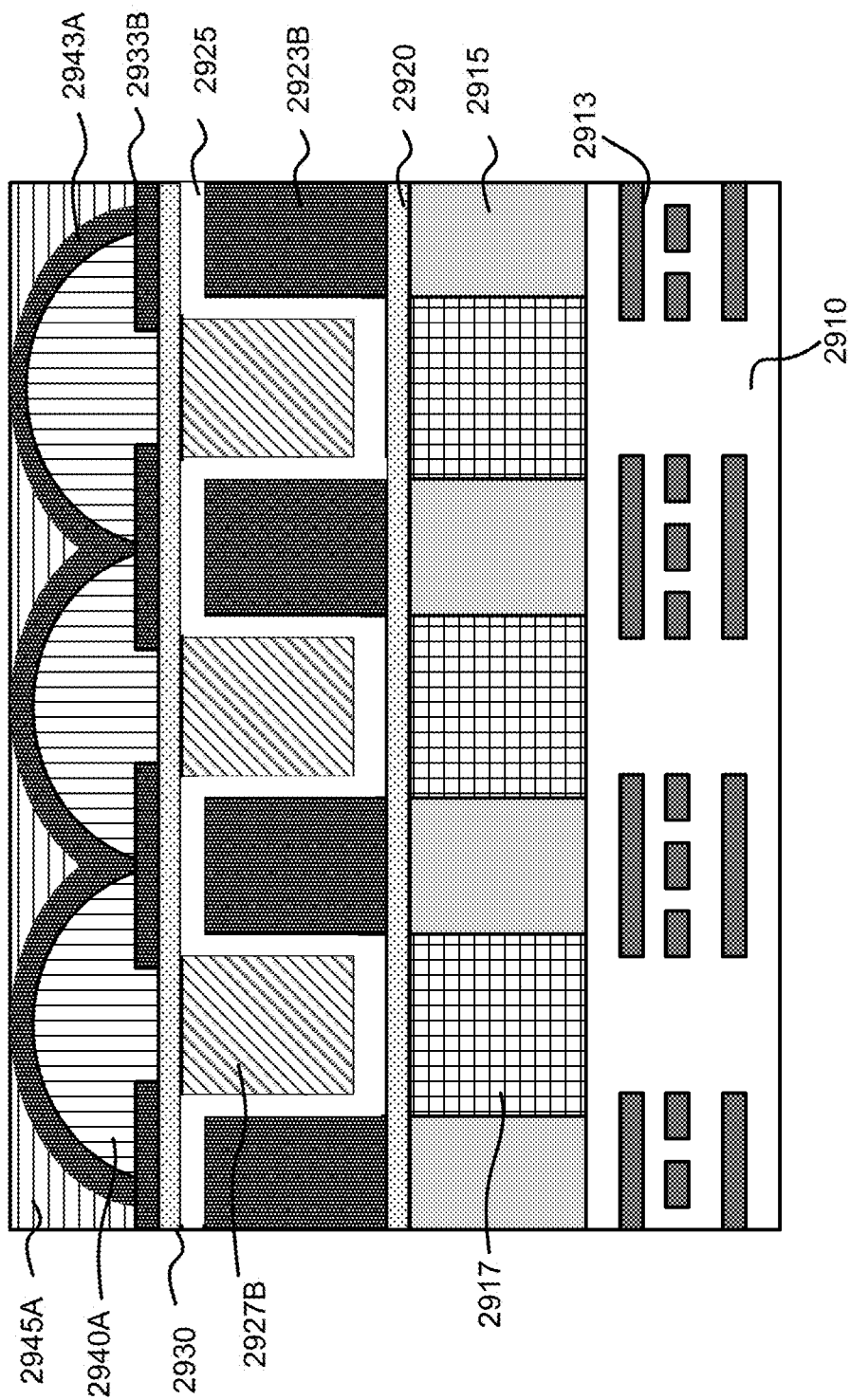
FIG. 40 is a cross-sectional view of a biosensor using a backside illumination CMOS image sensor, microlenses, a third metal layer, and a planarization layer, according to some embodiments.

According to FIG. 40, a planarization layer 2945A may be deposited over the third metal layer 2943A. The planarization layer 2945A may include any suitable materials. The planarization layer 2945A may be deposited by, for example, spin coating, or by any other suitable method. If the planarization layer 2945A exceeds a top exposed surface of the third metal layer 2943A, the planarization layer 2945A may be planarized by, for example, chemical-mechanical planarization (CMP), leaving the planarization layer 2945A in the openings between the third metal layer 2943A and creating a substantially planar upper surface.

Figure 41:
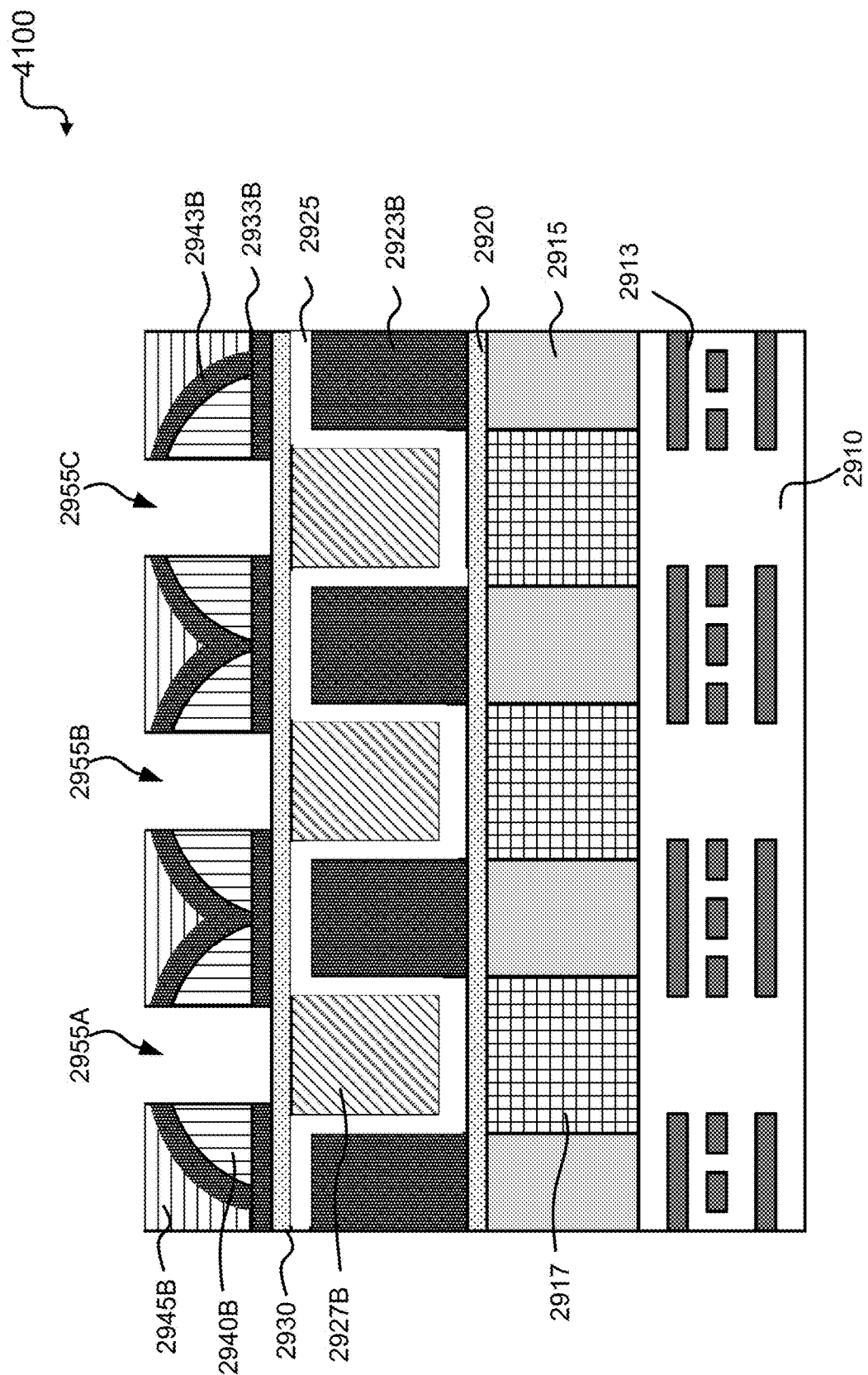
FIG. 41 is a cross-sectional view of a biosensor using a backside illumination CMOS image sensor, according to some embodiments.

According to FIG. 41, third openings 2955A-C may be etched through planarization layer 2945A (leaving planarization layer 2945B remaining), the third metal layer 2943A (leaving the third metal layer 2943B remaining), and microlenses 2940A (leaving the microlenses 2940B remaining). For example, the planarization layer 2945B may be spin coated with a photoresist (not shown) in order to etch the third openings 2955A-C. In some embodiments, the width of the third openings 2955A-C may correspond to the width of the second openings 2950A-C, such that the second metal layer 2933B does not need to be further etched. Third openings 2955A-C may be etched to the second passivation layer 2930, with the second passivation layer 2930 acting as an etch stop. In some examples, third openings 2955A-C may have a diameter between 100 nanometers and 1 micrometer, and may be aligned center to center with the color filter material 2927B and/or the photodiode 2917. In some embodiments, biological or chemical samples may be placed in the third openings 2955A-C on the second passivation layer 2930, and the fluorescence or chemiluminescence of the samples may be measured, as described further herein.

D. Biosensor 4100 of FIG. 41

Thus, FIG. 41 illustrates a biosensor 4100 that may be used for biological or chemical analysis according to some embodiments. The biosensor 4100 includes a backside illumination CMOS image sensor 2900. The backside illumination CMOS image sensor 2900 includes an electronic circuit layer (comprised of the first dielectric layer 2910 and the metal wiring 2913) and a photo sensing layer over the electronic circuit layer (comprised of a substrate layer 2915 and photodiodes 2917). The photodiodes 2917 may be in contact with the electronic circuit layer such that electronic signals may be transmitted from the photodiode 2917 to the electronic circuit layer, and in some embodiments, to an external device. A light receiving surface is defined by a surface of the photodiodes 2917 that is opposite to the electronic circuit layer (i.e., the surface in contact with the first passivation layer 2920).

The biosensor 4100 may further include the first passivation layer 2920 over the backside illumination CMOS image sensor 2900, and a first metal layer 2923B over the first passivation layer 2920. The first metal layer 2923B may also be positioned over substrate layer 2915. The first metal layer 2923B may include first openings. The biosensor 4100 may further include a second dielectric layer 2925 over the metal layer 2923B and the first passivation layer 2920. The second dielectric layer 2925 may also be positioned in the first openings of metal layer 2923B.

The biosensor 4100 may further include color filter material 2927B over the second dielectric layer 2925 and in and above the first openings of metal layer 2923B, such that a top surface of color filter material 2927B may be planar with a top surface of the second dielectric layer 2925 over the metal layer 2923B. The biosensor 4100 may further include a second passivation layer 2930 over the second dielectric layer 2925 and the color filter material 2927. The biosensor 4100 may further include a second metal layer 2933B over the second passivation layer 2930 having second openings 2950A-C.

The biosensor 4100 may further include microlenses 2940B over the second metal layer 2933B, a third metal layer 2943B over the microlenses 2940B, and a planarization layer 2945 over the third metal layer 2943B. The third metal layer 2943B may serve a number of different purposes in the biosensor 4100. For example, the third metal layer 2943B may help to block incident light from entering the color filter material 2927B. In addition, because the third metal layer 2943B is curved, any light emitted from a biological or chemical sample may be passed through the microlenses 2940B, reflected off of the third metal layer 2943B, and directed back toward the color filter material 2927B and thus, the light receiving surface of the photodiode 2917. In other words, the amount of emitted light that may be measured by the photodiode 2917 may be maximized.

The planarization layer 2945 may form a planar surface over the third metal layer 2943B. The microlenses 2940B, the third metal layer 2943B, and the planarization layer 2945 may have third openings 2955A-C formed therein that may overlap with the second openings 2950A-C in some embodiments. For example, the third openings 2955A-C may have the same width as the second openings 2950A-C. However, it is contemplated that in some embodiments, the third openings 2955A-C may have a different width than the second openings 2950A-C. Together, the second openings 2950A-C and the third openings 2955A-C may function as spots or wells configured to receive biological or chemical samples, as described further herein. Because the third openings 2955A-C of FIG. 41 are deeper than the second openings 2950A-C of FIG. 37, excitation light may generally be directed from a source positioned directly above the third openings 2955A-C in biosensor 4100. Biosensor 3700 may be able to tolerate more angular misalignment of excitation light because second openings 2950A-C are not as deep as third openings 2955A-C.

Nucleic Acid Sequencing Applications

As described above with respect to FIGS. 30, 36A, 37, and 41, biological or chemical samples may be placed on each of the described biosensors above color filter material 2927B and the photodiodes 2917. The biological or chemical sample may include any of a number of components. For example, the sample may contain nucleic acid macromolecules (e.g., DNA, RNA, etc.), proteins, and the like. The sample may be analyzed to determine a gene sequence, DNA-DNA hybridization, single nucleotide polymorphisms, protein interactions, peptide interactions, antigen-antibody interactions, glucose monitoring, cholesterol monitoring, and the like.

As discussed above, in some embodiments the biomolecule is a nucleic acid, such as DNA. Without limitation, the DNA biomolecule may be a DNA nanoball (single stranded concatemer) hybridized to labeled probes (e.g., in DNB sequencing by ligation or cPAL methods) or to complementary growing strands (e.g., in DNB sequencing by synthesis methods) or both; or to a single DNA molecule (e.g., in single molecule sequencing); or to a clonal population of DNA molecules, such as is created in bridge PCR based sequencing. Thus, reference to "a biomolecule", "a DNA macromolecule" or "a nucleic acid macromolecule" may encompass more than one molecule (e.g., a DNB associated with multiple growing complementary strands or a DNA cluster comprising clonal population of hundreds or thousands of DNA molecules). See, e.g., U.S. Pat. No. 8,133,719; U.S. Pat. App. Pub. No. 2013/0116153, U.S. Pat. App. Pub. No. 2016/0237488; U.S. Pat. App. Pub. No. 2012/0224050; U.S. Pat. Nos. 8,133,719; 7,910,354; 9,222,132; 6,210,891; 6,828,100, 6,833,246; and 6,911,345, herein incorporated by reference in their entireties.

In some embodiments, color filter material 2927B may be sized and functionalized to receive (in spots or wells above color filter material 2927B) biological or chemical samples and to absorb light emitted from the biological or chemical sample in some examples. For example, if color filter material 2927B is red and the emitted light from the biological or chemical sample is green, color filter material 2927B may absorb the green emitted light. In some embodiments, color filter material 2927B may be sized and functionalized to receive (in spots or wells above color filter material 2927B) biological or chemical samples and to pass light emitted from the biological or chemical sample through the color filter material 2927B and onto the light receiving surface of the photodiode 2917. For example, if color filter material 2927B is blue and the emitted light from the biological or chemical sample is blue, color filter material 2927B may pass the blue emitted light through to the light receiving surface of the corresponding photodiode 2917. In other words, in some embodiments, emitted light may be absorbed by color filter material 2927B. In some embodiments, emitted light may be transmitted through the color filter material 2927B and onto the photodiode 2917.

To achieve high density and assist in alignment between the nucleic acid macromolecules and the photodiodes 2917 of the biosensor, the surface of the biosensor may be constructed such that there are active spots or wells (e.g., openings 2950A-C, openings 2955A-C, etc.) that are sized and chemically functionalized to receive a nucleic acid macromolecule, surrounded by areas of the surface to which the nucleic acid macromolecules may not bind. The nucleic acid macromolecules may be secured to the active surface aligned with the photodiode 2917 using any suitable surface chemistry. This may include non-covalent interaction (for example, to an area bearing positive charge) or interaction with a capture probe or oligonucleotide attached to the surface, bearing a sequence that is complementary to a sequence contained in the nucleic acid macromolecule. See, for example, U.S. Pat. No. 8,445,194, which is herein incorporated by reference in its entirety.

EXAMPLE

This example demonstrates that BSI CIS sensors may be used to detect weak signals from surface attached photon emitting molecules. We constructed a biosensor as described in FIG. 37, but without a color filter layer (i.e., lacking elements 2920, 2923B, 2925, and 2927B). In addition, surface 2933B was rendered hydrophobic, and the bottom surfaces of openings 2950A/B/C were rendered hydrophilic (such that DNBs were distributed toward the hydrophilic surfaces and away from the hydrophobic surfaces).

A dilute solution of DNA nanoballs (DNBs) was applied the biosensor array allowing individual DNBs to settle on the spots of the array. For purposes of this experiment all of the DNBs have the same sequence, in contrast to sequencing methods in which essentially all DNBs on an array will have different sequences, and in which the sequence of a DNB are any specific spot/position will not be known prior to sequence determination.

Two primers were hybridized to the DNA templates (see FIG. 43A, top). The "left" primer has a blocked (nonextendible) 3' terminus and is labeled at the 5' terminus with a fluorescent dye. The fluorescent dye was used to establish the position of the DNBs on the array (not shown). The "right" primer acts as an extendible primer for sequencing by synthesis. Sequencing reagents and detection reagents 4 were added (DNA polymerase, streptavidin, biotinylated luciferase 3, ATP and luciferin) along with dATP tagged with biotin via a cleavable linker. In this system the streptavidin 2 associates with the biotin conjugated to the incorporated nucleotide and also associates with biotinylated luciferase, as shown in FIG. 43A. (Biotin 1 symbolized by diamond.) The ATP acts as a substrate for the generation of light by the luciferase-mediated conversion of luciferin to oxyluciferin. The light is received by the photodiodes, generating a signal. The signal is correlated with incorporation of dATP, indicating the present of thymine at the corresponding position of the template sequence. FIG. 43A shows signal from DNBs at numerous spots on the array.

THPP was then used to cleave the cleavable linker, releasing the biotin/streptavidin/luciferase complex, and the array was washed to remove all soluble reagents. FIG. 43B shows that following the wash step signal from the array is absent or significantly reduced.

A second incorporation round was carried out using dTTP-digoxin and DNA polymerase as shown in FIG. 43C. The incorporation of dTTP is detected using a biotinylated anti-digoxin antibody, streptavidin, biotinylated luciferase, ATP and luciferin. The use of biotinylated anti-digoxin antibody amplifies the signal generated by each incorporation event. FIG. 43C is an image showing that chemiluminescent light was generated at numerous spots on the array. This example demonstrates, using two different dNTPs and two different detection systems, that the BSI CIS sensors of the invention may be used to detect weak signals from surface attached photon emitting molecules such as DNBs.

VII. Alternative Differential Surfaces for a Biosensor

FIGS. 44-47 describe various stages of manufacture of a biosensor having differential surfaces according to embodiments of the invention. Other embodiments of manufacture and configuration will be evident from this description to those of skill in the art. It is therefore intended that the following description be descriptive but not limiting.

Figure 44:
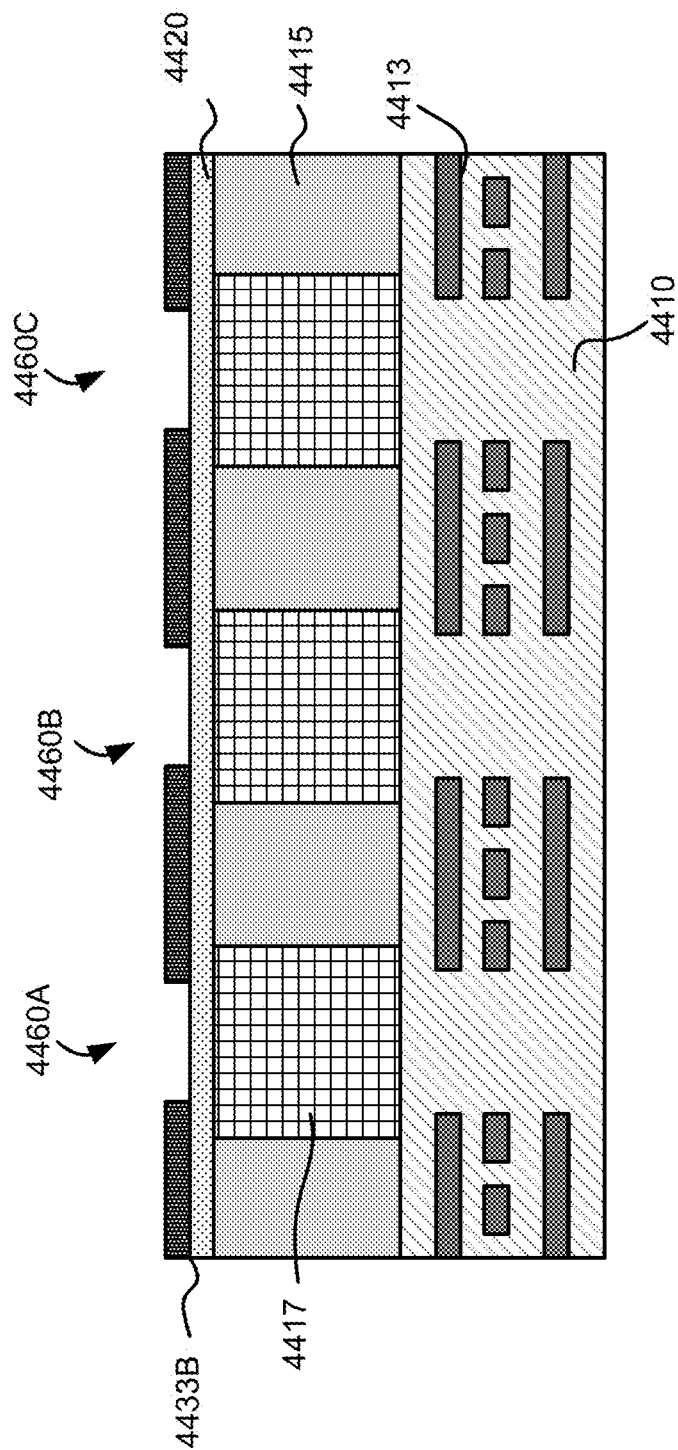
FIG. 44 is a cross-sectional view of a backside illumination CMOS image sensor with the mask removed, according to some embodiments.

FIG. 44 is a cross-sectional view of a backside illumination (BSI) CMOS image sensor with the mask removed, according to some embodiments. According to FIG. 44, voids 4460A-C may be created by the metal layer or metal oxide layer 4433B on the sides, and the passivation layer 4420 on the bottom. The device structure in FIG. 44 is similar to device 2600 in FIG. 26, but with a substrate including sensors 4417 and a metal wiring 4413 in a dielectric layer 4410. The device structure in FIG. 44 is also similar to top portion of device 200 in FIG. 2. The device structure in FIG. 44 is also similar to top portion of device 3700 in FIG. 37, with the filter layer removed. The method described here is also applicable to similar device structures. The voids 4460A-C may form a spot or well into which biological or chemical samples may be placed, as described further herein.

In some embodiments, a first covering layer and a second covering layer, different from the first covering layer, may be selectively applied based on the differential surfaces of the metal layer or metal oxide layer 4433B and the passivation layer 4420, respectively. The first and second covering layers have different properties, resulting in an array of spots or wells comprising a bottom surface comprising the second covering layer, separated by areas (e.g., 4433B) comprising the first covering layer. In some embodiments macromolecules of interest preferentially associate with the second covering layer compared with the first covering layer.

Figure 45:
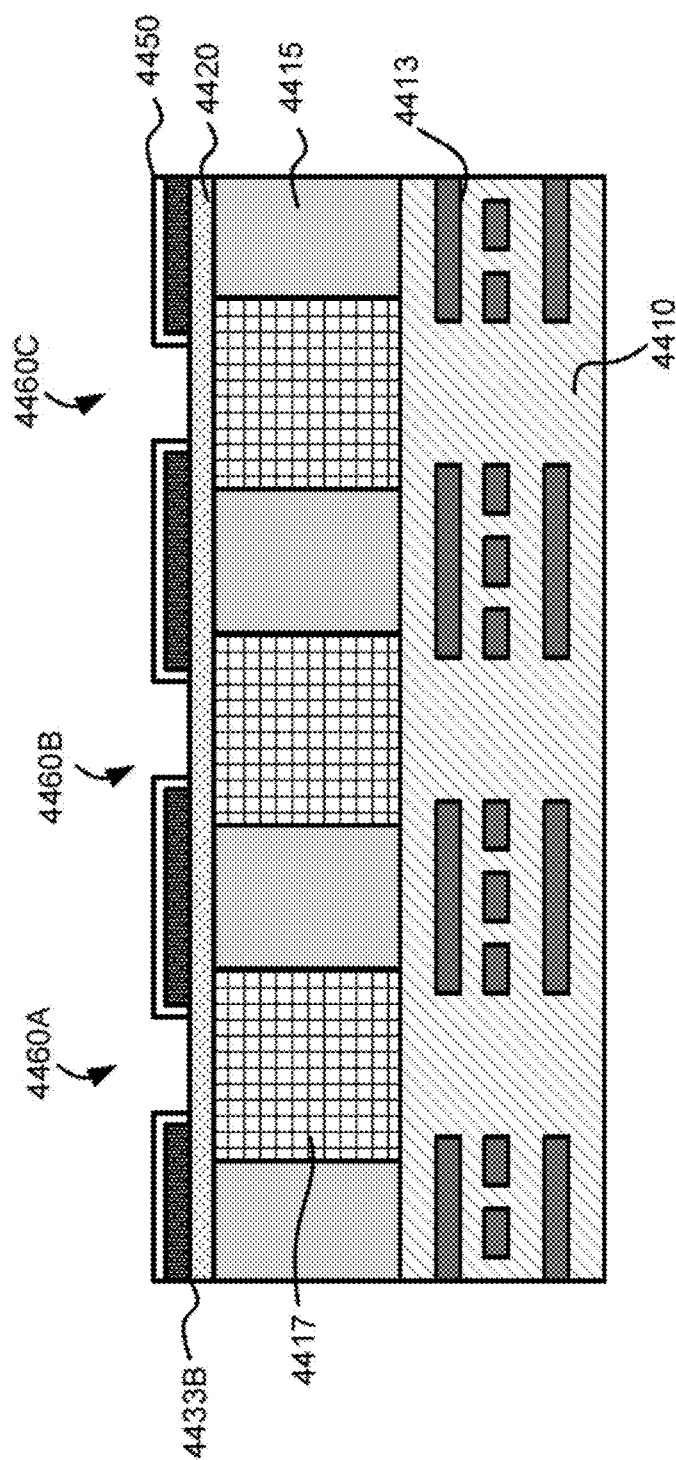
FIG. 45 is a cross-sectional view of a backside illumination CMOS image sensor with a first coating selectively applied due to differential surfaces, according to some embodiments.

FIG. 45 is a cross-sectional view of a backside illumination CMOS image sensor with a first coating selectively applied due to differential surfaces, according to some embodiments. As illustrated in FIG. 45, the first covering layer 4450 may be selectively applied to the metal layer or metal oxide layer 4433B based on its surface properties. For example, the first covering layer 4450 may be of such a material that it may bond to and/or be attracted to the metal layer or metal oxide layer 4433B. In some embodiments the first covering layer does not bind or adhere to, or is repelled by, the passivation layer 4420, resulting in the structure shown in FIG. 45. The first covering layer 4450 may be applied to the metal layer or metal oxide layer 4433B according to any method or technique (e.g., chemical vapor deposition, dipping, spin coating, and/or the like). For example, the metal layer or metal oxide layer 4433B may be coated or treated with a first material to form the first covering layer 4450. The first covering layer 4450 may be deposited according to conventional semiconductor processing techniques. It will be recognized that term "covering layer" is not intended to ascribe any particular structure or dimensions.

The first covering layer 4450 may include any suitable material that adheres or binds the metal or metal oxide material 4433B. In one approach the first covering layer 4455 is produced by application of a phosphate compound that binds metal or metal oxide, including without limitation, inorganic phosphate, phosphonic acid, organic phosphate compounds such as hexamethylphosphoramide, hexamethyl tetraphosphate, combinations thereof, and the like.

In some embodiments, the first covering layer 4450 may include a material that repels biological or chemical analytes of interest. For example, the first covering layer 4450 may include a material that has a negative charge, thus repelling negatively charged biological or chemical samples. In some embodiments, the first covering layer 4450 may be hydrophobic. Those of ordinary skill in the art will recognize that combinations (e.g., pairwise combinations) of metals and the first covering layer can be selected and optimized for particular purposes.

Figure 46:
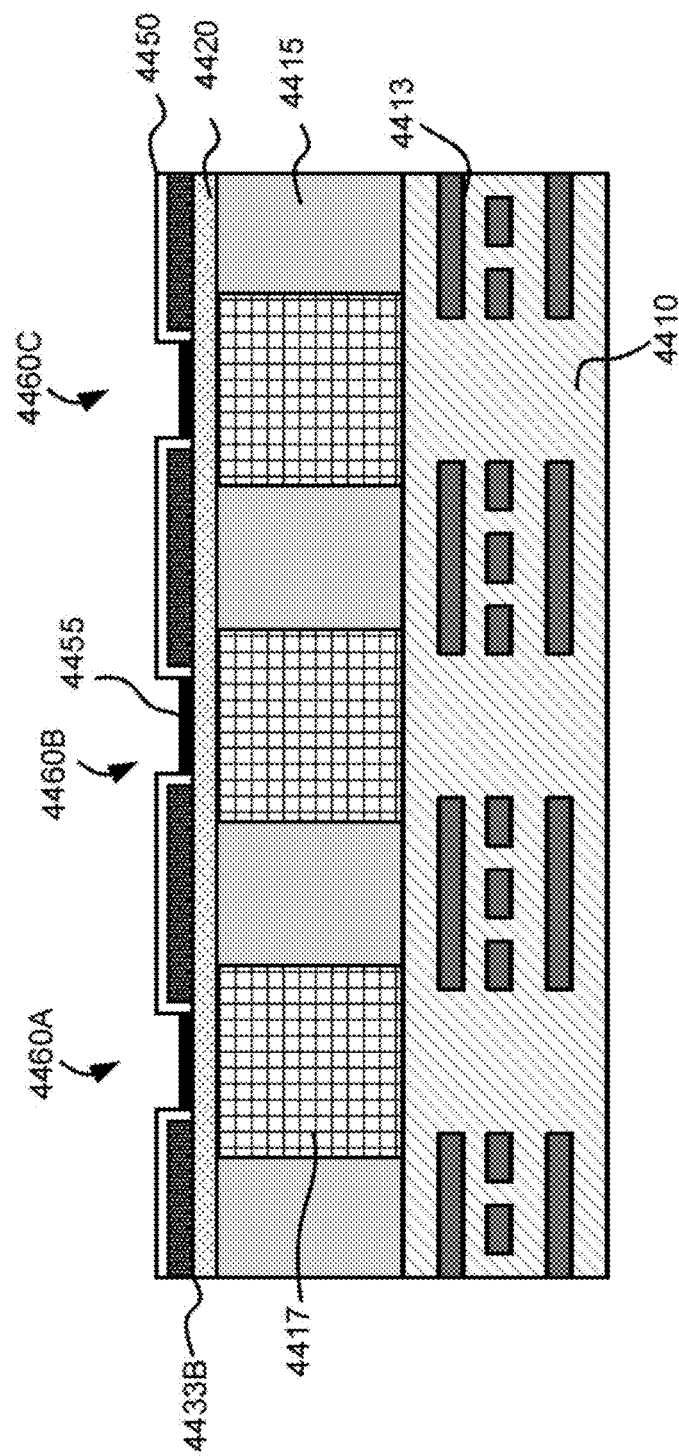
FIG. 46 is a cross-sectional view of a backside illumination CMOS image sensor with a second coating selectively applied due to differential surfaces, according to some embodiments.

FIG. 46 is a cross-sectional view of a backside illumination CMOS image sensor with a second coating selectively applied due to differential surfaces, according to some embodiments. As illustrated in FIG. 46, the second covering layer 4455 may be selectively applied to the passivation layer 4420 based on the surface properties of the passivation layer. For example, the second covering layer 4455 may be of such a material that it may bond to and/or be attracted to the passivation layer 4420, but does not bond to or adhere to the first covering layer 4450 which covers metal or metal oxide 4433B. The second covering layer 4455 may be applied by coating or treating the exposed portions of the passivation layer 4420 with a second material. In one approach, both the exposed passivation layer 4420 and metal or metal oxide 4433B regions covered by the first covering layer 4450 are exposed to the second material, which adheres only on the passivation layer. The second covering layer 4455 may be deposited according to conventional semiconductor processing techniques.

In one approach the second covering layer 4455 is produced by application of silane or a silane compound, including without limitation, aminopropyltrimethoxysilane, 3-aminopropyl-methyldiethoxysilane, 3-aminopropyltriethoxysilane, etc. In some embodiments, the second covering layer 4455 may include a material that attracts biological or chemical samples. For example, the second covering layer 4455 may include a material that has a positive charge, thus attracting negatively charged biological or chemical samples. In some embodiments, the second covering layer 4455 may be hydrophilic. Those of ordinary skill in the art will recognize that combinations (e.g., pairwise combinations) of the first covering layer and the passivation layer 4420 (i.e., the surface of the passivation layer) can be selected and optimized for particular purposes.

It will be recognized that the term "covering layer" is not intended to limit the first and second covering layers to any particular method of application or structure. As noted, different properties of the first and the second covering layers may be selected to differentially retain target macromolecule(s), e.g., DNA macromolecules. It will also be recognized that the first and/or second covering layers may be functionalized such that the functionalized surface has a property that results in differential retention of target macromolecule(s). For illustration, after application of the first and second covering layers a DNA binding molecule (e.g., oligonucleotide) with affinity to the second covering layers, but not to the first covering layers, may be applied to cover second covering layer 4455. In some embodiments, the second covering layer 4455 is a functionalized surface on which a single nucleic acid molecule is amplified.

It will be recognized that the term "first covering layer" may refer to the material applied to the surface as well as the material retained on the surface (e.g., the latter may differ from the former by evaporation of a solvent; by a reaction with the surface material, and the like).

Thus, a structure may be created in which a first covering layer 4450B is present on the metal layer or metal oxide layer 4433B, and a second covering layer 4455 is present in the voids 4460A-C. The voids 4460A-C may be formed by the first covering layer 4450B and the metal layer or metal oxide layer 4433B on the sides, and the passivation layer 4420 on the bottom. The voids 4460A-C may form a spot or well into which biological or chemical samples may be placed, as described further herein.

Figure 47:
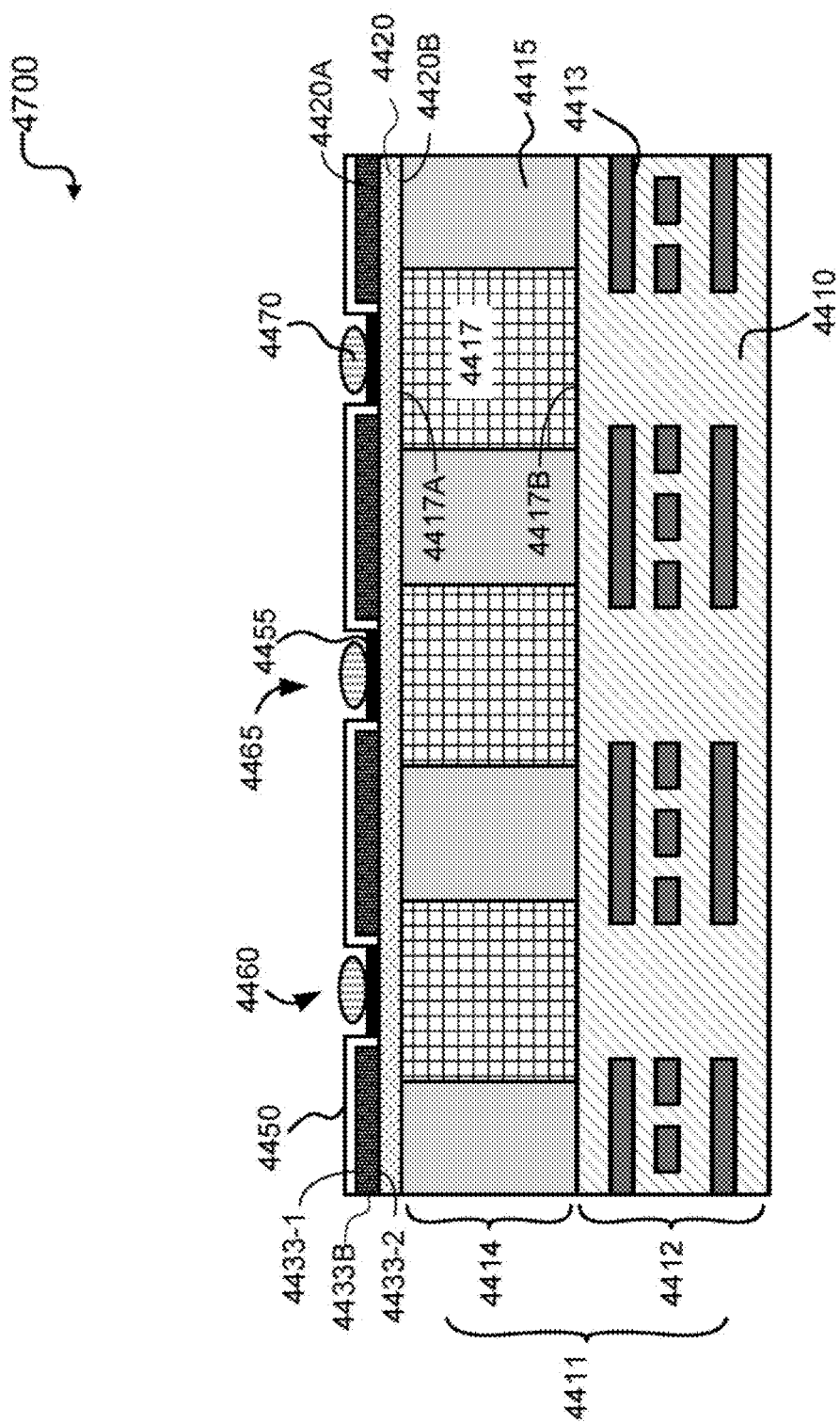
FIG. 47 is a cross-sectional view of a biosensor using a backside illumination CMOS image sensor with macromolecules, according to some embodiments.

FIG. 47 is a cross-sectional view of a biosensor using a backside illumination CMOS image sensor with macromolecules, according to some embodiments. According to FIG. 47, biological or chemical samples 4470 may be introduced in the voids atop the second covering layer 4455. The invention is not limited to any particular method of introduction. In some embodiments, the biological or chemical samples 4470 may be attracted to or bind to the second covering layer 4455, while being repelled by the first covering layer 4450. This may prevent the biological or chemical samples 4470 from sticking to the first covering layer 4450B on the metal layer or metal oxide layer 4433B where they cannot be sensed by the photodiodes 4417.

As illustrated in FIGS. 44, 46, and 47, in some embodiments, the metal layer or metal oxide layer 4433B and the top surfaces of photodiodes 4417 or the passivation layer 4420 form a plurality of wells or voids 4460A-C, wherein wall(s) of each well are formed from the metal layer, and the bottoms of each well are formed from the photodiode 4417 surface or from the overlying passivation layer 4420. In some embodiments, the wall(s) may have a height, h, that extends from the well bottom to the level corresponding the top of covering layer 4450B where the bottom and walls define the void(s) 4460A-C. In some embodiments, the surface area of the well bottom is less that the surface area of the underlying photodiode. In some embodiments, the volume of the void 4460A-C is in the range of $1 \times 10^{-24}$ m3-$1 \times 10^{-21}$ m2; and/or the height of the walls is in the range of 1 nm-500 nm; and/or the area of the bottom is in the range of $1 \times 10^{-15}$ m2-$1 \times 10^{-14}$ m2. In some embodiments, the ratio of the width or diameter of the well to the height of the walls is in the range of 1-200.

In some embodiments, as illustrated in FIG. 47, a biosensor 4700 can include a backside illumination complementary metal-oxide-semiconductor (CMOS) image sensor 4411. Backside illumination CMOS image sensor 4411 can include an electronic circuit layer 4412 and a photo sensing layer 4414 over the electronic circuit layer. Electronic circuit layer 4412 can be comprised of a dielectric layer 4410 and metal wiring 4413. Photo sensing layer 4414 can include a substrate layer 4415 and a plurality of photodiodes 4417 having a first top surface 4417A and a first bottom surface 4417B. The first bottom surface 4417B can be in contact with the electronic circuit layer 4413 (connections not explicitly shown), and the first top surface 4417A includes a light receiving surface. Biosensor 4700 can also have a metal or metal oxide layer 4433B over the photo sensing layer 4414, and the metal or metal oxide layer 4433B has a second top surface 4433-1 and a second bottom surface 4433-2. The metal or metal oxide layer 4433B defines a plurality of voids 4460, and each void of the plurality of voids 4460 can be aligned with at least one photodiode of the plurality of photodiodes 4417. The second top surface 4433-1 can be coated or treated with a first material 4450 to form a first covering layer. Biosensor 4700 can also have a passivation layer 4420 over the plurality of photodiodes 4417, and the passivation layer has a third top surface 4420A and a third bottom surface 4420B. The metal or metal oxide layer 4433B and the third top surface 4420A of the passivation layer 4420 form a plurality of wells 4465. The walls of each well are formed from the metal or metal oxide layer 4433B, and the bottom of each well is formed from the third top surface 4420A of the passivation layer 4420. The bottom of each well can be coated or treated with a second material 4455 to form a second covering layer. The first material 4450 is different than the second material 4455.

In some embodiments of biosensor 4700, the first material can include at least one of phosphate or phosphonic acid. The second material can include silane. In some embodiments, the plurality of wells are functionalized to receive macromolecules. In some embodiments, the macromolecules are less likely to bind to the first material than to the second material. In some embodiments, the second material is configured to bind the macromolecules, and the first material is configured not to bind to the macromolecules. In some embodiments, the second material can include a ligand that binds the macromolecules. Without limitation, the macromolecule can be a nucleic acid, protein (e.g., antigen), or antibody, and the ligand can be an oligonucleotide, DNA binding protein, antigen, or antibody. The macromolecules can be antibodies that bind a DNA macromolecule. In some embodiments, the first material is hydrophobic, and the second material is hydrophilic. At least one well can be occupied by a macromolecule analyte. The macromolecule analyte can be a nucleic acid or antibody.

The biological or chemical samples may include any of a number of components. For example, a sample may contain nucleic acid macromolecules (e.g., DNA, RNA, etc.), proteins, and the like. The sample may be analyzed to determine a gene sequence, DNA-DNA hybridization, single nucleotide polymorphisms, protein interactions, peptide interactions, antigen-antibody interactions, glucose monitoring, cholesterol monitoring, and the like.

Although the processes described herein are described with respect to a certain number of steps being performed in a certain order, it is contemplated that additional steps may be included that are not explicitly shown and/or described. Further, it is contemplated that fewer steps than those shown and described may be included without departing from the scope of the described embodiments (i.e., one or some of the described steps may be optional). In addition, it is contemplated that the steps described herein may be performed in a different order than that described.

In the foregoing description, aspects of the application are described with reference to specific embodiments thereof, but those skilled in the art will recognize that the invention is not limited thereto. Thus, while illustrative embodiments of the application have been described in detail herein, it is to be understood that the inventive concepts may be otherwise variously embodied and employed, and that the appended claims are intended to be construed to include such variations, except as limited by the prior art. Various features and aspects of the above-described invention may be used individually or jointly. Further, embodiments can be utilized in any number of environments and applications beyond those described herein without departing from the broader spirit and scope of the specification. The specification and drawings are, accordingly, to be regarded as illustrative rather than restrictive. For the purposes of illustration, methods were described in a particular order. It should be appreciated that in alternate embodiments, the methods may be performed in a different order than that described.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

What is claimed is:

1. A method for forming sequencing flow cells, comprising:
   providing a semiconductor wafer having a front side and a back side, the front side covered with a dielectric layer;
   forming a patterned layer on the dielectric layer on the front side of the semiconductor wafer, the patterned layer having differential surface regions that include first surface regions and second surface regions;
   forming a plurality of through holes through the back side of the semiconductor wafer;
   attaching a cover wafer to the front side of the semiconductor wafer to form a composite wafer structure that includes a plurality of sequencing flow cells, wherein each sequencing flow cell includes:
     a flow channel between the patterned layer and the cover wafer;
     one or more first surface regions in the patterned layer;
     one or more second surface regions in the patterned layer; and
     an inlet and an outlet coupled to the flow channel, the inlet and the outlet being formed by through holes through the semiconductor substrate; and
   singulating the composite wafer structure to form a plurality of dies, each die including a sequencing flow cell.

2. The method of claim 1, wherein the first surface regions are hydrophilic surfaces and the second surface regions are hydrophobic surfaces.

3. The method of claim 1, wherein the first surface regions are hydrophobic surfaces and the second surface regions are hydrophilic surfaces.

4. The method of claim 1, wherein the semiconductor wafer further comprises a CMOS layer underlying the dielectric layer.

5. The method of claim 1, wherein forming a patterned layer comprises:
   forming a metal oxide layer overlying the dielectric layer on the semiconductor wafer; and
   patterning the metal oxide layer into a plurality of metal oxide regions,
   wherein the metal oxide regions are configured to receive nucleic acid macromolecules.

6. The method of claim 1, wherein forming a patterned layer comprises:
forming a metal oxide layer;
forming a silicon oxide layer overlying the metal oxide layer; and
patterning the silicon oxide layer,
wherein regions of the metal oxide layer not covered by the silicon oxide layer are configured to receive a nucleic acid macromolecule.

7. The method of claim 1, further comprising forming a support structure on the semiconductor wafer before attaching the cover wafer to the semiconductor wafer.

8. The method of claim 7, further comprising bonding the cover wafer to the support structure.

9. The method of claim 1, wherein the cover wafer comprises a glass wafer.

10. The method of claim 1, further comprising functionalizing the sequencing flow cell, wherein functionalizing the sequencing flow cell comprises exposing the flow channel to materials supplied through the inlet and outlet.

11. The method of claim 1, wherein singulating the composite wafer structure comprises separating the composite wafer structure into individual dies using a wafer cutting process.

12. The method of claim 2, wherein forming a patterned layer comprises:
forming a metal oxide layer overlying the dielectric layer on the semiconductor wafer; and
patterning the metal oxide layer into a plurality of metal oxide regions,
wherein the metal oxide regions are configured to receive nucleic acid macromolecules.

13. The method of claim 3, wherein forming a patterned layer comprises:
forming a metal oxide layer overlying the dielectric layer on the semiconductor wafer; and
patterning the metal oxide layer into a plurality of metal oxide regions,
wherein the metal oxide regions are configured to receive nucleic acid macromolecules.

14. A method for forming sequencing flow cells, comprising:
providing a semiconductor wafer covered with a dielectric layer;
forming a patterned layer on the dielectric layer, the patterned layer having metal oxide regions and oxide regions;
forming a plurality of through holes through the semiconductor wafer;
attaching a glass wafer to the semiconductor wafer to form a composite wafer structure that includes a plurality of sequencing flow cells, wherein each sequencing flow cell includes:
a glass layer;
multiple metal oxide regions and oxide regions; and
a flow channel between the glass layer and the multiple metal oxide regions and oxide regions,
wherein the through holes in the semiconductor wafer are configured as inlets and outlets of the sequencing flow cell; and
singulating the composite wafer structure to form a plurality of dies, each die including a sequencing flow cell.

15. The method of claim 14, wherein forming a patterned layer comprises:
forming a metal oxide layer overlying the dielectric layer on the semiconductor wafer; and
patterning the metal oxide layer into a plurality of metal oxide regions,
wherein the metal oxide regions are configured to receive nucleic acid macromolecules.

16. The method of claim 14, wherein forming a patterned layer comprises:
forming a metal oxide layer overlying the dielectric layer on the semiconductor wafer;
forming a silicon oxide layer overlying the metal oxide layer; and
patterning the silicon oxide layer,
wherein regions of the metal oxide layer not covered by the silicon oxide layer.

17. The method of claim 14, further comprising bonding the glass wafer to the semiconductor wafer.

18. The method of claim 14, further comprising functionalizing the sequencing flow cell, wherein functionalizing the sequencing flow cell comprises exposing the sequencing flow cell to materials supplied through the inlet and outlet to form hydrophilic surface regions and hydrophobic surface regions.

19. The method of claim 15, further comprising functionalizing the sequencing flow cell, wherein functionalizing the sequencing flow cell comprises exposing the sequencing flow cell to materials supplied through the inlet and outlet to form hydrophilic surface regions and hydrophobic surface regions.

* * * * *